(12) United States Patent
Sung et al.

(10) Patent No.: US 11,286,484 B2
(45) Date of Patent: Mar. 29, 2022

(54) USE OF MIR-18B FOR PREVENTION, TREATMENT, OR DIAGNOSIS OF MUSCLE DISEASE AND NEUROMUSCULAR DISEASE

(71) Applicant: CURAMYS CO., LTD., Seoul (KR)

(72) Inventors: Jung-Joon Sung, Seoul (KR); Ki Yoon Kim, Seoul (KR)

(73) Assignee: CURAMYS CO., LTD., Seoul (KR)

( * ) Notice: Subject to any disclaimer, the term of this patent is extended or adjusted under 35 U.S.C. 154(b) by 0 days.

(21) Appl. No.: 16/791,185

(22) Filed: Feb. 14, 2020

(65) Prior Publication Data

US 2020/0277603 A1    Sep. 3, 2020

Related U.S. Application Data

(63) Continuation-in-part of application No. PCT/KR2018/009461, filed on Aug. 17, 2018.

(30) Foreign Application Priority Data

Aug. 18, 2017 (KR) .......... 10-2017-0105029
Aug. 9, 2018 (KR) .......... 10-2018-0092805

(51) Int. Cl.
| | | |
|---|---|---|
| C12N 15/11 | (2006.01) | |
| C12N 15/113 | (2010.01) | |
| A61P 21/00 | (2006.01) | |
| C12Q 1/6883 | (2018.01) | |

(52) U.S. Cl.
CPC .......... *C12N 15/113* (2013.01); *A61P 21/00* (2018.01); *C12Q 1/6883* (2013.01); *C12N 2310/141* (2013.01); *C12Q 2600/158* (2013.01); *C12Q 2600/178* (2013.01)

(58) Field of Classification Search
CPC .......... C12N 15/113; C12N 2310/141; C12Q 1/6883; C12Q 2600/158; C12Q 2600/178
See application file for complete search history.

(56) References Cited

U.S. PATENT DOCUMENTS

2013/0184331 A1* 7/2013 Roh .......... A61P 25/00
514/44 A

FOREIGN PATENT DOCUMENTS

| JP | 2009519339 A | 5/2009 |
|---|---|---|
| JP | 2011515407 A | 5/2011 |
| JP | 2013542921 A | 11/2013 |
| JP | 2016088896 A | 5/2016 |
| KR | 1020120088009 A | 8/2012 |
| KR | 1020140130562 A | 11/2014 |
| KR | 1020160139849 A | 12/2016 |
| WO | 2011105556 A1 | 9/2011 |
| WO | 2013070079 A2 | 5/2013 |
| WO | 2014047267 A1 | 3/2014 |

OTHER PUBLICATIONS

35th Annual Meeting of the Korean Neurological Association, miR-18b dysregulation regulates miR-206 expression and induces cell death in S0D1, 2016, pp. 178-179.
Andrew H. Williams et al., MicroRNA-206 Delays ALS Progression and Promotes Regeneration of Neuromuscular Synapses in Mice, 2009, pp. 1549-1554, vol. 326, Science AAAS.
Beata Narozna et al., Non-Coding RNAs in Pediatric Airway Diseases, 2017, pp. 1-16, MDPI.
Brent A. Reynolds et al., Generation of Neurons and Astrocytes from Isolated Cells of the Adult Mammalian Central Nervous System, 1992, pp. 1707-1710, vol. 255, Reports.
Daniel R. Rosen et al., Mutations in Cu/Zn superoxide dismutase gene are associated with familial amyotrophic lateral sclerosis, 1993, pp. 59-62, vol. 362, Nature.
Eugene V. Makeyev et al., The MicroRNA miR-124 Promotes Neuronal Differentiation by Triggering Brain-Specific Alternative Pre-mRNA Splicing, 2007, pp. 435-448, vol. 27, Molecular Cell, Elsevier.
Eunhyun Choi et al., Roles of Calcium Regulating MicroRNAs in Cardiaclschemia-Reperfusion Injury, 2014, pp. 899-913, cells.
Guoda Ma et al., MiR-206, a Key Modulator of Skeletal Muscle Development and Disease, 2015, pp. 345-352, vol. 11, International Journal of Biological Sciences.
Heidi R. Fuller et al., Spinal Muscular Atrophy Patient iPSC-Derived Motor Neurons Have Reduced Expression of Proteins Important in Neuronal Development, 2016, pp. 1-15, vol. 9, Frontiers in Cellular Neuroscience.
Jaya Krishnan et al., Essential Role of Developmentally Activated Hypoxia-Inducible Factor 1alpha for Cardiac Morphogenesis and Function, 2008, pp. 1139-1146, Circulation Research.
Jeffrey Gagan et al., Notch3 and Mef2c Proteins Are Mutually Antagonistic via Mkp1 Protein and miR-1/206 MicroRNAs in Differentiating Myoblasts, 2012, pp. 40360-40370, vol. 287, No. 48, The Journal of Biological Chemistry.
Karamjit S. Dolt et al., cDNA cloning, gene organization and variant specific expression of HIF-alpha in high altitude yak (*Bos grunniens*), 2007, pp. 73-80, ScienceDirect, Elsevier.
Laura C. O'Brien et al., Differentiation of Human Neural Stem Cells into Motor Neurons Stimulates Mitochondiral Biogenesis and Decreases Glycolytic Flux, 2015, 27 pages, Virginia Commonwealth University, Stem Cells and Development.

(Continued)

*Primary Examiner* — Ekaterina Poliakova-Georgantas
(74) *Attorney, Agent, or Firm* — Cantor Colburn LLP

(57) ABSTRACT

The present invention relates to use of miR-18b for prevention, treatment, or diagnosis of muscle diseases or neuromuscular diseases, and specifically it was confirmed that, in a muscle disease by gene mutations model, gene mutations reduce miR-18b expression, cause dysregulation of miR-18b signaling pathways, and thus induce calcium signaling, cell differentiation inhibition, and apoptosis. Therefore, miR-18b of the present invention may be used as a target factor for diagnosing and treating muscle diseases caused by gene mutations such as ALS and DMD.

5 Claims, 54 Drawing Sheets

Specification includes a Sequence Listing.

(56) References Cited

OTHER PUBLICATIONS

Lifeng Qiu et al., Multiple C2 domains transmembrane protein 1 is expressed in CNS neurons and possibly regulates cellular vesicle retrieval and oxidative stress, 2015, pp. 492-507, vol. 135, Expression and function of MCTP1 in neuronal cells.

Monika Rataj-Baniowska et al., Retinoic Acid Receptor β Controls Development of Striatonigral Projection Neurons through FGF-Dependent and Meis1-Dependent Mechanisms, 2015, pp. 14467-14475, vol. 35, No. 43, The Journal of Neuroscience.

Myung-Soo Cho et al., Efficient derivation of functional dopaminergic neurons from human embryonic stem cells on a large scale, 2008, pp. 1888-1894, vol. 3, No. 12, Nature Protocols.

Ok-Ho Shin et al., Evolutionarily Conserved Multiple C2 Domain Proteins with Two Transmembrane Regions (MCTPs) and Unusual Ca2+ Binding Properties, 2005, pp. 1641-1651, vol. 280, No. 2, The Journal of Biological Chemistry.

Ras Trokovic, Advanced Feeder-Free Generation of Induced Pluripotent Stem Cells Directly From Blood Cells, 2014, pp. 1402-1409, AlphaMed Press. Stem Cells Translational Medicine.

Sophie Koszinowski et al., RARβ Regulates Neuronal Cell Death and Differentiation in the Avian Ciliary Ganglion, 2015, pp. 1204-1218, Developmental Neurobiology.

Wooseok Im et al., Multidrug resistance protein 1 reduces the aggregation of mutant huntingtin in neuronal cells derived from the Huntington's disease R6/2 model, 2015, pp. 1-10, Scientific Reports.

Xuejuan Liu et al., miR-18b inhibits TGF-b1-induced differentiation of hair follicle stemcells into smooth muscle cells by targeting SMAD2, 2013, pp. 551-556, Biochemical and Biophysical Research Communication, Elsevier.

Yin Li et al., Regulation of RARβ Expression by RAR- and RXR-Selective Retinoids in Human Lung Cancer Cell Lines: Effect on Growth Inhibition and Apoptosis Induction, 1998, pp. 88-95, vol. 75, Int. J. Cancer.

Yoshihiro Nihei et al., Enhanced Aggregation of Androgen Receptor in Induced Pluripotent Stem Cell-derived Neurons from Spinal and Bulbar Muscular Atrophy, 2013, pp. 8043-8052, vol. 288, No. 12, The Journal of Biological Chemistry.

Yuin-Han Loh et al., Generation of induced pluripotent stem cells from human blood, 2009, pp. 5476-5479, vol. 113, No. 22, Blood, Hematopoiesis and Stem Cells.

Z Chen et al., Hypoxia-regulated microRNA-210 modulates mitochondrial function and decreases ISCU and COX10 expression, 2010, pp. 4362-4368, NPG, Macmillan Publishers Limited.

International Search Report for PCT/KR2018/009461 dated Dec. 18, 2018, citing the above reference(s).

Written Opinion for PCT/KR2018/009461 dated Dec. 18, 2018, citing the above reference(s).

Notice of Allowance dated Jul. 13, 2021 for JP 2020-531407.

\* cited by examiner

Mctp1 3' UTR  5'-AGAAUUUCAAUCAAUCAUUCCAU-3' (SEQ ID NO: 62)
miR-206       3'-GGUGUGUGAAGGAAGUAAGGU-5' (SEQ ID NO: 63)
Rarb 3' UTR   5'-UUCUAGCUACUUCAACAUUCCC-3' (SEQ ID NO: 64)

Hif1α 3' UTR  5'-AUCAUUUUAAAAAAUGCACCUUU-3' (SEQ ID NO: 65)
miR-18b       3'-GAUUGACGUGAUCUACGUGGAA-5' (SEQ ID NO: 66)

USE OF MIR-18B FOR PREVENTION, TREATMENT, OR DIAGNOSIS OF MUSCLE DISEASE AND NEUROMUSCULAR DISEASE

RELATED APPLICATIONS

This application is a continuation in part of PCT application no. PCT/KR2018/009461, filed on Aug. 17, 2018, which claims priority to Korean Patent Application No. 10-2017-0105029, filed on Aug. 18, 2017 and Korean Patent Application No. 10-2018-0092805, filed on Aug. 9, 2018, in the Korean Intellectual Property Office, the disclosure of which is incorporated herein in its entirety by reference.

SEQUENCE LISTING

A Sequence Listing, incorporated herein by reference, is submitted in electronic form as an ASCII text file, of size 12 Kb, created Oct. 15, 2020, and named "8MR673702.TXT".

TECHNICAL FIELD

The present invention relates to use of miR-18b for prevention, treatment, or diagnosis of muscle diseases or neuromuscular diseases, and specifically a method for preventing or treating muscle diseases, including administering a composition comprising a pharmaceutically effective amount of miR-18b to a subject, and a method of diagnosing muscle diseases, using miR-18b.

BACKGROUND ART

A muscle disease is a disease with which people complain muscle weakness in the upper or lower extremities, general muscular atrophy resulted from the weakness, reduced muscle tension, muscle spasms, severe pain in the muscle, and the like due to inherited and degenerative, inflammatory, endocrine, metabolic causes, and the like. Particularly, due to the inherited and degenerative causes, muscular dystrophy, amyotrophic lateral sclerosis (ALS), spinal muscular amyotrophy, spinobular muscular atrophy, Charcot Marie Tooth disease (CMT), Pompe disease, sacopenia, Canavan disease, dystonia, sacopenia, muscular degeneration, and the like are exhibited.

For example, the amyotrophic lateral sclerosis outbreaks due to the following genetic mutations: SOD1 (Cu/Zn superoxide dismutase 1), TATA-Box Binding Protein Associated Factor 15 (TAF15), Ewing sarcoma breakpoint region 1 (EWSR1), Fused in Sarcoma (FUS), and TAR DNA-binding protein 4 (TDP-43). In addition, the amyotrophic lateral sclerosis (ALS) is a degenerative disease of upper and lower motor neurons that progresses muscle dysfunction at an initial stage, and finally causes muscle paralysis. Unfortunately, there are few options for slowing down disease progression or improving the quality of life of the ALS patients.

In addition, Duchenne-type and Becker-type muscular dystrophy outbreaks due to abnormalities of the dystrophin gene that is present on X chromosomes. About one third thereof is caused due to natural mutations, and the rest are caused by the hereditary inheritance. Muscle weakness, myocardial dysfunction, and the like are exhibited.

In addition, spinal muscular atrophy outbreaks due to a mutation in the SMN1 gene encoding a survival motor neuron (SMN) protein in eukaryotes, and causes functional impairment to motor neurons that are present between the spinal cord and the brain stem due to a decrease in the SMN protein, so that the muscles do not receive a signal to command the movement of the muscles and are neglected, thereby causing hypotonia, myoatrophy, fasciculation, and the like.

Gene mutations that become the cause of the development of these muscle diseases are associated with a variety of cellular processes such as autophagy, protein aggregation, mitochondrial stress, and RNA metabolism.

Meanwhile, microRNAs (or miRNAs) are small non-coding single-stranded RNA molecules that regulate protein synthesis by RNA-dependent post-transcriptional gene regulation, and miRNAs are produced in a two-step process. Specifically, in the nucleus, the first transcript miRNAs (pri-miRNAs) is made to miRNAs precursors (pre-miRNAs) by Drosha and DGCR8, and the pre-miRNAs are released into the cytoplasm and made into miRNAs by Dicer. Recently, as it has been known that miRNA is associated with cellular processes such as mitochondrial gene expression, calcium signaling, cell differentiation, and apoptosis and that gene mutations regulate miRNA biosynthesis, research has been conducted to reveal the role of miRNA in the pathogenesis of diseases caused by gene mutations and to use miRNA in the diagnosis or treatment of diseases. However, the specific interaction mechanisms of gene mutations and miRNAs in muscle diseases caused by genetic causes are not fully understood.

Therefore, the present inventors have tried to discover miRNAs that may be used for diagnosing and treating muscle diseases, resultantly confirmed that, in a muscle disease caused by gene mutations model, gene mutations reduce miR-18b expression, cause dysregulation of miR-18b signaling pathways, and thus induce calcium signaling, cell differentiation inhibition, and apoptosis, and found that miR-18b may be used as a target factor for diagnosis and treatment of muscle diseases caused by gene mutations such as ALS and DMD, to complete the present invention.

CITATION LIST

Non Patent Literature

Rosen D R, Siddique T, Patterson D, Figlewicz D A, Sapp P, Hentati A, Donaldson D, Goto J, O'Regan J P, Deng H X, et al. Mutations in Cu/Zn superoxide dismutase gene are associated with familial amyotrophic lateral sclerosis. Nature. 1993 Mar. 4; 362(6415): 59-62.

Narozna B, Langwinski W, Szczepankiewicz A. Non-Coding RNAs in Pediatric Airway Diseases. Genes (Basel). 2017 Nov. 27; 8(12).

Chen Z, Li Y, Zhang H, Huang P, Luthra R. Hypoxia-regulated microRNA-210 modulates mitochondrial function and decreases ISCU and COX10 expression. Oncogene. 2010 Jul. 29; 29(30): 4362-8.

Choi E, Cha M J, Hwang K C. Roles of Calcium Regulating MicroRNAs in Cardiac Ischemia-Reperfusion Injury. Cells. 2014 Sep. 11; 3(3): 899-913.

Makeyev E V, Zhang J, Carrasco M A, Maniatis T. The MicroRNA miR-124 promotes neuronal differentiation by triggering brain-specific alternative pre-mRNA splicing. Mol Cell. 2007 Aug. 3; 27(3): 435-48.

Morales M G, Gutierrez J, Cabello-Verrugio C, Cabrera D, Lipson K E, Goldschmeding R, Brandan E. Reducing CTGF/CCN2 slows down mdx muscle dystrophy and improves cell therapy. Hum Mol Genet. 2013 Dec. 15; 22(24):4938-51.

SUMMARY OF INVENTION

Technical Problem

An object of the present invention is to provide a method for preventing or treating muscle diseases, including administering a composition comprising a pharmaceutically effective amount of miR-18b to a subject.

Another object of the present invention is to provide a method of diagnosing muscle diseases using miR-18b.

Solution to Problem

In order to achieve the objects of the present invention, the present invention also provides a method for preventing or treating muscle diseases, including administering a composition comprising a pharmaceutically effective amount of miR-18b to a subject.

In addition, the present invention also provides a method for diagnosing muscle diseases, comprising measuring an expression level of miR-18b in a sample isolated from a subject and comparing the sample with a normal control.

Advantageous Effects of Invention

The present invention confirms that, in a muscle disease caused by gene mutations model, gene mutations reduce miR-18b expression, cause dysregulation of miR-18b signaling pathways, and thus induce calcium signaling, cell differentiation inhibition, and apoptosis. In addition, the present invention confirms that the increase of the miR-18b expression suppresses apoptosis caused by the gene mutations and recovers calcium signaling and cell differentiation. Therefore, miR-18b of the present invention may be used as a target factor for diagnosing and treating muscle diseases caused by gene mutations such as ALS and DMD.

DESCRIPTION OF EMBODIMENTS

Figure 1A:
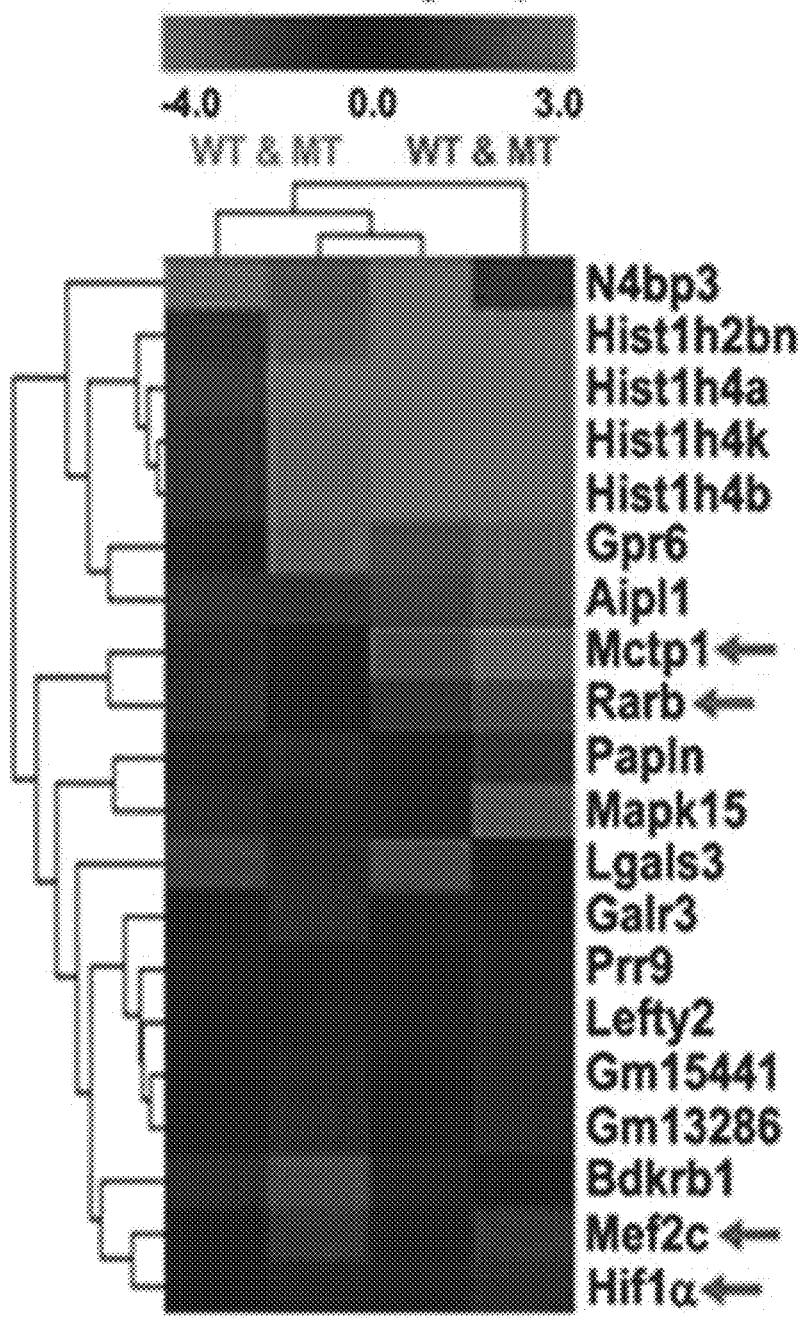
FIGS. 1A to 1D are diagrams confirming RNA biosynthesis changes in NSC-34 motor neurons (mtNSC-34 cells) expressing human SOD1 (G93A) according to an example of the present invention and NSC-34 motor neurons (wtNSC-34 cells) expressing human SOD1 as a control group, and expression changes in four genes having expression differences between mtNSC-34 cells and wtNSC-34 cells: hypoxia inducible factor 1 alpha (Hif1α), myocyte specific enhancer factor 2c (Mef2c), multiple C2 domains transmembrane protein 1 (Mctp1), and retinoic acid receptor beta (Rarb)

Hereinafter, the present invention is described in more detail.

The present invention provides a method for preventing or treating muscle diseases, including administering a composition comprising a pharmaceutically effective amount of miR-18b to a subject.

According to the present invention, miR-18b may be derived from animals including humans, such as monkeys, chimpanzees, pigs, horses, cows, sheep, dogs, cats, mice, rabbits.

According to the present invention, the nucleic acid molecule forming miR-18b may have a length of 18 to 100 nt (nucleotide). Specifically, the nucleic acid molecule may be in the form of a mature miRNA having a length of 19 to 25 nt, more specifically having a length of 21, 22, or 23 nt. In addition, the nucleic acid molecule may be in the form of a precursor miRNA having a length of 50 to 100 nt, more specifically having a length of 65 to 95 nt.

In addition, the miR-18b in the form of mature miRNA may specifically be miR-18b-5p or miR-18b-3p, more specifically miR-18b-5p.

The sequence information of the nucleic acid molecule of miR-18b in the form of mature miRNA or precursor miRNA may be confirmed in known genetic databases such as GenBank of the US National Institutes of Health (NIH GenBank) and miRBASE (http://www.mirbase.org/) are the like. For example, the sequence of human miR-18b in the mature form is registered with the gene registration number of MIMAT0001412 (SEQ ID NO: 1) or MIMAT0004751 (SEQ ID NO: 2), and the sequence of human miR-18b in the precursor form is registered with the gene registration number of MI0001518 (SEQ ID NO: 3).

TABLE 1

| Gene | | | Sequence information |
|---|---|---|---|
| hsa-miR-18b | Mature form | miR-18b-5p | UAAGGUGCAUCUAGUGCAGUUAG (SEQ ID NO: 1) |
| | | miR-18b-3p | UGCCCUAAAUGCCCCUUCUGGC (SEQ ID NO: 2) |
| | Precursor form | | UGUGUUAAGGUGCAUCUAGUGCAGUUAGUGA AGCAGCUUAGAAUCUACUGCCCUAAAUGCCC CUUCUGGCA (SEQ ID NO: 3) |

In addition, miR-18b used in the present invention is a concept including a functional equivalent of a nucleic acid molecule forming the same, for example, mutation that can have functionally the same effect as the miRNA nucleic acid molecule even if some sequences of the miRNA nucleic acid molecule is modified by deletion, substitution, or insertion. For example, miR-18b of the present invention may exhibit a homology of 80% or more with the sequence of each corresponding SEQ ID NO, specifically a homology of 90% or more, more specifically a homology of 95% or more. Such homology may be easily determined by using computer algorithms well known in the art, such as the Align or BLAST algorithms, in the comparison with the sequence of nucleotides with corresponding portions of the target gene.

In addition, miR-18b used in the present invention may be present in a single-stranded or double-stranded form. Mature miRNA molecules are mainly single stranded, but precursor miRNA molecules may include partial self-complementary structures (for example, stem-loop structures) capable of forming double strands. In addition, the nucleic acid molecules of the present invention may be configured in the form of RNA or peptide nucleic acids (PNA).

In addition, miR-18b used in the present invention may be isolated or prepared using standard molecular biology techniques such as chemical synthesis or recombinant methods or may be obtained from a commercially available product.

In the present invention, miR-18b itself may be included, but a functionally equivalent fragment thereof may be included, and the fragment of the miRNA may be a polynucleotide including a seed sequence of the miRNA. The seed sequence refers to the nucleotide sequence in some regions in the miRNA that binds with complete complementarity when the miRNA recognizes the target and is a part essential for the miRNA to bind to the target.

In addition, the miR-18b may be used in the form of various miRNA derivatives (miRNA mimic) that generate its biological equivalent efficacy, and a modified miRNA including a miRNA sequence including the same seed region may be used. The miRNA derivative for the miRNA may partially include a phosphorothiolate structure in the form in which the RNA phosphate backbone structure is substituted with another element such as sulfur, and may be used in the form of being entirely or partially substituted with DNA and peptide nucleic acid (PNA) molecules instead of RNA and may be used in the form in which a 2' hydroxyl group of the RNA sugar is substituted with various functional structures, and the substitution includes methylation, methoxylation, fluorination, and the like but the present invention is not limited to these modifications.

In the present invention, the miR-18b may be provided in a form of being included in a vector or introduced into a cell.

Specifically, miR-18b may be provided included in an expression vector for intracellular delivery. As the expression vector, both viral and non-viral vector may be used. Examples of the viral vector include lentivirus, retrovirus, adenovirus, herpes virus, or avipox virus vectors, but the present invention is not limited thereto.

The expression vector may further include a selection marker to facilitate selection of the transduced cells. Examples thereof include markers that provide selectable phenotypes such as drug resistance, nutritional requirements, resistance to cytotoxic agents, or expression of surface proteins, for example, green fluorescent protein, puromycin, neomycin, hygromycin, histidinol dihydrogenase (hisD), and guanine phosphoribosyl transferase (Gpt).

In addition, miR-18b may be provided in a form of being introduced into cells. These cells can express miR-18b at high level. As a method of introducing into a cell, miR-18b may be introduced into cells together with delivery reagents including G-fectin, Mirus TrasIT-TKO lipid-affinity reagents, lipofectin, lipofectamine, cellfectin, cationic phospholipid nanoparticles, cationic polymers, cationic micelles, cationic emulsions, or liposomes, or may be conjugated with biocompatible polymers such as polyethylene glycol to increase intracellular uptake.

In the present invention, the muscle disease may be a muscle disease caused by gene mutation, but the present invention is not limited thereto.

In addition, the muscle disease may be myasthenia gravis, progressive muscular dystrophy, myotonic muscular dystrophy, Duchenne muscular dystrophy, Backer muscular dystrophy, Limb Girdle muscular dystrophy, facioscapulohumerali muscular dystrophy, spinal muscular amyotrophy, muscular atrophy, amyotrophic lateral sclerosis, spinobulbar muscular atrophy, Charcot Marie Tooth disease (CMT), Pompe disease, Canavan disease, dystonia, sacopenia, or muscular degeneration, but the present invention is not limited thereto.

In the specific example of the present invention, the present inventors confirmed that, in the muscle disease caused by the gene mutation model of amyotrophic lateral sclerosis, the gene mutation reduces miR-18b expression and causes the regulation disorder of the miR-18b signaling pathway, the miR-18b regulation disorder induces upregulation of Hif1α, the upregulated Hif1α upregulates Mef2c, the Mef2c induces miR-206 expression, and miR-206 directly involves in post-transcriptional regulation of Mctp1 and Rarb, to induce the calcium signaling, neuron differentiation suppression, and apoptosis. Also, the present inventors confirmed that the increase of the miR-18b expression suppresses the apoptosis induced by the gene mutation and recovers the calcium signaling and the cell differentiation.

In addition, the present inventors confirmed that the regulation disorder of the miR-18b signaling pathway is caused by the gene mutation in Duchenne muscular dystrophy model as the muscle disease by gene mutation model.

In addition, the present inventors confirmed that CTGF expression increased in muscle tissues is decreased by miR-18b in the Duchenn muscular dystrophy model as the muscle disease caused by gene mutations model.

Therefore, the present inventors confirmed that, in the muscle disease by gene mutation model, the gene mutation reduces the miR-18b expression and causes the regulation disorder of the miR-18b signaling pathway, and thus induces the calcium signaling, the cell differentiation suppression, and the apoptosis, and the increase of the miR-18b expression suppresses the apoptosis induced by the gene mutation and recovers the calcium signaling and the cell differentiation, and thus the miR-18b of the present invention may be used for preventing or treating the muscle disease.

The composition of the present invention may further include a pharmaceutically acceptable carrier and may be formulated with the carrier.

The pharmaceutically acceptable carrier refers to a carrier or a diluent that does not stimulate an organism and does not inhibit the biological activity and properties of the administered compound. Examples of the pharmaceutical carriers that are acceptable in compositions formulated as liquid solutions include sterile and physiologically compatible solutions, such as saline, sterile water, Ringer's solution, buffered saline, albumin injectable solutions, dextrose solutions, maltodextrin solution, glycerol, ethanol, and a mixture of one or more of these ingredients, and other additives in the related art such as antioxidants, buffers, bacteriostatic agents may be added, if necessary. The carriers may also be formulated in the form of a solution or suspension (for example, integrated with microparticles, liposomes, or cells).

The composition of the present invention is applicable to any formulation containing the composition as an active ingredient and may be prepared and administered in oral or parenteral formulations. Administration means introducing the composition of the present invention to a patient by a certain proper method and includes transportation of nucleic acid molecules by a viral or non-viral technique or transplantation of cells expressing nucleic acid molecules. With respect to the pathway for administering the composition of the present invention, the composition may be administered in various oral or parenteral pathways as long as the composition can reach the desired tissue. Examples thereof include oral administration, intraperitoneal administration, intravenous administration, intramuscular administration, subcutaneous administration, intradermal administration, intranasal administration, pulmonary administration, rectal administration, intraluminal administration, intraperitoneal administration, and intradural administration, but the present invention is not limited thereto.

The composition and the treatment method of the present invention may be applied to any animals in which muscle diseases can develop, and examples of the animals include humans and primates, as well as domestic animals such as cows, pigs, sheep, horses, dogs, and cats.

It will be apparent to those skilled in the art that the range of effective amounts or the suitable total daily usage of the compositions of the present invention may be determined by the practitioner under correct medical judgment. It is desirable that the specific therapeutically effective amount for a particular patient is differently applied depending on the type and severity of the response to be achieved, specific compositions including whether other agents are used in cases, various factors including ages, body weights, general health, sex, and diet of the patient, administration time, administration path, the rate of release of the composition, the duration of treatment, and the radiation dose to be irradiated, and similar factors well known in the medical arts. For example, the composition may be used at 0.001 µg/kg to 100 mg/kg (body weight) per day, but the present invention is not limited thereto. An effective amount of a pharmaceutical composition suitable for the purpose of the present invention is desirably determined in consideration of the foregoing.

The present invention also provides a method of providing diagnostic information of muscle diseases, including measuring the expression level of miR-18b in a sample isolated from a subject and comparing the expression level with that of a normal control.

In the method of the present invention, the sample may be tissues, cells, plasma, serum, blood, saliva, or urine, but the present invention is not limited thereto.

In the method of the present invention, the expression level may be measured by reverse transcription polymerase chain reaction (RT-PCR), quantitative RT-PCR, real-time RT-PCR, Northern blotting, or transcriptome analysis methods, but the present invention is not limited thereto.

In the method of the present invention, muscle diseases may be diagnosed by confirming that the expression level of miR-18b in the above sample is reduced in comparison with the normal control.

In addition, muscle diseases may be diagnosed by additionally measuring the expression level of Hif1α, Mef2c, Mctp1, Rarb, or miR-206 in the sample and comparing with a normal control. Specifically, it is confirmed that the expression level of Hif1α, Mef2c, or miR-206 in the sample is increased in comparison with the normal control to diagnose muscle diseases, and it is confirmed that the expression level of Mctp1 or Rarb is reduced in comparison with a normal control to diagnose muscle diseases.

In the method of the present invention, the muscle disease may be a muscle disease caused by a gene mutation, but the present invention is not limited thereto.

In addition, the muscle disease may be myasthenia gravis, progressive muscular dystrophy, myotonic muscular dystrophy, Duchenne muscular dystrophy, Backer muscular dystrophy, Limb Girdle muscular dystrophy, facioscapulohumeral muscular dystrophy, spinal muscular amyotrophy, muscular atrophy, amyotrophic lateral sclerosis, spinobulbar muscular atrophy, Charcot Marie Tooth disease (CMT), Pompe disease, Canavan disease, dystonia, sacopenia, or muscular degeneration, but the present invention is not limited thereto.

The present inventors confirmed that, in the muscle disease by gene mutation model, the gene mutation reduces the miR-18b expression and causes the regulation disorder of the miR-18b signaling pathway, the miR-18b regulation disorder induces upregulation of Hif1α, the upregulated Hif1α upregulates Mef2c, the Mef2c induces miR-206 expression, and miR-206 directly involves in post-transcriptional regulation of Mctp1 and Rarb to induce the calcium signaling, neuron differentiation suppression, and apoptosis, and thus miR-18b of the present invention and the above factors regulated by miR-18b can be used as target factors for diagnosing muscle diseases.

Hereinafter, the present invention is described in detail with reference to examples.

However, the following examples are merely provided to exemplify the present invention, but the content of the present invention is not limited by the following examples.

<Example 1> Cell Culture

<1-1> SOD1 Mutant Motor Neuron Culture

It is well-known that atrophic lateral sclerosis (ALS) is a muscle disease caused by gene mutation, is developed by SOD1 mutation, and causes motor neurons to be lost. In order to find out the target miRNA that can be used for ALS diagnosis and treatment, SOD1 mutant motor neurons were cultured as follows.

Specifically, NSC-34 cont cells which are a motor neuron cell line expressing mouse SOD1, NSC-34 hSOD1 cells (wtNSC-34) which are a motor neuron cell line expressing human SOD1, and NSC-34 hSOD1 (G93A) cells (mtNSC-34) which are a SOD1 mutant motor neuron cell line expressing human SOD1 G93A mutation were obtained from Korea Institute of Science and Technology (KIST). Then, the cells were cultured in a DMEM medium (Hyclone Laboratories Inc.) added with 10% of FBS (Gibco), 100 U/ml of penicillin, 100 μg/ml of streptomycin (Invitrogen, Life Technologies Corporation). The cells were also differentiated in a DMEM medium (Hyclone Laboratories Inc.) to which 1% of FBS, 100 U/ml of penicillin, 100 μg/ml of streptomycin, and 20 uM of all-trans-RA (Sigma-Aldrich, Inc.) were added.

<1-2> Neuron Stem Cell Isolation and Culture

To identify target miRNA that can be used for ALS diagnoses and treatments, neuron stem cells (NSC) were isolated and cultured as follows.

Specifically, animal experiments were performed according to the guidelines of Institutional Animal Care and Use Committee (IACUC) of Seoul National University for experimental animal care and use. Brain tissues of the subventricular zones of 9-week-old mice were extracted, disrupted in plates containing HBSS, and cultured for 15 minutes at 37° C. after a trypsin treatment. Subsequently, after the cells were centrifuged and resuspended in a DMEM/F12 (Invitrogen) medium including 1% of penicillin-streptomycin-amphotericin (PSA, Invitrogen), 2% of B27 supplement (Gibco BRL), 10 ng/mL of EGF (Invitrogen), and 10 ng/mL of bEGF (Invitrogen), the cells were seeded in 6-well plates to culture NSC. To induce cell differentiation, when the cells formed neurospheres having a diameter of about 50 to 100 μm, the cells were resuspended and transferred to sterile 15-ml tubes. The cells were centrifuged at 100×g for five minutes at room temperature to obtain pellets containing neurospheres, the pellets were resuspended in a differentiation culture medium (DMEM/F12, 1% of PSA, 2% of B27, and 5% of FBS) and cultured.

<1-3> Culture of Dystrophin Expression Suppression Myoblast

As a muscle disease caused by gene mutation, it is well-known that Duchenn muscular dystrophy (DMD) is developed by Dystrophin deficiency due to Dystrophin gene mutation. Thus, in order to identify target miRNA that can be used for the diagnosis and treatment of Duchenn muscular dystrophy, Dystrophin expression suppression myoblasts were prepared and cultured as follows.

Specifically, mouse myoblasts (C2C12 cell line) were cultured in a DMEM medium (10% FBS addition) to which antibiotics were added. Mouse siDystrophin (5'-GGCC-UUACAGGGCAAAAACTT-3', SEQ ID NO: 4) prepared by COSMO GENETECH Co., Ltd. upon request was transduced to cultured C2C12 cells according to procedures of the manufacturer by using a RNAiMax transfection reagent (Invitrogen) to prepare and culture Dystrophin expression suppression C2C12 cells.

<Example 2> Confirming Abnormal Gene Expression in SOD1 Mutant Motor Neurons

The gene mutation relates to RNA biosynthesis, and thus miRNA involved in RNA biosynthesis can be used as a target factor for ALS diagnosis and treatment as muscle diseases caused by gene mutations. In order to identify RNA biosynthesis changes caused by SOD1 mutations, mtNSC-cells were fractionated into nuclei and cytoplasm, transcriptome analysis was performed by using nuclear and cytoplasmic fractions, and RT-PCR and qRT-PCR were performed to confirm expression of genes that have expression differences between nuclei and cytoplasm.

Specifically, each of mtNSC-34 cells and wtNSC-34 cells obtained in Example <1-1> was cultured in three sets of 10-cm dishes and then was collected by using 450 μl of a cold buffer A (10 mM of HEPES (pH 7.9), 10 mM of KCl, 1 mM of DTT, and 0.1 mM of EDTA (pH 8.0)). Each of mtNSC-34 cells and wtNSC-34 cells was resuspended and reacted for 25 minutes on ice. Subsequently, 5 μl of 10% of NP-40 was added, reacted on ice for two minutes, and centrifuged at 5,000 rpm for three minutes at 4° C. The pellets were isolated to obtain nuclear fractions, and the supernatant was isolated to obtain cytoplasmic fractions. RNA-seq analysis was performed using the 12 samples of transcriptomes in total by requesting Macrogen Inc.

Also, expression of four kinds of genes having expression difference between mtNSC-34 cells and wtNSC-34 cells: hypoxia inducible factor 1 alpha (Hif1α), myocyte specific enhancer factor 2c (Mef2c), multiple C2 domains transmembrane protein 1 (Mctp1), and retinoic acid receptor beta (Rarb) mRNA was confirmed by RT-PCR and quantitative RT-PCR (qRT-PCR). Specifically, in order to confirm expression changes in two kinds of genes: Mctp1 and Rarb mRNA having expression differences between nuclei and cytoplasm, nuclear and cytoplasmic fractions were obtained from each of mtNSC-34 cells and wtNSC-34 cells by the same method as above, total RNA was extracted by using a TRIzol reagent (MRC), and a primer of Table 2 was used to perform RT-PCR (FIG. 1B). In order to confirm the expression changes of Hif1α, Mef2c, Mctp1, and Rarb mRNA in the mtNSC-34 cells, total RNA was extracted from each of mtNSC-34 cells and wtNSC-34 cells by using a TRIzol reagent (MRC), 50 ng of RNA was used as a template, and a primer of Table 3 and SYBR Green Real-time PCR Master Mix (Toyobo) were used to perform qRT-PCR according to the procedures of the manufacturer. Mouse GAPDH was used as a control (FIGS. 1C and 1D).

TABLE 2

| Gene | | Mouse primer (5'→3') |
|---|---|---|
| Mctp1 intron | Forward | GACTCCAACATACCCATTTCTG (SEQ ID NO. 5) |
| | Reverse | TAATATCTCTTCCCGCTCCTTC (SEQ ID NO. 6) |
| Mctp1 exon | Forward | TCATCCTTACGCCTAAGGAAG (SEQ ID NO. 7) |
| | Reverse | CCGGAACTTCACATATGGATC (SEQ ID NO. 8) |
| Rarb intron | Forward | CACCTGAAGGTGAATGTTGG (SEQ ID NO. 9) |
| | Reverse | CACTTGAACTTGGGGTCAAG (SEQ ID NO. 10) |
| Rarb exon | Forward | GATCTACACTTGCCATCGAGA (SEQ ID NO.11) |
| | Reverse | CTTTCCGGATCTTCTCAGTGA (SEQ ID NO. 12) |
| GAPDH intron | Forward | TGGTGCAACAGTATTCCACT (SEQ ID NO. 13) |
| | Reverse | CTGGAACATGTAGACCATGTAG (SEQ ID NO. 14) |
| GAPDH exon | Forward | CATGTTTGTGATGGGTGTGA (SEQ ID NO. 15) |
| | Reverse | GATGCAGGGATGATGTTCTG (SEQ ID NO. 16) |

TABLE 3

| Gene | | Mouse primer (5'→3') |
|---|---|---|
| Hif1α | Forward | GTTCACCAAAGTTGAATCAGAGG (SEQ ID NO. 17) |
| | Reverse | CGATGAAGGTAAAGGAGACATTG (SEQ ID NO. 18) |
| Mef2c | Forward | AGGATAATGGATGAGCGTAACAG (SEQ ID NO. 19) |
| | Reverse | AGCAACACCTTATCCATGTCAGT (SEQ ID NO. 20) |
| Mctp1 | Forward | CGTTGTGTCATAGTGCTTGTAAA (SEQ ID NO. 21) |
| | Reverse | ATCATGTAGAGCTCAAAGTTCCA (SEQ ID NO. 22) |
| Rarb | Forward | TTTCTCTGATGGCCTTACACTAA (SEQ ID NO. 23) |
| | Reverse | AGATTAAACAGATGGCACTGAGA (SEQ ID NO. 24) |

TABLE 3-continued

| Gene | | Mouse primer (5'→3') |
|---|---|---|
| GAPDH | Forward | ATAGCTGATGGCTGCAGGTT (SEQ ID NO. 25) |
| | Reverse | AATCTCCACTTTGCCACTGC (SEQ ID NO. 26) |

Figure 1B:
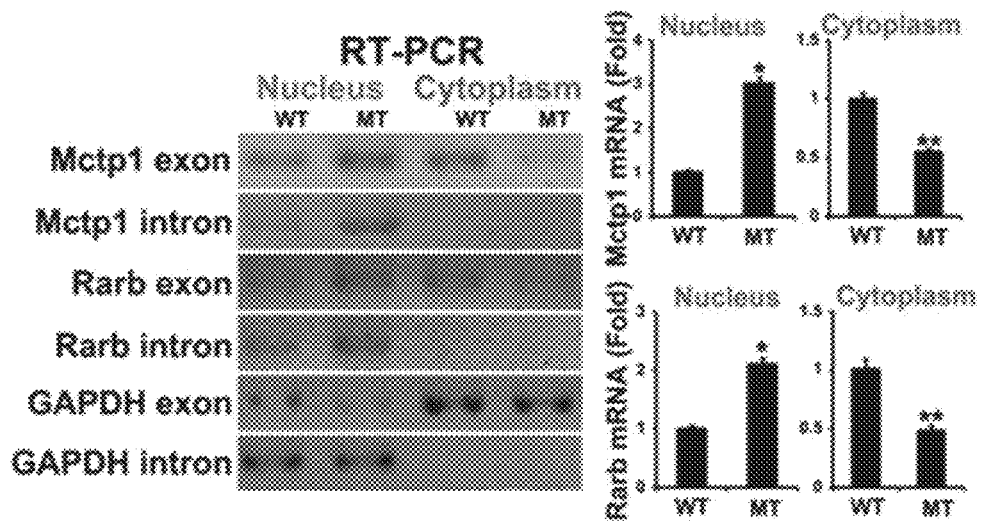
Figure 1C:
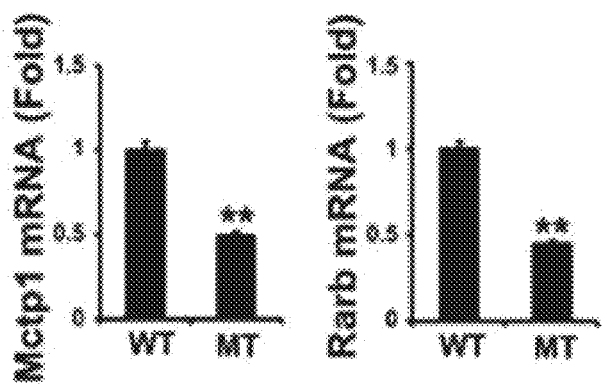
Figure 1D:
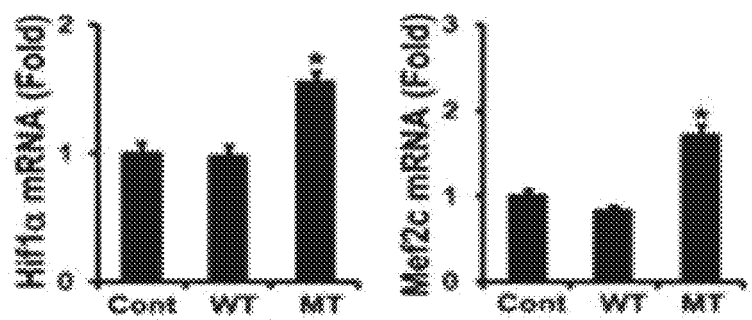

As a result, as illustrated in FIGS. 1A to 1D, it was confirmed that Hif1α and Mef2c regulated by Hif1α increase in nuclei and cytoplasm of mtNSC-34 cells (FIG. 1A). In addition, levels of Mctp1 known as relating to calcium signaling and Rarb relating to cell differentiation are changed in mtNSC-34 cells, and particularly, Mctp1 and Rarb mRNA were upregulated in the nuclei but were prominently downregulated in the cytoplasm (FIGS. 1A and 1B). In addition, it was confirmed that Hif1α and Mef2c mRNA expression levels were increased and Mctp1 and Rarb mRNA expression levels were reduced in mtNSC-34 cells (FIGS. 1C and 1D).

From the above results, it was confirmed that SOD1 mutations upregulated Hif1α and Mef2c and downregulated Mctp1 and Rarb, and particularly, that Mctp1 and Rarb were post-transcriptionally regulated in the cytoplasm.

<Example 3> Confirming Influence of SOD1 Mutation on Cells in SOD1 Mutant Motor Neurons In order to identify the influence of SOD1 mutations on cells, intracellular calcium signaling, cell differentiation, and apoptosis change were observed in mtNSC-34 cells.

Figure 2A:
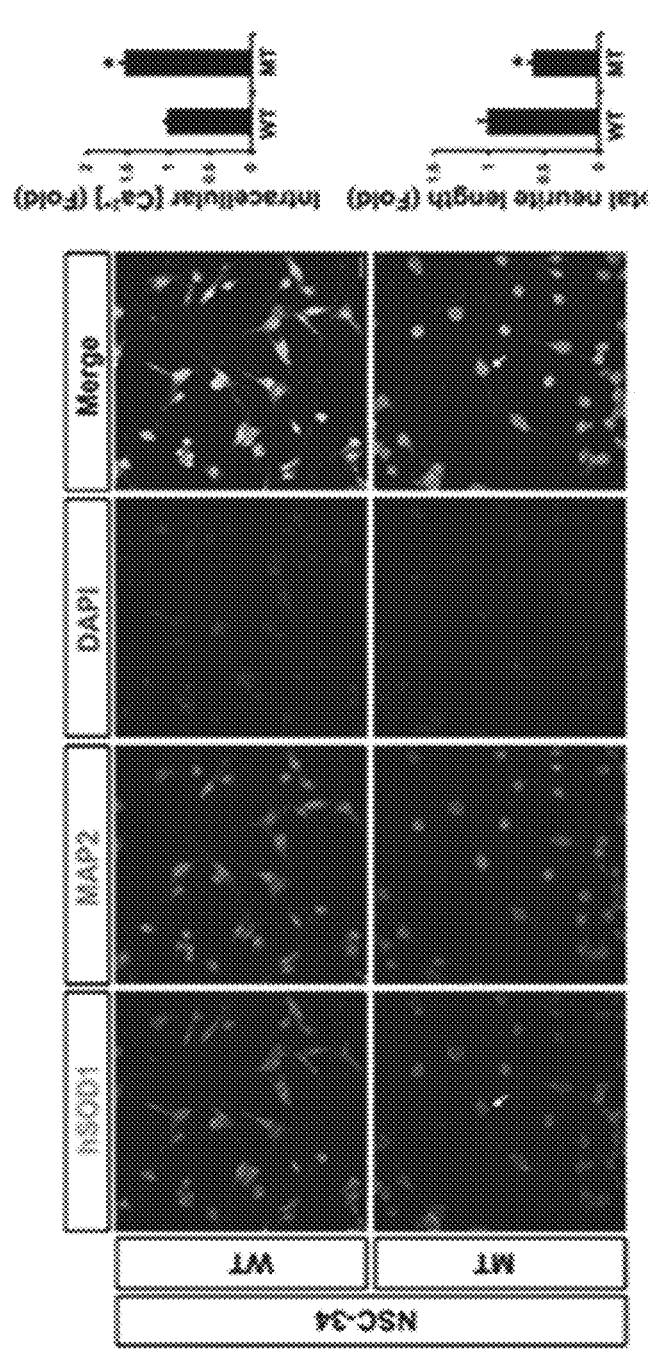
FIGS. 2A to 2D are diagrams confirming intracellular calcium signaling, cell differentiation, and apoptosis changes in mtNSC-34 cells according to an example of the present invention, wtNSC-34 cells, and motor neurons (NSC-34 cont cells) expressing mouse SOD1.

Since Mctp1 is known to be involved in calcium signaling, intracellular $Ca^{2+}$ analysis was performed in order to identify the influence of Mctp1 expression changes by SOD1 mutation on intracellular calcium signaling. Specifically, each of the mtNSC-34 cells and the wtNSC-34 cells obtained in Example <1-1> was treated in 96-well plates in $4 \times 10^4$ to $8 \times 10^4$ cells/well and cultured for one day in a growth medium. After 48 hours, FLUOFORTE Dye-Loading Solution was treated to each well, and cultured at 37° C. for 45 minutes and at room temperature for 15 minutes. Subsequently, fluorescence was measured at 490/525 nm using a fluorimeter (FIG. 2A, right, top).

In addition, since Rarb is known to be involved in cell differentiation, axonal production analysis was performed to identify the influence of Rarb expression changes by SOD1 mutation on the cell differentiation. Specifically, each of the mtNSC-34 cells and wtNSC-34 cells obtained in Example <1-1> was treated in 96-well plates in $4 \times 10^4$ to $8 \times 10^4$ cells/well and cultured for one day in a growth medium. Subsequently, the axon production was confirmed after visualization by using immunofluorescence staining and confocal microscopy (FIG. 2A, right, bottom).

Figure 2B:
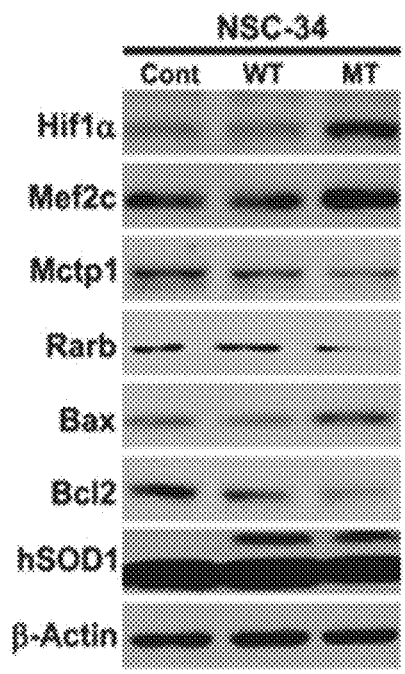
Figure 2C:
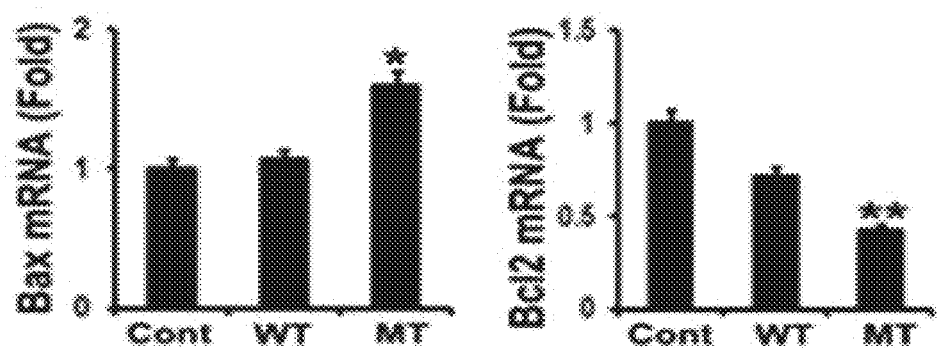

In addition, in order to identify the influence of the SOD1 mutation on the apoptosis, Western blotting and qRT-PCR were performed to confirm the expression of apoptosis-related factors and examine lactate dehydrogenase (LDH) release changes. Specifically, in order to perform Western blotting, mtNSC-34 cells, wtNSC-34 cells, and NSC-34 cont cells obtained in Example <1-1> were lysed by treating a lysis buffer (10 mM of Tris of pH 7.4, 1 mM of EDTA of pH 8.0, 500 mM of NaCl, and 0.5% of TritonX-100) for 30 minutes in ice, and protein lysates of the cells were electrophoresed on SDS-PAGE and then transferred to nitrocellulose membranes (PALL Life Sciences). Subsequently, a mouse anti-Hif1α antibody (NOVUS), a rabbit anti-Mef2c antibody (LSBio), a mouse anti-Mctp1 antibody (abcam), a rabbit anti-Rarb antibody (LSBio), a rabbit anti-Bax antibody (Cell signaling), a rabbit anti-Bcl2 antibody (abcam), and mouse anti-β-actin (Millipore) and rabbit anti-SOD1 (Enzo) antibodies were treated with primary antibodies, the HRP-conjugated secondary antibody was attached to the primary antibody attached to the membrane, and this was confirmed by using ECL (Pierce chemical co, USA) (FIG. 2B). In addition, RNA was extracted from each of mtNSC-34 cells, wtNSC-34 cells, and NSC-34 cont cells by the same method as described in <Example 2>, and qRT-PCR was performed by using the primers of Table 4 below (FIG. 2C).

TABLE 4

| Gene | | Mouse primer (5'→3') |
|---|---|---|
| Bax | Forward | AAGCTGAGCGAGTGTCTCCG (SEQ ID NO. 27) |
| | Reverse | GGAGGAAGTCCAGTGTCCAG (SEQ ID NO. 28) |
| Bcl2 | Forward | AACCCAATGCCCGCTGTGCA (SEQ ID NO. 29) |
| | Reverse | ACCGAACTCAAAGAAGGCCACAA (SEQ ID NO. 30) |

Figures 2D, 3A, 3B:
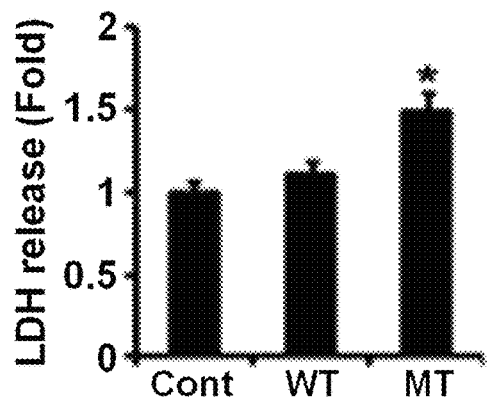
FIGS. 3A to 3D are diagrams confirming miR-18b as target miRNA that regulates Hif1α and miR-206 as target miRNA that controls Mctp1 and Rarb.

In addition, in order to confirm changes in lactate dehydrogenase (LDH) release, cell culture media of mtNSC-cells and wtNSC-34 cells obtained in Example <1-1> were harvested, centrifuged to obtain a supernatant, and moved to 96-well plates. The same amounts of LDH assay substrates (SIGMA), enzymes, and dye solutions were mixed. Half the volume of the mixture was added to 1 volume of the media supernatant. After reaction at room temperature for 30 minutes, the reaction was terminated by adding 1/10 volume of 1 N HCl to each well. Subsequently, the absorbance was then measured at a wavelength of 490 nm/690 nm by using a spectrophotometer (FIG. 2D). As a result, it is confirmed that, as illustrated in FIGS. 2A to 2D, intracellular $Ca^{2+}$ levels were increased in mtNSC-34 cells, and the total neurite growth was significantly reduced with the aggregation of SOD1 (G93A) protein (FIG. 2A). In addition, it was confirmed that, in mtNSC-34 cells, the protein levels of Hif1α and Mef2c were significantly increased and those of Mctp1 and Rarb were significantly reduced (FIG. 2B). In addition, the protein and mRNA levels of Bax in mtNSC-34 cells are increased, the protein and mRNA levels of Bcl2 are reduced (FIGS. 2B and 2C), and LDH release is increased (FIG. 2D), confirming that apoptosis is induced.

From the above results, it was confirmed that apoptosis was induced by SOD1 mutation and Mctp1 and Rarb levels were downregulated, and each caused changes in calcium signaling and cell differentiation.

<Example 4> Confirming of Target miRNA Regulating Hif1α, Mef2c, Mctp1, and Rarb miRNA is well-known as one of the most representative post-transcriptional regulators. Accordingly, as it is confirmed that Hif1α and Mef2c were upregulated and Mctp1 and Rarb were downregulated in mtNSC-34 cells, in order to identify miRNAs capable of regulating Hif1α, which is a higher regulator of Mef2c, and miRNAs capable of regulating Mctp1 and Rarb, TargetScan analysis was performed.

Specifically, analysis was performed by using miRNA having common sequence with Hif1α and miRNA having common sequence with Mctp1 and Rarb with TargetScan (http://www.targetscan.org) (FIGS. 3A and 3B).

Figure 3C:
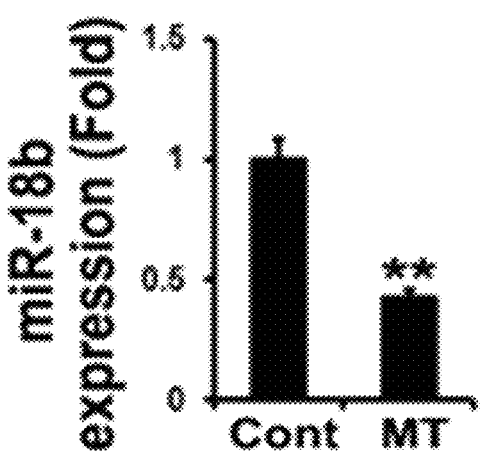
Figure 3D:
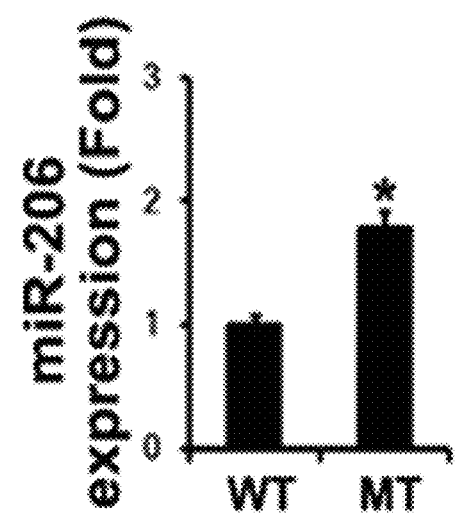

Also, in order to confirm expression changes of target miRNA confirmed in mtNSC-34 cells and wtNSC-34 cells with TargetScan, RNA was extracted from each of mtNSC-34 cells, wtNSC-34 cells, and NSC-34 cont cells by the same method as the method described in <Example 2>, and qRT-PCR was performed by using primers (GenoSensor) respectively for mmu-miR-18b and mmu-miR-206 (FIGS. 3C and 3D).

As a result, as illustrated in FIGS. 3A and 3B, it was confirmed that miR-206 can be a post-transcriptional regulator of Mctp1 and Rarb (FIG. 3A), and it was confirmed that miR-206 is significantly upregulated in mtNSC-34 cells (FIG. 3C). In addition, it was confirmed that miR-18b can target the Hif1α (FIG. 3B), and it was confirmed that miR-18b was significantly reduced in mtNSC-34 cells (FIG. 3D).

Since it is known that Mef2c acts as a transcriptional regulator of miR-206, the above results confirmed that SOD1 mutation causes miR-18b regulation disorder in which miR-18b expression is reduced, and Hif1α, Mef2c, miR-206, Mctp1, and Rarb expression can be sequentially regulated by miR-18b regulation disorder.

<Example 5> Confirming Hif1α Regulation and Apoptosis Changes by miR-18b

<5-1> Confirming Hif1α Upregulation and Apoptosis Induction by miR-18b Expression Suppression In order to identify whether miR-18b regulation disorder by SOD1 mutation relates to downstream mechanism regulation and apoptosis, miR-18b was reduced in wtNSC-34 cells by using a locked nucleic acid inhibitor (LNA) method, Western blotting and qRT-PCR were performed to confirm the expression of related factors and to confirm apoptosis changes.

Figure 4A:
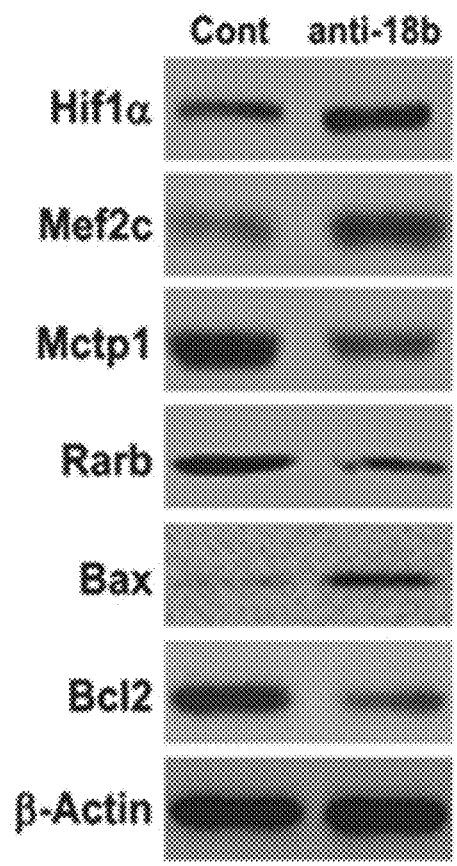
FIGS. 4A to 4K are diagrams confirming Hif1α, Mef2c, Mctp1, Rarb, and miR-206 expression changes and LDH release change in NSC-34 cont cells in which miR-18b expression is reduced according to an example of the present invention, and confirming apoptosis changes in a neuron stem cell (NSC) in which miR-18b expression is reduced according to an example of the present invention.
Figure 4B:
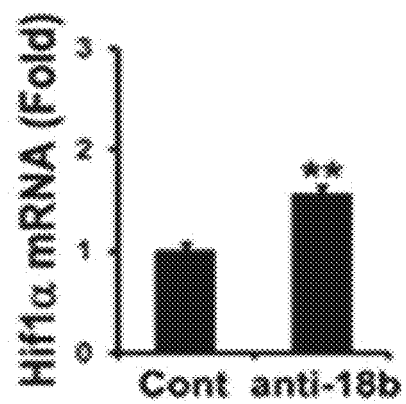
Figure 4C:
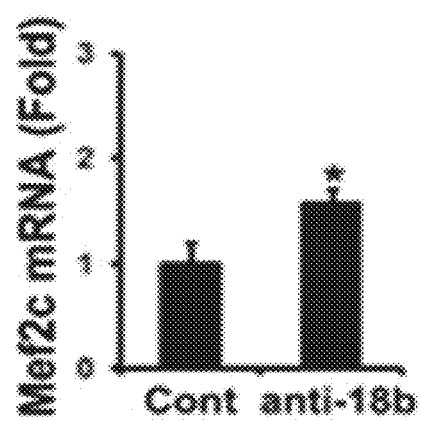
Figure 4D:
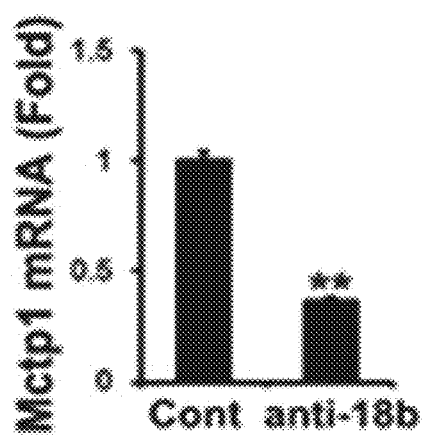
Figure 4E:
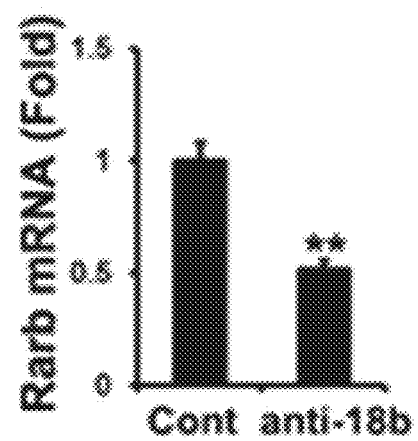
Figure 4F:
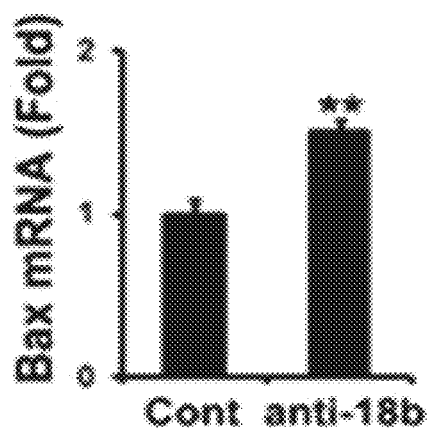
Figure 4G:
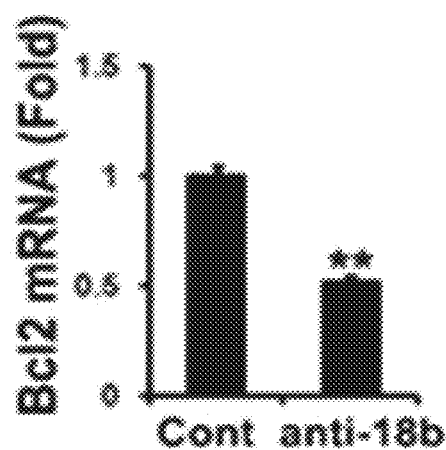
Figure 4H:
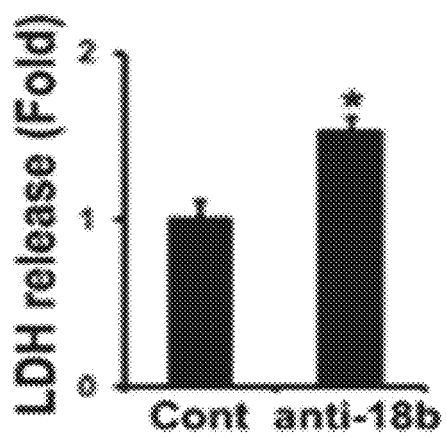

Specifically, LNA (anti-18b, COSMO GENETECH Co., Ltd.) of miR-18b was transfected into NSC-34 cont cells obtained in Example <1-1> by using a RNAiMax transfection reagent (Invitrogen) according to the procedures of the manufacturer and was collected after 48 hours. Subsequently, by the same method as the method described in <Example 2> to <Example 4>, Western blotting (FIG. 4A), qRT-PCR (FIGS. 4B to 4G, 4I, and 4J), and LDH release analysis (FIG. 4H) were performed. NSC-34 cont cells were used as a control.

Also, in order to confirm apoptosis changes, Annexin V-FITC and PI analysis were further performed. Specifically, NSC cultured in Example <1-2> was seeded on 6-well tissue culture plates and treated with LNA (anti-18b) of miR-18b, attached cells were isolated by TripleExpress after 48 hours, and a culture medium was added to inactivate trypsin. Subsequently, centrifugation was performed at 1,500×g for 5 minutes and the supernatant was removed. Cells were stained with Annexin V-FITC and PI according to the procedures of the manufacturer by using Annexin-V-FITC and PI Apoptosis Detection Kit (BD Biosciences). After staining, the cells were analyzed by using FACSCalibur (BD Biosciences). Fluorescence was analyzed by using green or red channels, and data were analyzed using Flowwing Software (Version 2.5.1, University of Turku, Finland) (FIG. 4K).

Figure 4I:
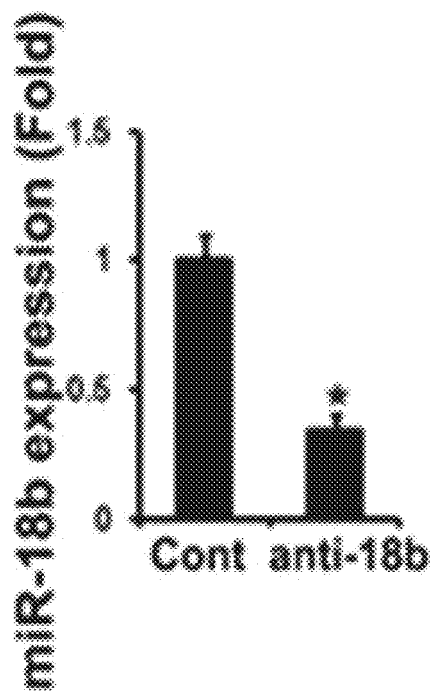
Figure 4J:
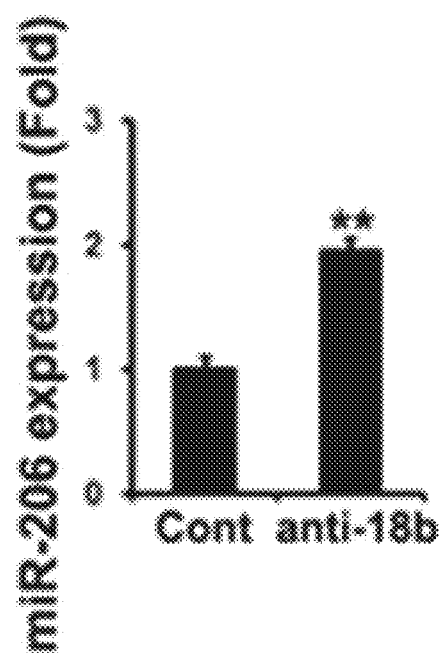
Figure 4K:
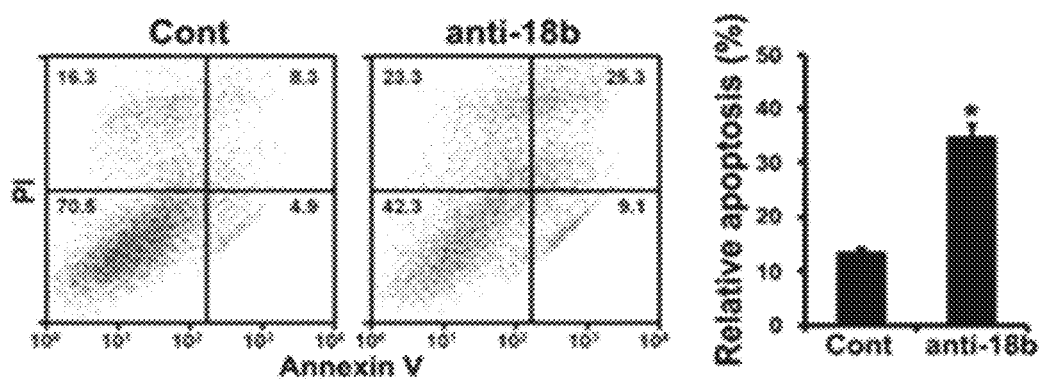

As a result, as illustrated in FIGS. 4A to 4J, it was confirmed that LNA (anti-18b) of miR-18b increased protein and mRNA expression of Hif1α and Mef2c, and reduced protein and mRNA expression of Mctp1 and Rarb (FIGS. 4A to 4E). In addition, it was confirmed that miR-206 is rapidly induced under miR-18b deficiency (FIGS. 4I and 4J). In addition, it was confirmed that apoptosis was increased under miR-18b deficiency (FIGS. 4A, 4F to 4H, and 4K).

From the above results, it was confirmed that miR-18b regulation disorder by SOD1 mutation upregulated Hif1α and induced apoptosis by downstream mechanism, and thus miR-18b can be used as target miRNA for ALS diagnosis.

<5-2> Confirming Hif1α Downregulation and Apoptosis Suppression by miR-18b Overexpression In order to identify whether overexpression of miR-18b can suppress Hif1α upregulation and apoptosis caused by SOD-1 mutation, miR-18b was overexpressed in mtNSC-34 cells, and Western blotting and qRT-PCR were performed to confirm the expression of related factors. In addition, intracellular calcium signaling, cell differentiation, and apoptosis changes were confirmed.

Specifically, cDNA was obtained from NSC-34 cont cells obtained in Example <1-1>, the cDNA was used as a template, and PCR was performed by using a primer of Table 5 to amplify miR-18b. The amplified miR-18b PCR product was cloned into a pCDNA3 vector (Invitrogen) having BamH I and Xho I (NEW ENGLAND BioLabs) restriction enzyme sites to prepare a miR-18b plasmid construct.

TABLE 5

| Gene | | Mouse primer (5'→3') |
|---|---|---|
| miR-18b | Forward | CGCGGATCCACCATGGTGATTTAATCAGA (SEQ ID NO. 31) |
| | Reverse | CCGCTCGAGCCGTTCAAATCATTTCTCAA (SEQ ID NO. 32) |

Figure 5A:
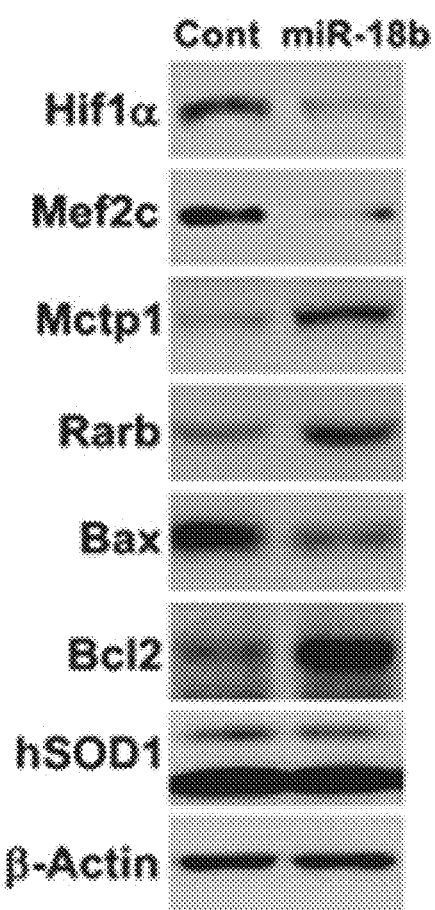
FIGS. 5A to 5H are diagrams confirming Hif1α, Mef2c, Mctp1, Rarb, and miR-206 expression changes, intracellular calcium signaling, cell differentiation, and apoptosis changes in mtNSC-34 cells in which miR-18b expression is increased according to an example of the present invention.
Figure 5B:
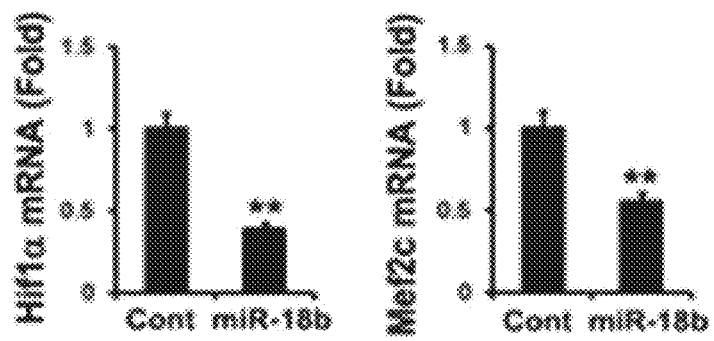
Figure 5C:
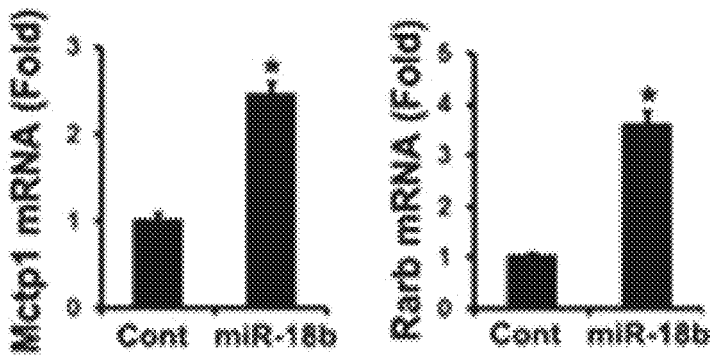
Figure 5D:
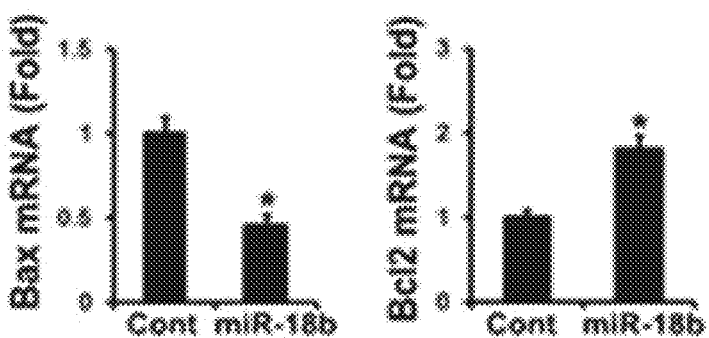
Figure 5E:
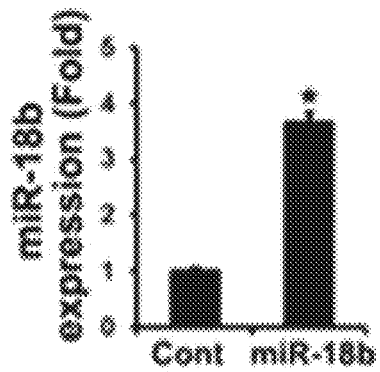
Figure 5F:
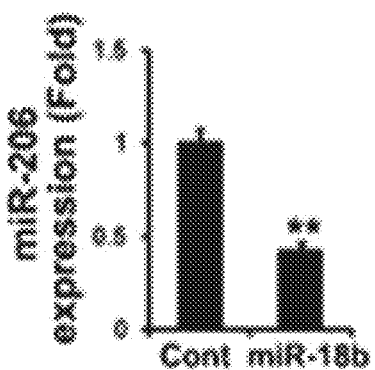
Figure 5G:
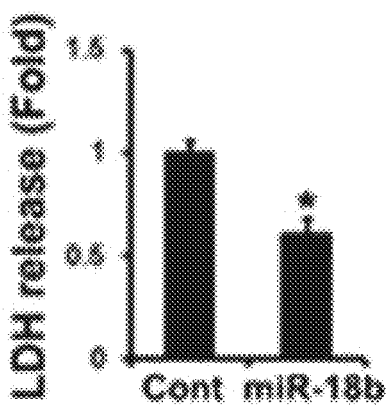
Figure 5H:
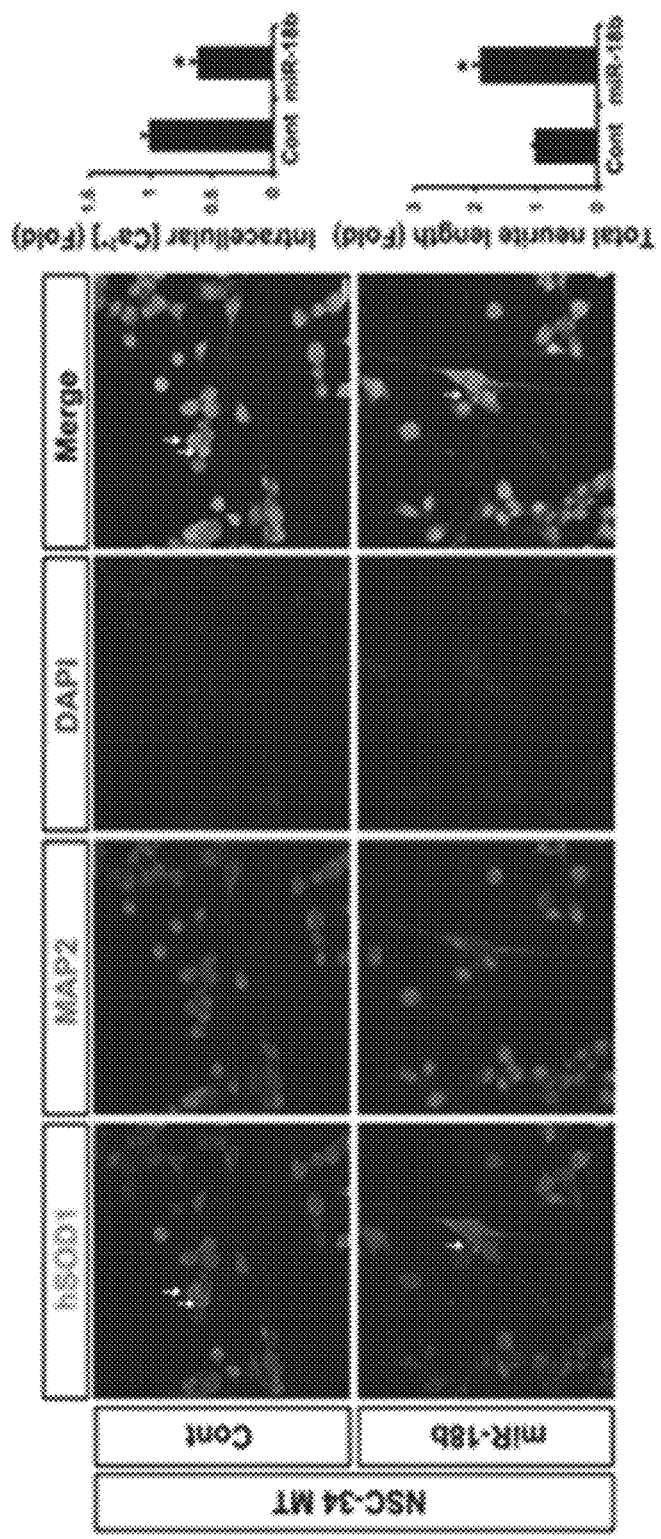

In order to prepare mtNSC-34 cells overexpressing miR-18b, the miR-18b plasmid construct was transfected into mtNSC-34 cells according to the procedures of the manufacturer by using Lipofectamine 2000 (Invitorgen) and was collected after 48 hours. Western blotting (FIG. 5A), qRT-PCR (FIGS. 5B to 5F), intracellular $Ca^{2+}$ analysis (FIG. 5H, right, top), axon production analysis (FIG. 5H, right, bottom), and LDH release analysis (FIG. 5G) were performed by the same method as the method described in <Example 2> to <Example 4>. mtNSC-34 cells were used as a control. As a result, as illustrated in FIGS. 5A to 5H, it was confirmed that miR-18b overexpression in mtNSC-34 cells reduced Hif1α and Mef2c expression but increased Mctp1 and Rarb expression (FIGS. 5A to 5C). In addition, it was confirmed that miR-206 was downregulated by overexpressed miR-18b (FIGS. 5E and 5F). In addition, it was confirmed that the overexpressed miR-18b suppressed apoptosis in mtNSC-34 cells (FIGS. 5A, 5D, and 5G). Meanwhile, it was confirmed that, though SOD1 aggregation was observed in mtNSC-34 cells, the overexpressed miR-18b reduced the intracellular $Ca^{2+}$ level and activated neuron differentiation (FIG. 5H).

From the above results, it was confirmed that the overexpression of miR-18b suppresses apoptosis caused by SOD-1 mutation, and miR-18b can be used for ALS prevention and treatments.

<Example 6> Confirming Mef2c Regulation and Apoptosis Changes by Hif1α

Since it was confirmed that miR-18b acts as target miRNA of Hif1α and miR-18b regulation disorder upregulates Hif1α expression, in order to identify the mechanism after upregulation of Hif1α in a miR-18b pathway, Hif1α expression was reduced in mtNSC-34 cells by using RNAi, and then Western blotting and qRT-PCR were performed to confirm expression and apoptosis changes of related factors.

Specifically, mouse siHif1α (5'-AAGCAUUUCUCU-CAUUUCCUCAUGG-3', SEQ ID NO: 33) prepared by COSMO GENETECH Co., Ltd. upon request was transfected into the mtNSC-34 cells obtained in Example <1-1> by using a RNAiMax transfection reagent (Invitrogen) according to the procedure of the manufacturer and was collected after 48 hours. Subsequently, Western blotting (FIG. 6A), qRT-PCR (FIGS. 6B to 6H), and LDH release analysis (FIG. 6I) were performed by the same method as the method described in <Example 2> to <Example 4>. mtNSC-34 cells were used as a control.

Figure 6A:
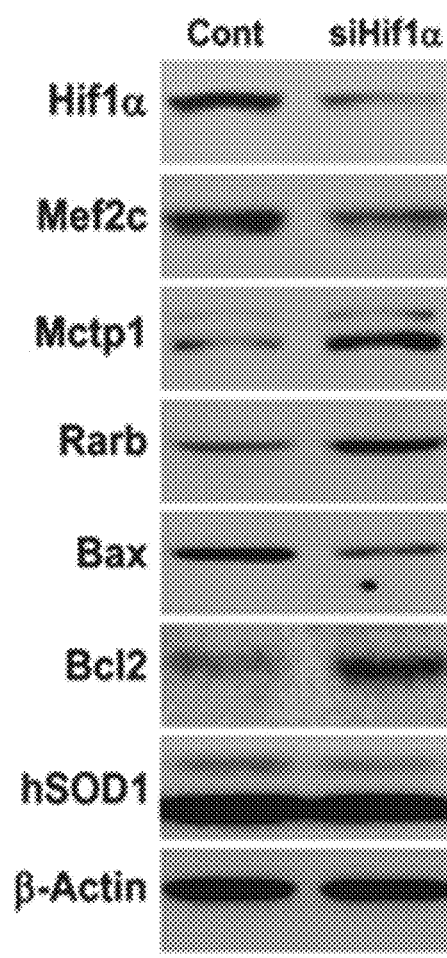
FIGS. 6A to 6I are diagrams confirming Mef2c, Mctp1, Rarb, and miR-206 expression changes and apoptosis changes in mtNSC-34 cells in which Hif1α expression is reduced according to an example of the present invention.
Figure 6B:
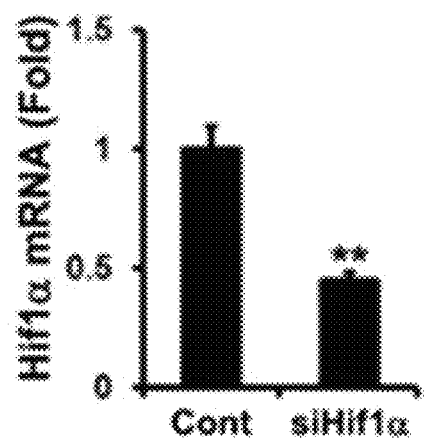
Figure 6C:
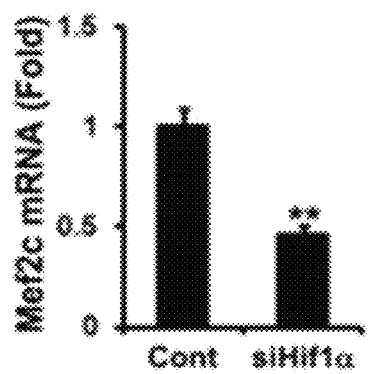
Figure 6D:
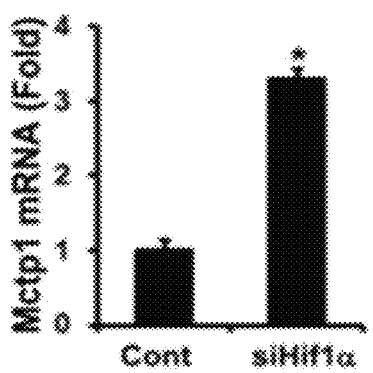
Figure 6E:
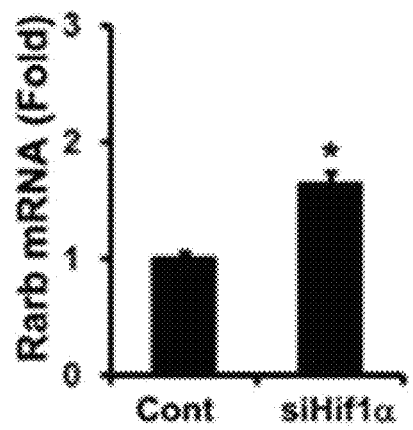
Figure 6F:
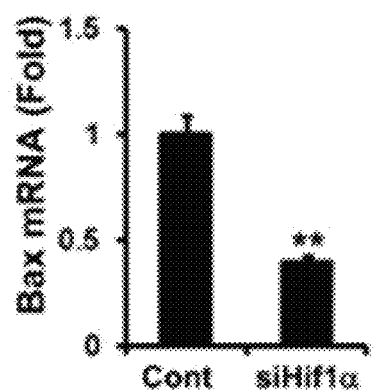
Figure 6G:
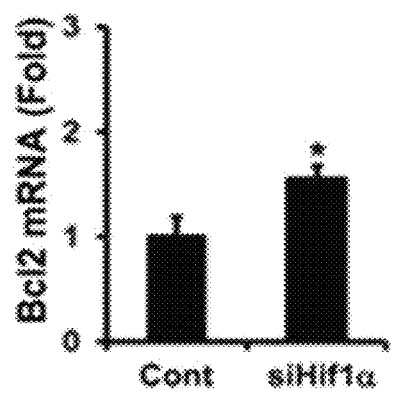
Figure 6H:
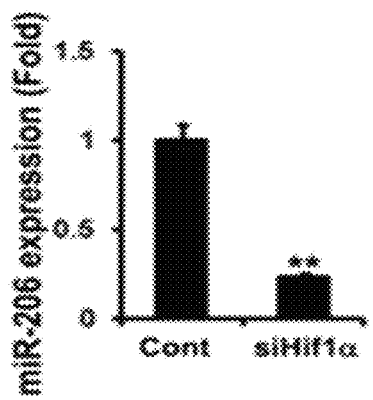
Figure 6I:
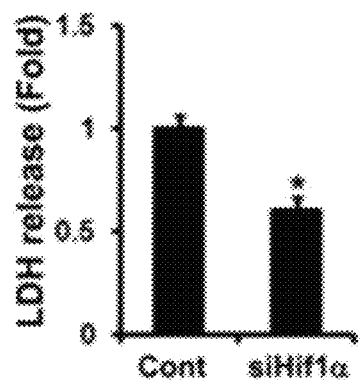

As a result, as illustrated in FIGS. 6A to 6I, it was confirmed that, Mef2c protein and mRNA levels were reduced in mtNSC-34 cells under Hif1α deficiency (FIGS. 6A to 6C), and Mctp1 and Rarb protein and mRNA levels were increased (FIGS. 6A, 6D, and 6E). In addition, it was confirmed that the Mef2c expression suppression by Hif1α deficiency reduced miR-206 levels (FIG. 6H). Also, it was confirmed that apoptosis was suppressed in the Hif1α deficiency state (FIGS. 6F, 6G, and 6I).

From the above results, it was confirmed that miR-18b regulation disorder by SOD1 mutation induced upregulation of Hif1α and upregulated Hif1α upregulated Mef2c to induce the apoptosis.

<Example 7> Confirming Post-Transcriptional Regulation and Apoptosis Changes in Mctp1 and Rarb by miR-206

<7-1> Confirming Mctp1 and Rarb Downregulation and Apoptosis Induction by miR-206 Overexpression In order to identify the role of miR-206 under the SOD1 mutation condition, luciferase reporter analysis was performed by using 3'UTR of Mctp1 and Rarb in NSC-34 cont cells in which miR-206 was overexpressed. In addition, Western blotting and qRT-PCR were performed to confirm the expression of related factors. Also, intracellular calcium signaling, cell differentiation, apoptosis changes were confirmed.

Specifically, cDNA was obtained from NSC-34 cont cells obtained in Example <1-1>, the cDNA was used as a template, and PCR was performed by using a primer of Table 7 to amplify miR-206. The miR-206 PCR product was cloned into a pCDNA3 vector (Invitrogen) having BamH I and Xho I (NEW ENGLAND BioLabs) restriction enzyme sites to prepare a miR-206 plasmid construct. In addition, PCR was performed by using a primer of Table 6 to amplify each 3'UTR of Mctp1 and Rarb. Each of the amplified Mctp1 3'UTR and Rarb 3'UTR PCR products were cloned into pmirGLO double-luciferase vectors (Promega) having Xho I and Xba I (NEW ENGLAND BioLabs) restriction enzyme sites to prepare Mctp1 3'UTR plasmid construct and Rarb 3'UTR plasmid constructs.

TABLE 6

| Gene | | Mouse primer (5'→3') |
|---|---|---|
| miR-206 | Forward | CGCGGATCCATTCTTCACACTTCTCACTT (SEQ ID NO. 34) |
| | Reverse | CCGCTCGAG ACGAAGAAGTCAACAGCATA (SEQ ID NO. 35) |
| Mctp1 3' UTR | Forward | CCGCTCGAGAAAGCTTGAATAATAGAAAT (SEQ ID NO. 36) |
| | Reverse | CTAGTCTAGAATACATGGGTTTTTGTTTG (SEQ ID NO. 37) |

TABLE 6-continued

| Gene | | Mouse primer (5'→3') |
|---|---|---|
| Rarb 3' UTR | Forward | CCGCTCGAGAACGTGTAATTACCTTGAAA (SEQ ID NO. 38) |
| | Reverse | CTAGTCTAGACAAAGTCTTCAGAAACTTAA (SEQ ID NO. 39) |

Figure 7A:
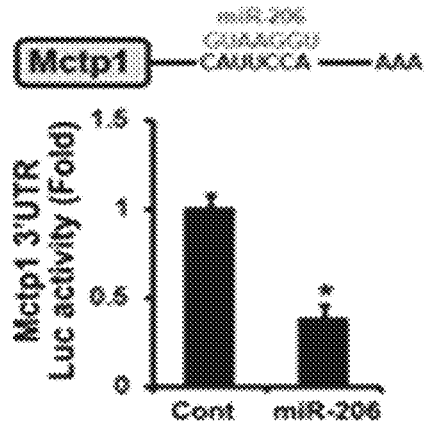
FIGS. 7A to 7F are diagrams confirming Mctp1 and Rarb expression changes in NSC-34 cont cells in which miR-206 expression is increased according to an example of the present invention.
Figure 7B:
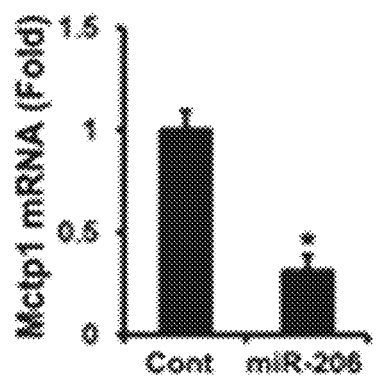
Figure 7C:
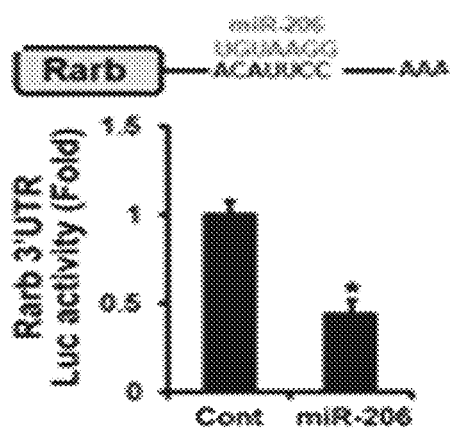
Figure 7D:
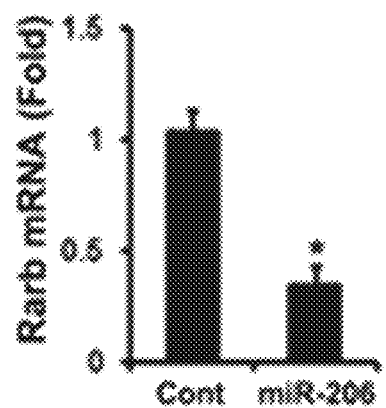
Figure 7E:
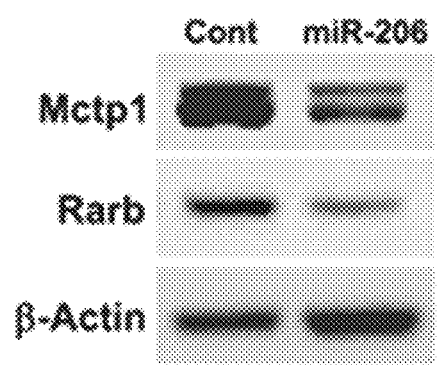
Figure 7F:
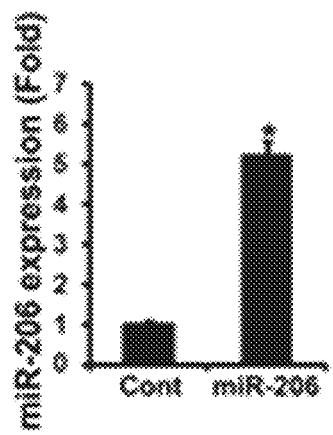
Figure 8A:
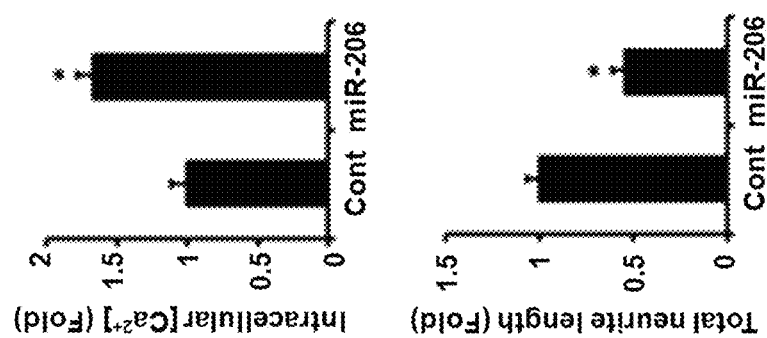
FIGS. 8A to 8E are diagrams confirming intracellular calcium signaling and cell differentiation in NSC-34 cont cells in which miR-206 expression is increased according to an example of the present invention and confirming apoptosis changes in each of NSC-34 cont cells in which miR-206 expression is increased according to an example of the present invention and NSC.
Figure 8A:
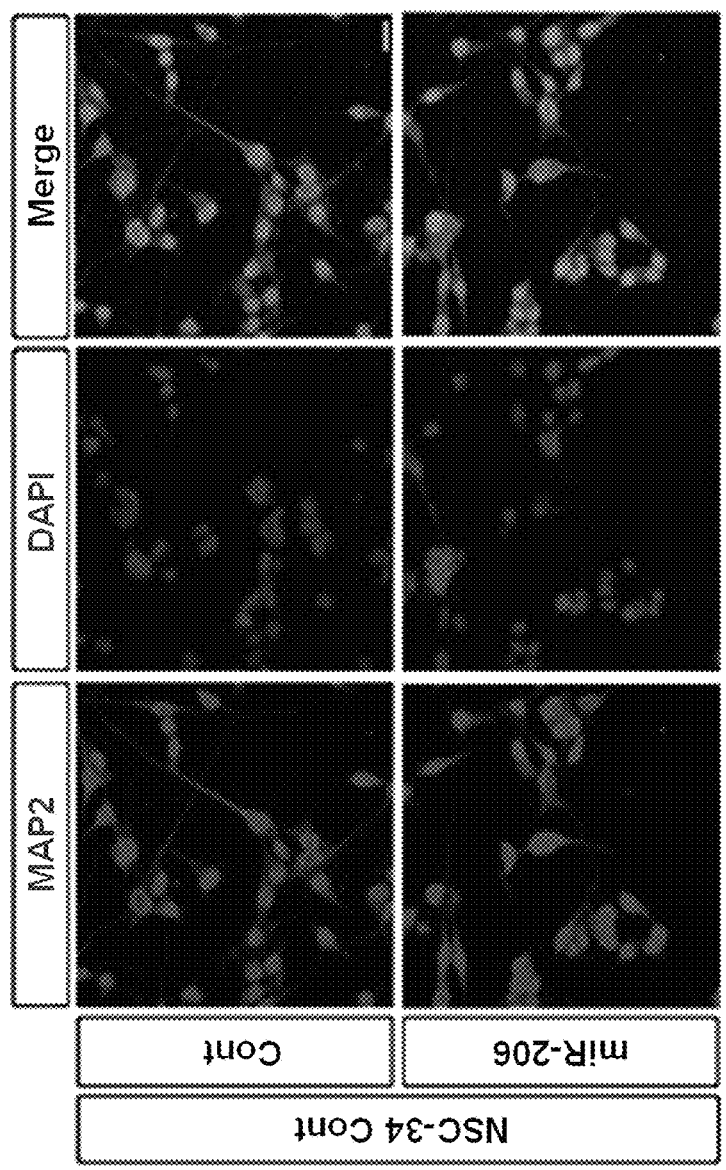
Figure 8B:
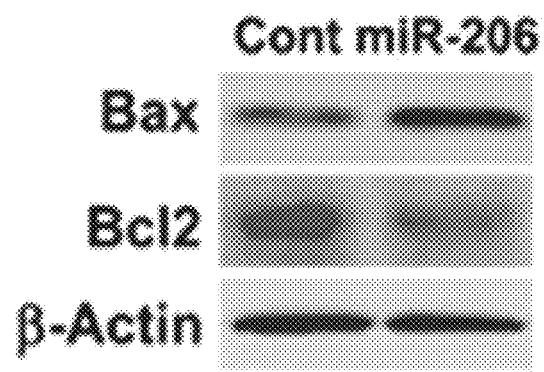
Figure 8C:
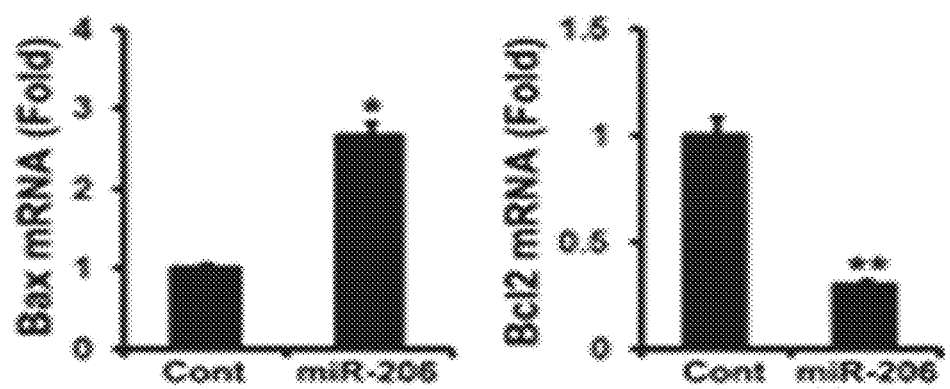
Figure 8D:
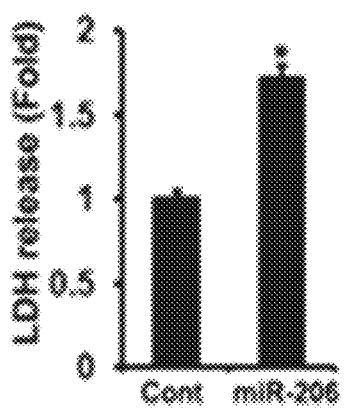
Figure 8E:
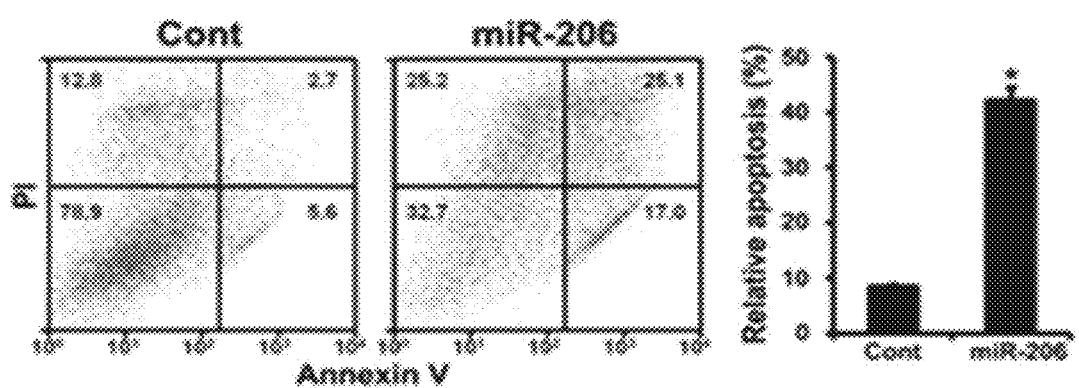

Subsequently, the miR-206 plasmid constructs, the Mctp1 3'UTR plasmid constructs, and the Rarb 3'UTR plasmid constructs were transfected into NSC-34 cont cells according to the procedure of the manufacturer by using Lipofectamine 2000 (Invitorgen) and collected after 48 hours to measure luciferase activity (FIGS. 7A and 7C). In addition, Western blotting (FIG. 7E), qRT-PCR (FIGS. 7B, 7D, 7F, and 8C), intracellular $Ca^{2+}$ analysis (FIG. 8A, right, top), axon production analysis (FIG. 8A, right, bottom), and LDH release analysis (FIG. 8D) were performed by the same method as the method described in <Example 2> to <Example 4>. NSC-34 cont cells were used as a control. In addition, the miR-206 plasmid construct was transfected into NSC cultured in Example <1-2>, and Annexin-V-FITC and PI analysis (FIG. 8E) were performed by the same method as the method described in Example <5-1>. NSC was used as a control.

As a result, as illustrated in FIGS. 7A to 7F and 8A to 8E, it was confirmed that Mctp1 level was reduced and the intracellular $Ca^{2+}$ level was increased by the overexpressed miR-206. In addition, it was confirmed that Rarb level was reduced and neuron differentiation was suppressed by overexpressed miR-206 (FIGS. 7A to 7E, and 8A). Also, it was confirmed that apoptosis was induced by the overexpression of miR-206 (FIGS. 8B to 8E).

<7-2> Confirming Mctp1 and Rarb Upregulation and Apoptosis Suppression by miR-206 Expression Suppression In order to identify the role of miR-206 under SOD1 mutation condition, miR-206 expression was reduced in mtNSC-34 cells by using the LNA method, and Western blotting and qRT-PCR were performed to confirm the expression of related factors and confirm apoptosis changes.

Specifically, LNA (anti-206, COSMOGENTECH) of miR-206 was transfected into mtNSC-34 cells obtained in Example <1-1> by using a RNAiMax transfection reagent (Invitrogen) according to the procedure of the manufacturer and were collected after 48 hours. Subsequently, Western blotting (FIG. 9A), qRT-PCR (FIGS. 9B to 9E and 9G), and LDH release analysis (FIG. 9F) were performed by the same method as the method described in <Example 2> to <Example 4>. mtNSC-34 cells were used as a control.

Figure 9A:
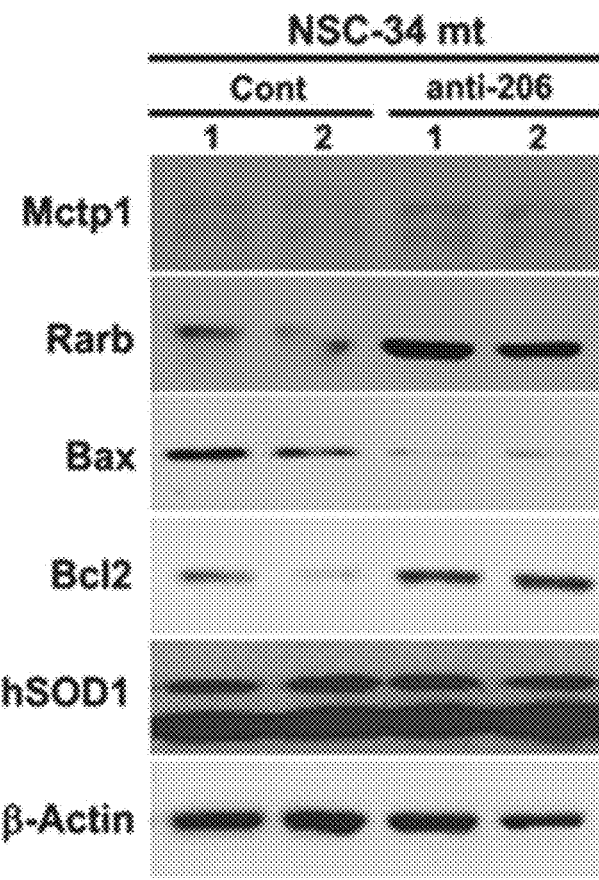
FIGS. 9A to 9G are diagrams confirming Mctp1 and Rarb expression changes and apoptosis changes in mtNSC-34 cells in which miR-206 expression is reduced according to an example of the present invention.
Figure 9B:
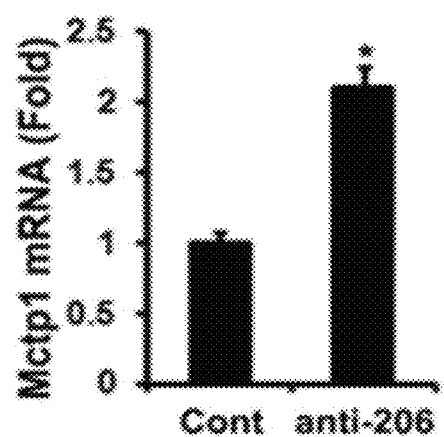
Figure 9C:
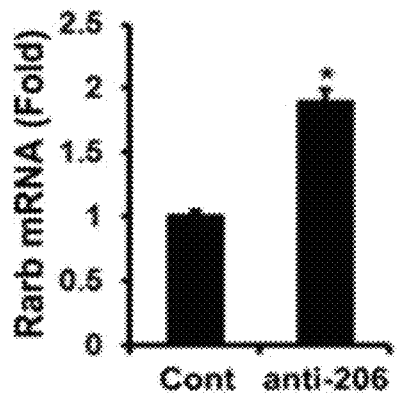
Figure 9D:
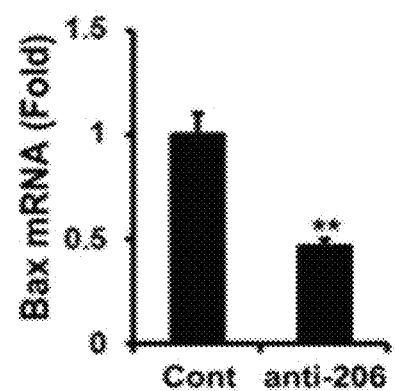
Figure 9E:
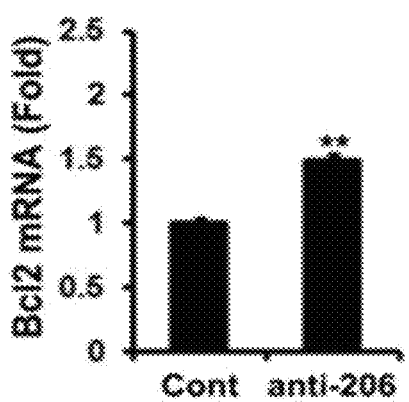
Figure 9F:
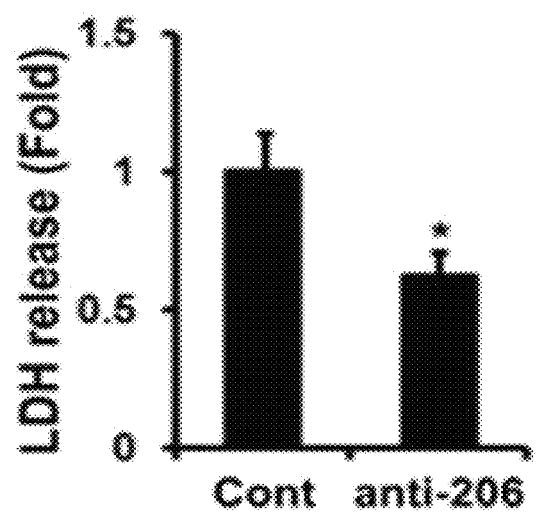
Figure 9G:
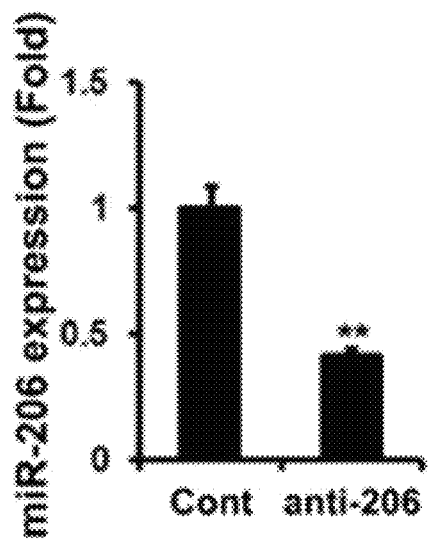

As a result, as illustrated in FIGS. 9A to 9G, it was confirmed that amounts of protein and mRNA of Mctp1 and Rarb were significantly increased in mtNSC-34 cells by the miR-206 expression suppression (FIGS. 9A to 9C). In addition, it was confirmed that apoptosis was suppressed by the miR-206 expression suppression (FIGS. 9D to 9F).

From the above results, it was confirmed that the miR-18b regulation disorder by SOD1 mutation induced the upregulation of Hif1α, the upregulated Hif1α upregulates Mef2c, Mef2c acts as an transcription regulatory factor of miR-206 to induce miR-206 expression, and miR-206 directly involved in post-transcriptional regulation of Mctp1 and Rarb, to induce apoptosis.

<Example 8> Confirming Influence of Post-Transcriptional Regulation of Mctp1 and Rarb on Cells <8-1> Confirming Apoptosis Induction by Reduction of Mctp1 and Rarb Expression From the above examples, it was confirmed that Hif1α expression was induced by the regulation disorder of miR-18b, Mef2c expression was induced by Hif1α, miR-206 expression was induced by Mef2c, and Mctp1 and Rarb were post-transcriptionally regulated by miR-206. Accordingly, in order to identify whether Mctp1 and Rarb deficiency directly induced apoptosis, Mctp1 and/or Rarb expression was reduced in the NSC-34 cont cells by using RNAi, and then Western blotting and qRT-PCR were performed to confirm the expression of related factors. In addition, intracellular calcium signaling, cell differentiation, and apoptosis changes were confirmed.

Figure 10A:
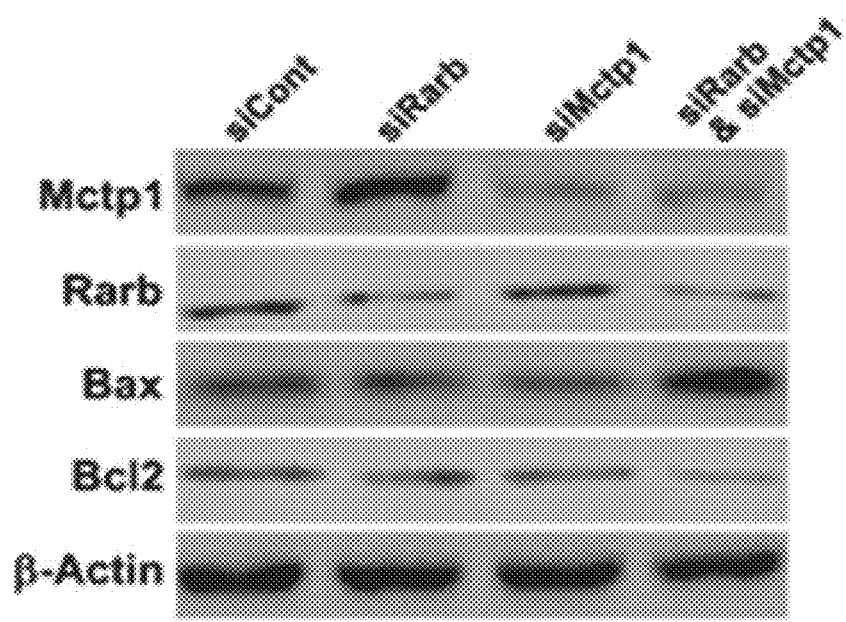
FIGS. 10A to 10D are diagrams confirming intracellular calcium signaling and cell differentiation changes in NSC-34 cont cells in which Mctp1 and/or Rarb expression are reduced according to an example of the present invention.
Figure 10B:
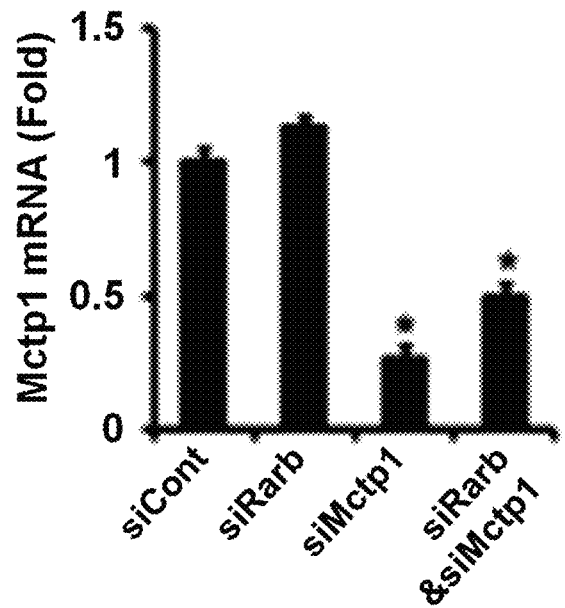
Figure 10C:
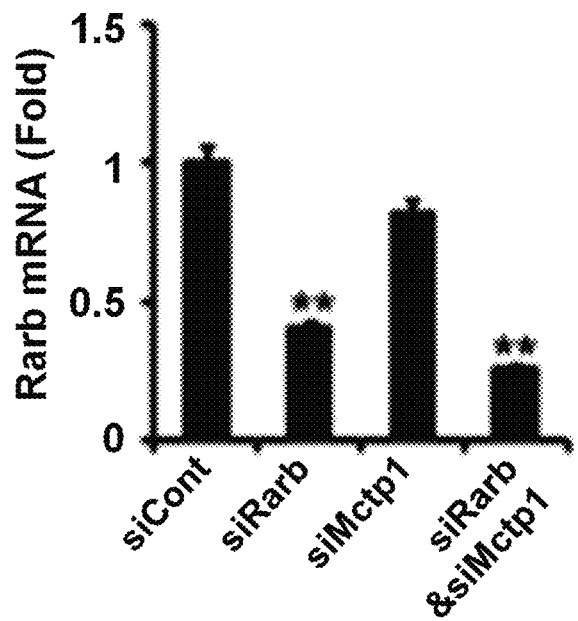
Figure 10D:
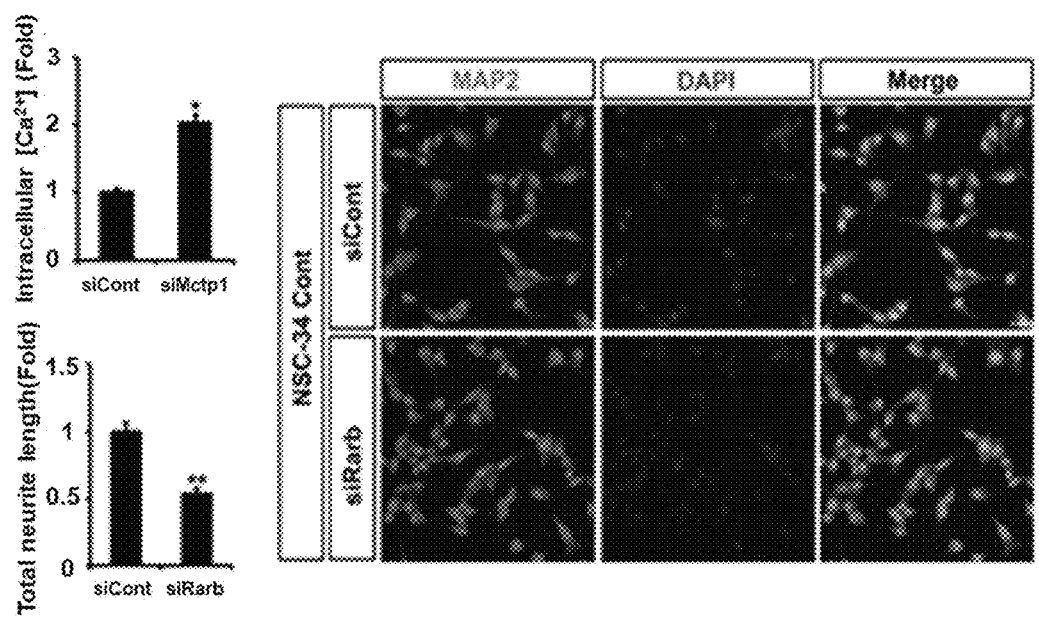
Figure 11A:
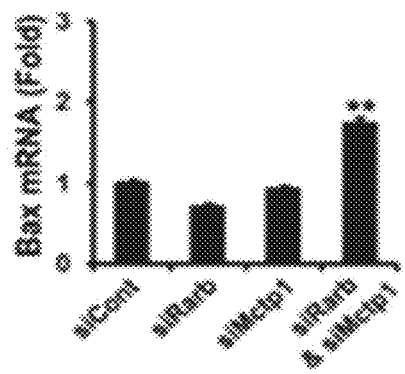
FIGS. 11A to 11D are diagrams confirming apoptosis changes in each of NSC-34 cont cells in which Mctp1 and/or Rarb expression are reduced according to an example of the present invention and neuron stem cells.
Figure 11B:
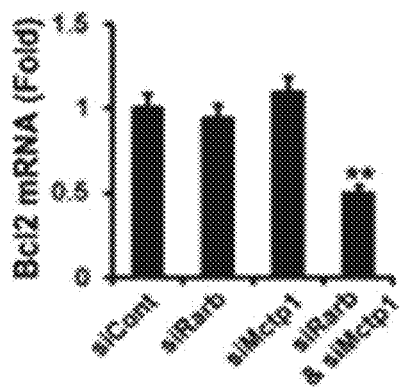
Figure 11C:
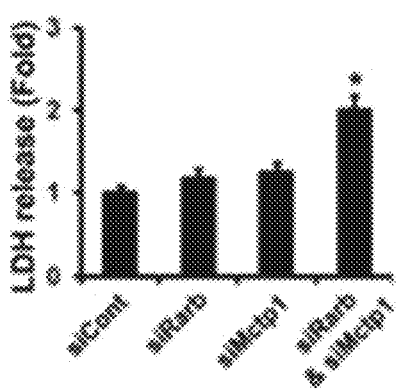

Specifically, mouse siMctp1 (5'-GCCACUAUAUAU-CAAGGUAUU-3', SEQ ID NO: 40) and/or mouse siRarb (5'-GGAGCCUUCAAAGCAGGAATT-3', SEQ ID NO: 41) prepared by COSMO GENETECH Co., Ltd. upon request were transfected into NSC-34 cont cells obtained in Example <1-1> according to the procedure of the manufacturer by using a RNAiMax transfection reagent (Invitrogen) and were collected after 48 hours. Subsequently, Western blotting (FIG. 10A), qRT-PCR (FIGS. 10B, 10C, 11A, and 11B), intracellular $Ca^{2+}$ analysis (FIG. 10D, left, top), axon production analysis (FIG. 10D, left, bottom), and LDH release analysis (FIG. 11C) were performed by the same method as the method described in <Example 2> to <Example 4>. NSC-34 cont cells were used as a control.

Figure 11D:
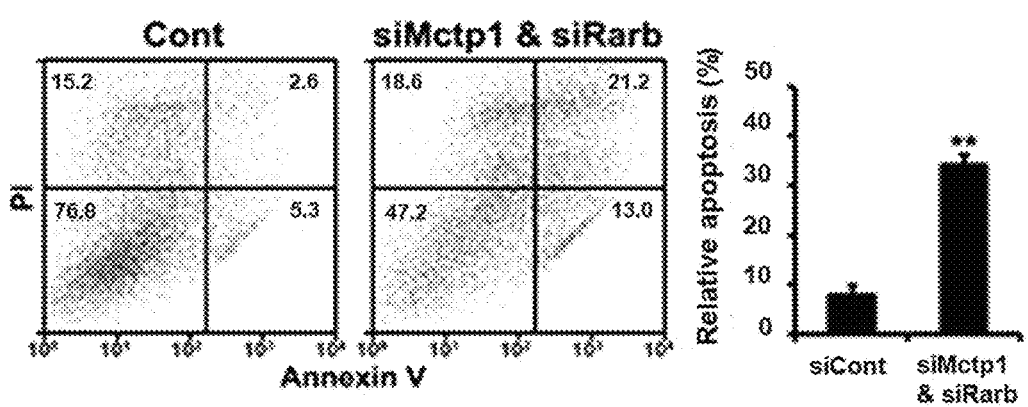

Also, the siMctp1 and the siRarb were transfected into NSC cultured in Example <1-2>, and Annexin-V-FITC and PI analysis (FIG. 11D) were performed by the same method as the method described in Example <5-1>. NSC was used as a control.

As a result, as illustrated in FIGS. 10A to 10D and 11A to 11D, it was confirmed that Mctp1 expression was suppressed to increase intracellular $Ca^{2+}$ concentration, but there was no influence on Bax and Bcl2 expression. In addition, it was confirmed the Rarb expression was suppressed to suppress the cell differentiation, but there was no significant change of Bax and Bcl2 expression. Meanwhile, when the Mctp1 and Rarb expression was simultaneously suppressed, it was confirmed that Bax expression was increased and Bxl2 expression was reduced, and LDH release was increased to induce apoptosis (FIGS. 10A to 10D, and 11A to 11D).

<8-2> Confirming Apoptosis Suppression by Increase of Mctp1 and Rarb Expression

In order to identify whether apoptosis was directly suppressed by the induction of Mctp1 and Rarb expression, Mctp1 and/or Rarb was overexpressed to mtNSC-34 cells, and Western blotting and qRT-PCR were performed to confirm expression of related factors. In addition, intracellular calcium signaling, cell differentiation, and apoptosis changes were confirmed.

Specifically, cDNA was obtained from the NSC-34 cont cells obtained from Example <1-1>, the cDNA was used as a template, PCR was performed by using the primer of Table 7 to amplify Mctp1 and Rarb. The amplified Mctp1 PCR product was cloned into mCherry C1 (Clontech) having a Hind III (NEW ENGLAND BioLabs) restriction enzyme site to prepare a Mctp1 plasmid construct. The amplified Rarb PCR product was cloned into eGFP N1 (Clontech) having Nhe I and Age I (NEW ENGLAND BioLabs) restriction enzyme sites to prepare a Rarb plasmid construct.

TABLE 7

| Gene | | Mouse primer (5'→3') |
|------|---|----------------------|
| Mctp1 | Forward | CCCAAGCTTATGTACCAGTTGGATATCACACTA (SEQ ID NO. 42) |
| | Reverse | CCCAAGCTTGCCAAGGTTGTTTTTTCTTCC (SEQ ID NO. 43) |
| Rarb | Forward | CCGCTAGCATGAGCACCAGCAGCCACGC (SEQ ID NO. 44) |
| | Reverse | CCACCGGTCTGCAGCAGTGGTGACTGAC (SEQ ID NO. 45) |

Figure 12A:
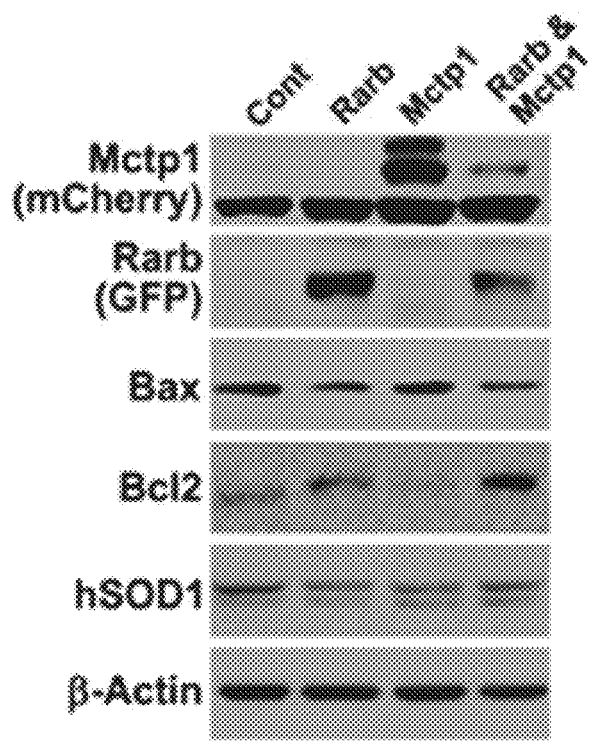
FIGS. 12A to 12G are diagrams confirming intracellular calcium signaling, cell differentiation, and apoptosis changes in mtNSC-34 cells in which Mctp1 and/or Rarb expression are increased according to an example of the present invention.
Figure 12B:
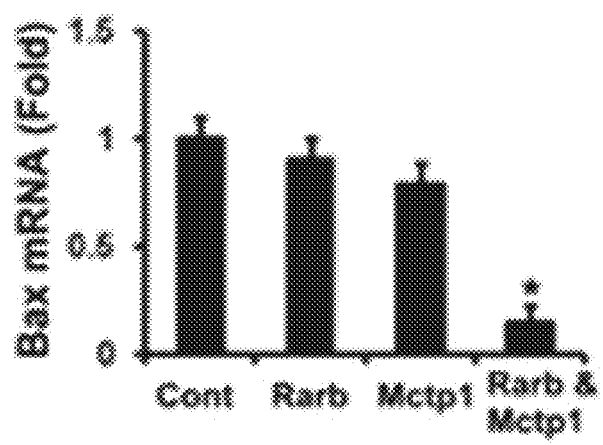
Figure 12C:
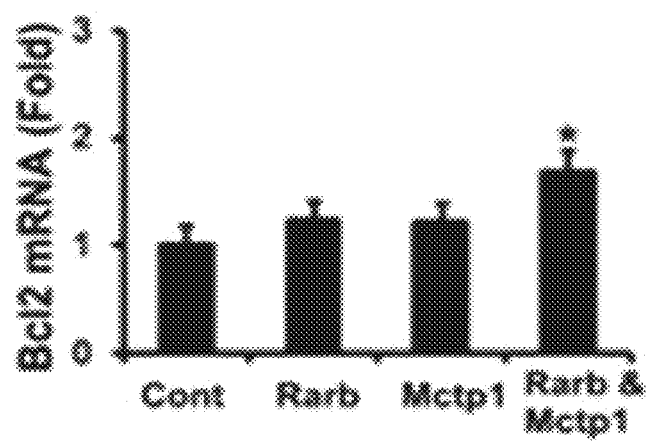
Figure 12D:
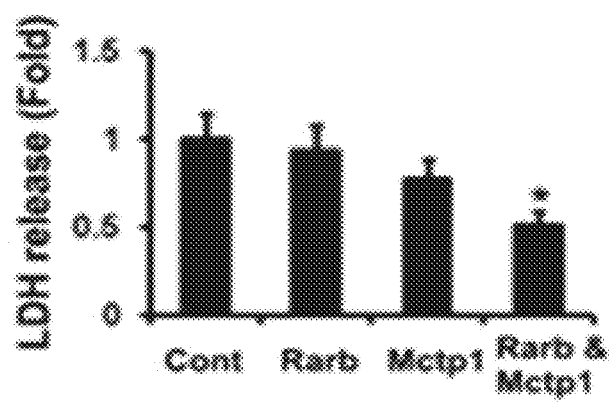
Figure 12E:
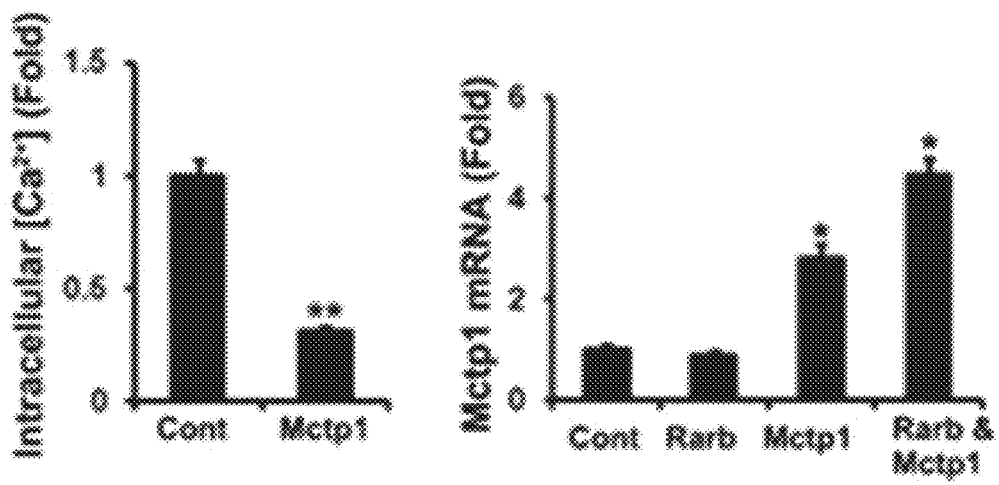
Figure 12F:
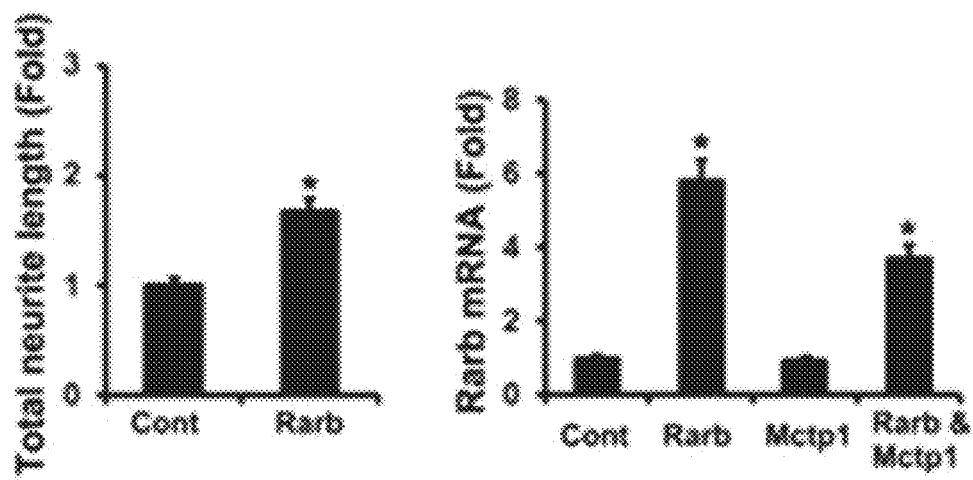
Figure 12G:
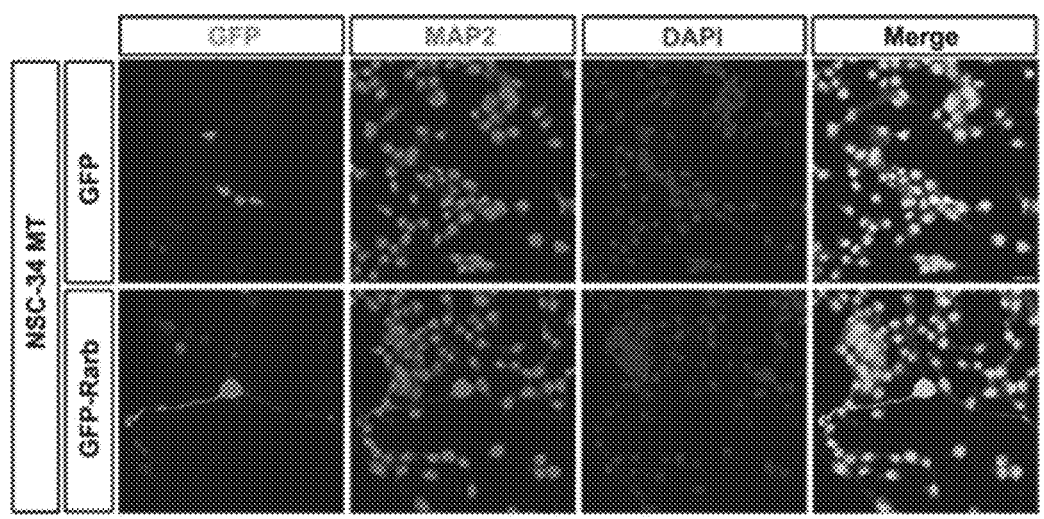

In order to prepare mtNSC-34 cells overexpressing Mctp1 and/or Rarb, the Mctp1 plasmid construct and/or the Rarb plasmid construct were transfected into mtNSC-34 cells by using Lipofectamine 2000 (Invitorgen) according to the procedure of the manufacturer and were collected after 48 hours. Subsequently, Western blotting (FIG. 12A), qRT-PCR (FIGS. 12B, 12C, and 12E, right, FIG. 12F, right), intracellular $Ca^{2+}$ analysis (FIG. 12E, left), axon production analysis (FIG. 12F, left), and LDH release analysis (FIG. 12D) were performed by the same method as the method described in <Example 2> to <Example 4>. mtNSC-cells were used as a control. As a result, as illustrated in FIGS. 12A to 12G, it was confirmed that, when Mctp1 and Rarb were simultaneously overexpressed, apoptosis was reduced (FIGS. 12A to 12D). In addition, it was confirmed that the intracellular $Ca^{2+}$ level was reduced by the increase of the Mctp1 expression in mtNSC-34 cells, and neuron differentiation was activated by the increase of the Rarb expression (FIGS. 12E to 12G).

From the above results, it was confirmed that the miR-18b regulation disorder by SOD1 mutation induced post-transcriptional regulation of Mctp1 and Rarb to reduce Mctp1 and Rarb, so that calcium signaling and neuron differentiation were suppressed and apoptosis was induced.

<Example 9> Confirming Regulation Disorder of miR-18b Signaling Pathway by SOD1 Mutation In order to identify whether SOD1 mutation performs a main role in miR-18b signaling pathway regulation disorder regardless of the kinds of the mutations, after each of mutated SOD1 (G85R) and SOD1 (D90A) was overexpressed in NSC-34 cont cells, Western blotting and qRT-PCR were performed to confirm expression of relating factors and apoptosis changes.

Specifically, each of the SOD1 (G85R) mutant gene-containing plasmid construct and the SOD1(D90A) mutant gene-containing plasmid construct was transfected into the NSC-34 cont cells cultured in Example <1-1> according to the procedure of the manufacturer by using Lipofectamine 2000 (Invitorgen) and was collected after 48 hours. Subsequently, Western blotting (FIG. 13A) and qRT-PCR (FIGS. 13B to 13G) analysis were performed by the same method as the method described in <Example 2> to <Example 4>. NSC-34 cont cells were used as a control.

Figure 13A:
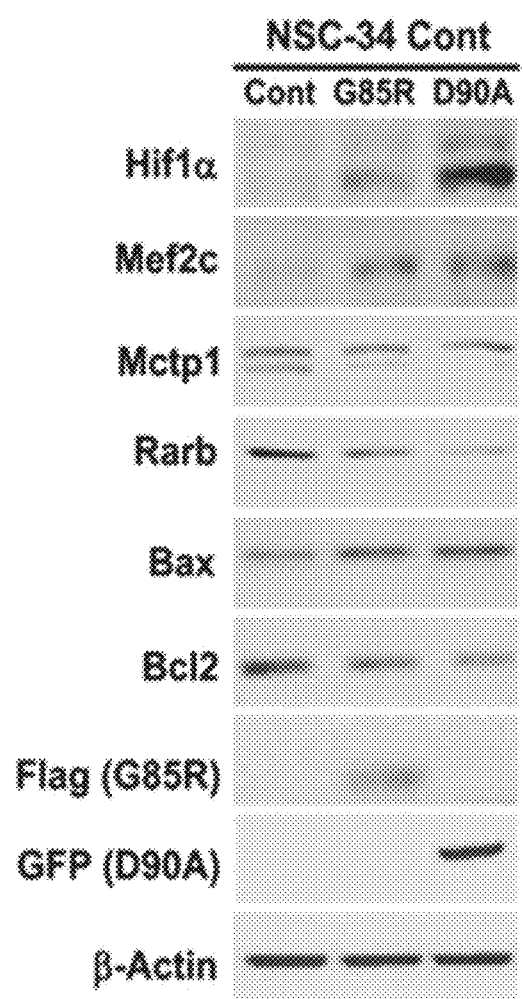
FIGS. 13A to 13G are diagrams confirming Hif1α, Mef2c, Mctp1, Rarb, miR-18b, and miR-206 expression changes and apoptosis changes in NSC-34 cont cells in which mutated SOD1 (G85R) and SOD1 (D90A) expression are increased according to an example of the present invention.
Figure 13B:
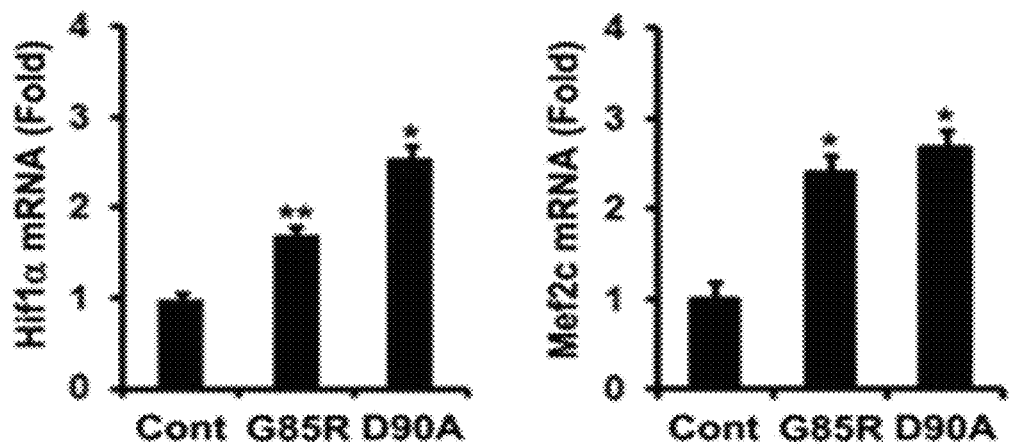
Figure 13C:
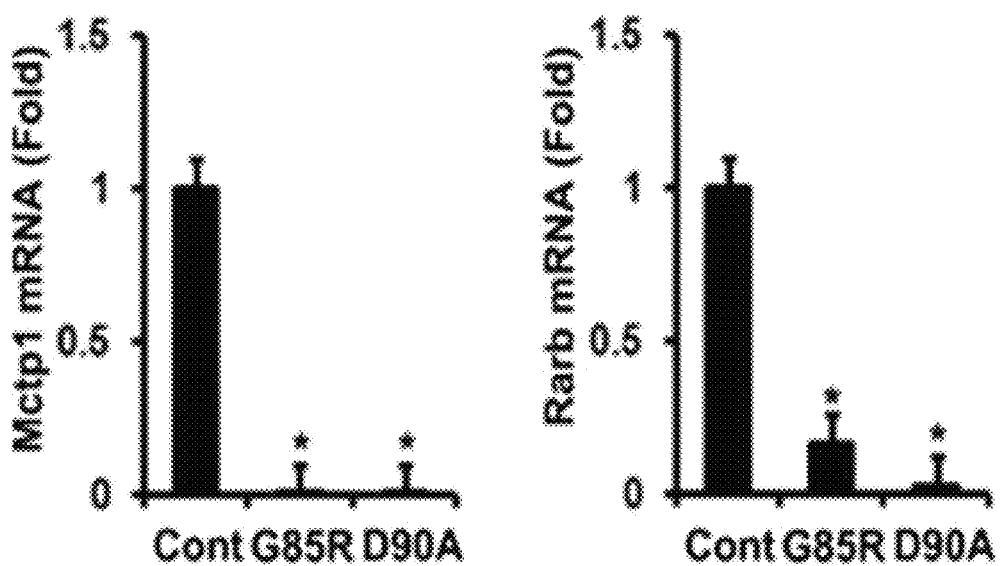
Figure 13D:
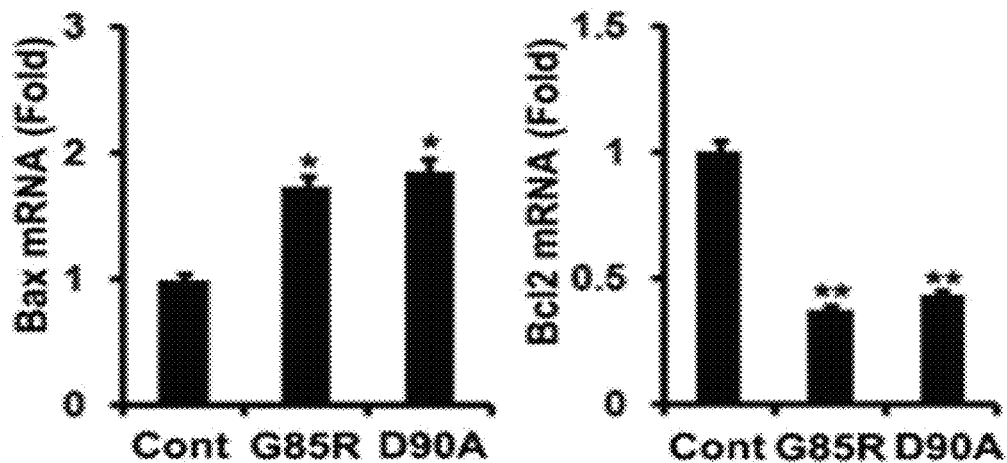
Figure 13E:
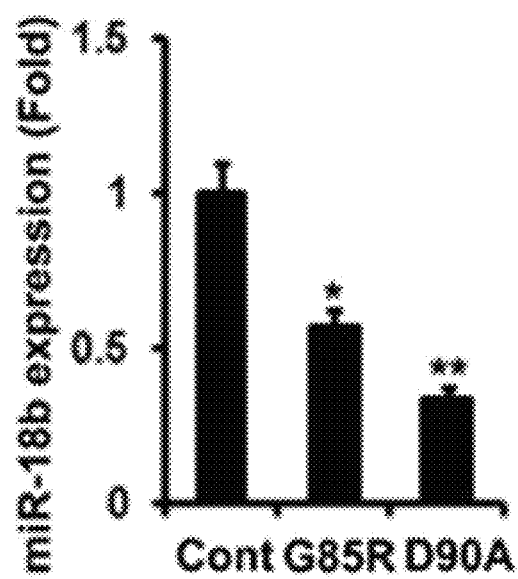
Figure 13F:
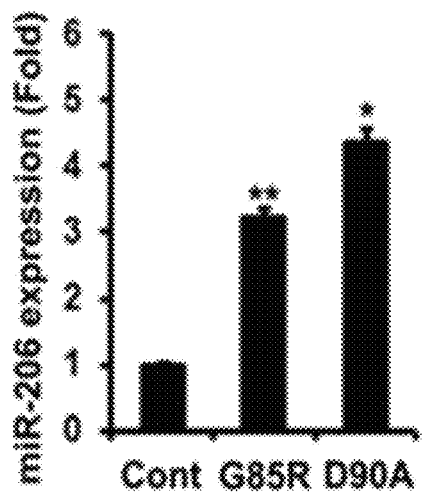
Figure 13G:
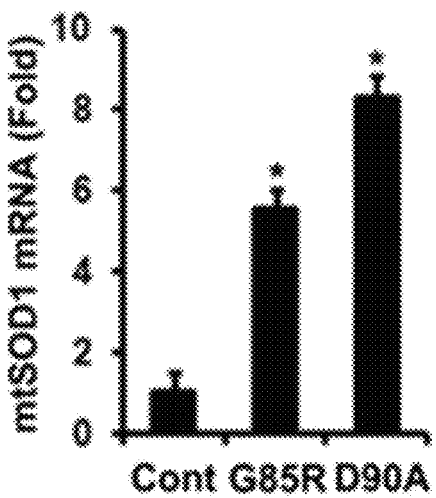

As a result, as illustrated in FIGS. 13A to 13G, it was confirmed that protein and mRNA levels of Hif1α and Mef2c were increased in NSC-34 cont cells in which mutated SOD1 was overexpressed, and protein and mRNA levels of Mctp1 and Rarb were reduced (FIGS. 13A to 13C). In addition, it was confirmed that, in the NSC-34 cont cells in which mutated SOD1 was overexpressed, miR-18b was reduced, and thus miR-206 was upregulated (FIGS. 13E to 13G). In addition, it was confirmed that, in the NSC-34 cont cells in which the mutated SOD1 was overexpressed, apoptosis was increased (FIG. 13D).

From the above results, it was confirmed that, regardless of the kinds of SOD1 mutation, the SOD1 mutation causes regulation disorder of the miR-18b signaling pathway, the miR-18b regulation disorder induces upregulation of Hif1α, upregulated Hif1α upregulated Mef2c, Mef2c acts as a transcriptional regulatory factor of miR-206 to induce miR-206 expression, and miR-206 directly involves in post-transcriptional regulation of Mctp1 and Rarb to induce calcium signaling, neuron differentiation suppression, and apoptosis.

<Example 10> Confirming Regulation Disorder of miR-18b Signaling Pathway in ALS

<10-1> Confirming Regulation Disorder of miR-18b Signaling Pathway in ALS Animal Model and Familial ALS Patient In order to identify whether the regulation disorder of miR-18b signaling pathway is caused by gene mutation in ALS, samples of an ALS mouse model and a familial ALS (fALS) patient were collected, and Western blotting and qRT-PCR were performed to confirm the expression and the apoptosis changes of miR-18b signaling pathway-related factors.

Specifically, SOD1-G93A transformed mouse (B6SJL-Tg (SOD1-G93A)1Gur/J) that expresses a human G93A mutant SOD1 gene was provided from The Jackson Laboratory, Bar Harbor, Me., USA and used. General (B6) normal mice (WT) were used as a control. Spinal cord tissues of each of the WT and the SOD1-G93A transformed mice were extracted 120 days after birth to obtain a spinal cord tissue sample of the mice. In addition, each spinal cord sample of a normal person and a familial ALS (fALS (G86S)) patient were provided from NBB. Subsequently, each of the spinal cord tissue sample (FIG. 14) and the spinal cord sample (FIG. 15) was used to perform Western blotting (FIGS. 14A, and 15A) and qRT-PCR (FIGS. 14B, 14C, 15B, and 15C) by the same method as the method described in <Example 2> to <Example 4>. In a case of the spinal cord samples, qRT-PCR was performed by using the primer of Table 8. In addition, qRT-PCR was performed by using primers (GenoSensor) respectively for hsa-miR-18b and hsa-miR-206.

TABLE 8

| Gene | | Human primer (5'→3') |
|------|---|----------------------|
| Hif1α | Forward | AGATAGCAAGACTTTCCTCAGTC (SEQ ID NO. 46) |
| | Reverse | CTGTGGTGACTTGTCCTTTAGTA (SEQ ID NO. 47) |
| Mef2c | Forward | CTACTTTACCAGGACAAGGAATG (SEQ ID NO. 48) |
| | Reverse | CTGAGATAAATGAGTGCTAGTGC (SEQ ID NO. 49) |
| Mctp1 | Forward | AGGAATAGTCAGCATCACCTTGA (SEQ ID NO. 50) |
| | Reverse | CAATGACTCCTCCTCTTTCTTCA (SEQ ID NO. 51) |
| Rarb | Forward | CTTCTCAGTGCCATCTGCTTAAT (SEQ ID NO.52) |
| | Reverse | AATTACACGCTCTGCACCTTTAG (SEQ ID NO. 53) |

TABLE 8-continued

| Gene | | Human primer (5'→3') |
|---|---|---|
| Bax | Forward | AAGCTGAGCGAGTGTCTCAA (SEQ ID NO. 54) |
| | Reverse | AGTAGAAAAGGGCGACAACC (SEQ ID NO. 55) |
| Bcl2 | Forward | ACGCCCCATCCAGCCGCATC (SEQ ID NO. 56) |
| | Reverse | CACACATGACCCCACCGAACTCA (SEQ ID NO. 57) |
| GAPDH | Forward | CTGCATTCGCCCTCTTAATG (SEQ ID NO. 58) |
| | Reverse | TGAGGTCAATGAAGGGGTCA (SEQ ID NO. 59) |
| SOD1 | Forward | GTGGGGAAGCATTAAAGGACTGAC (SEQ ID NO. 60) |
| | Reverse | CAATTACACCACAAGCCAAACGAC (SEQ ID NO. 61) |

Figure 14A:
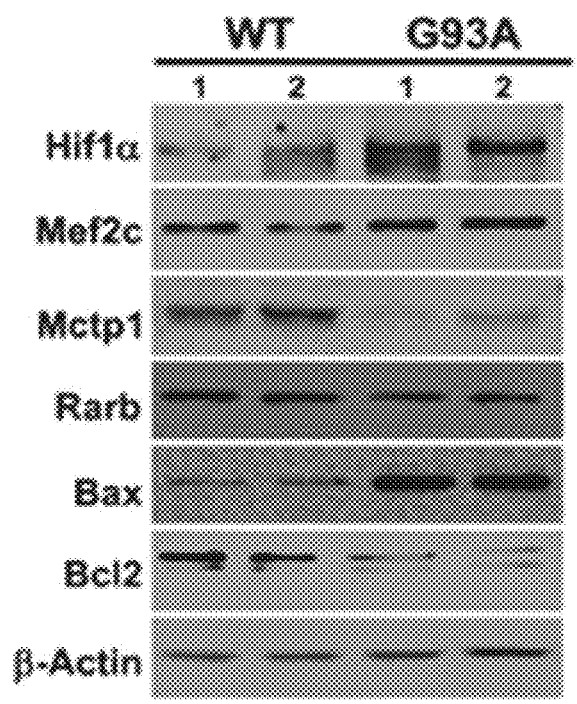
FIGS. 14A to 14C and 15A to 15C are diagrams confirming Hif1α, Mef2c, Mctp1, Rarb, miR-18b, and miR-206 expression changes and apoptosis changes in a spinal cord tissue sample of a mouse model of atrophic lateral sclerosis (ALS) disease and a spinal cord sample of familial ALS (fALS (G86S)) patient according to an example of the present invention.
Figure 14B:
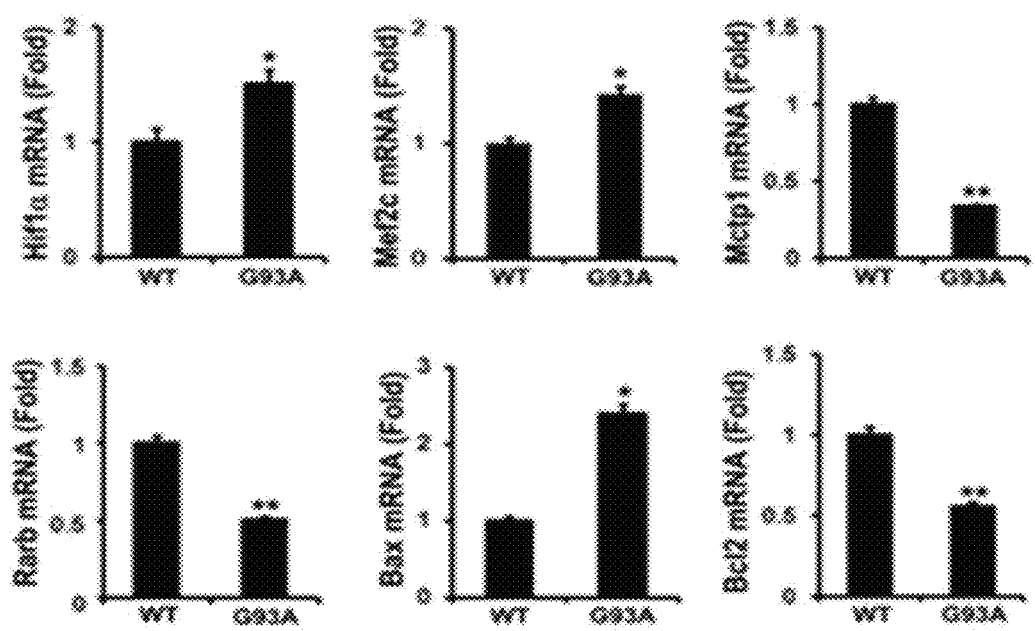
Figure 14C:
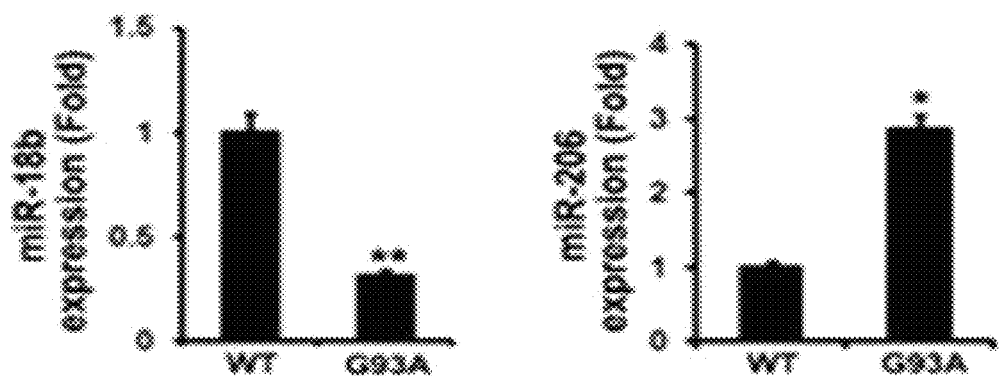
Figure 15A:
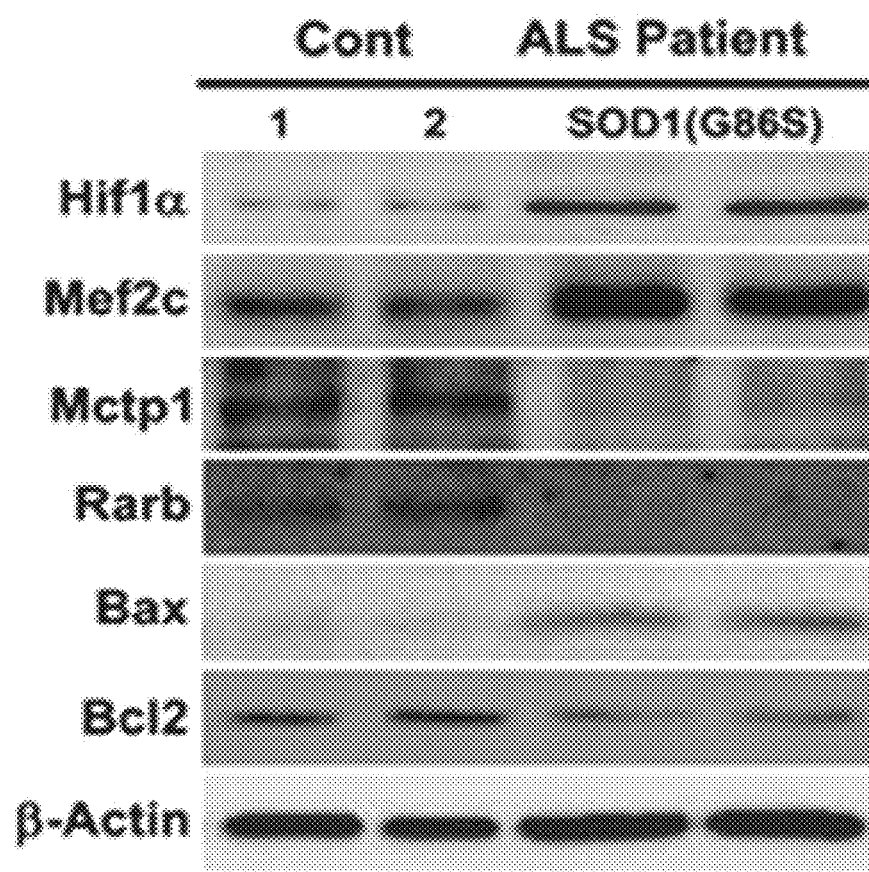
Figure 15B:
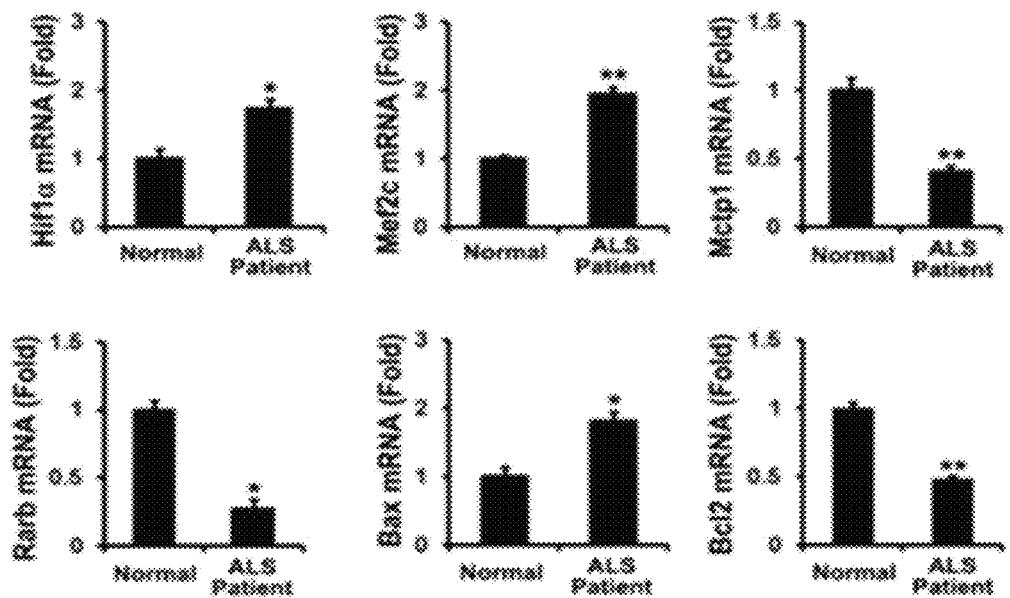
Figure 15C:
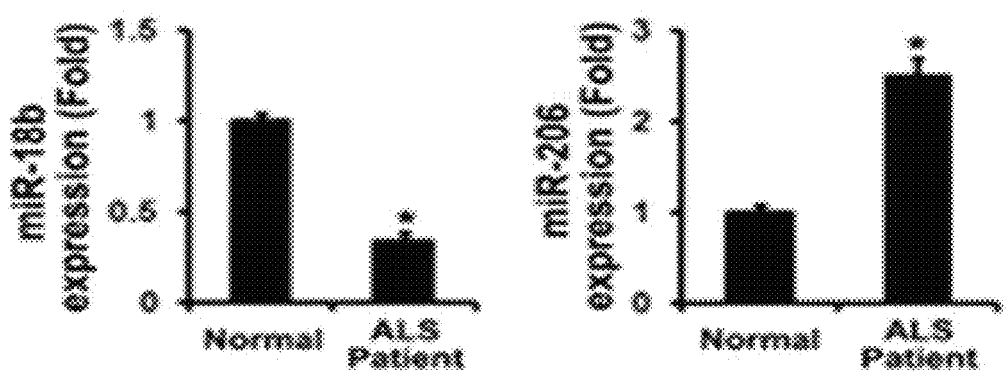

As a result, as illustrated in FIGS. 14A to 14C and 15A to 15C, it was confirmed that protein and mRNA expression of Hif1α and Mef2c in a ALS mouse model was significantly increased in the G93A Tg mouse, but protein and mRNA expression of Mctp1 and Rarb were significantly reduced. In addition, it was confirmed that apoptosis was induced in the G93A Tg mouse by increased Bax and reduced Bcl2 expression (FIGS. 14A and 14B). Also, it was confirmed that miR-18b was downregulated in the G93A Tg mouse, and miR-206 was upregulated (FIG. 14C). The same results were confirmed in the fALS (G86S) patient spinal cord sample (FIGS. 15A to 15C).

<10-2> Confirming Regulation Disorder of miR-18b Signaling Pathway in hiPSC-Derived Motor Neuron of SOD1 (G17S) fALS Patient In order to identify whether the miR-18b signaling pathway plays a main role in a human motor neuron (MN), familial ALS (fALS (G17S)) patient blood was collected, human induced pluripotent stem cells (hiPSC) were induced from the blood, the hiPSC was differentiated into neuron stem cells (human neuron stem cells, hNSCs) and then differentiated into motor neurons, and qRT-PCR was performed to confirm the expression of miR-18b signaling pathway-related factors. In addition, intracellular calcium signaling, cell differentiation, and apoptosis changes were confirmed.

Figure 16A:
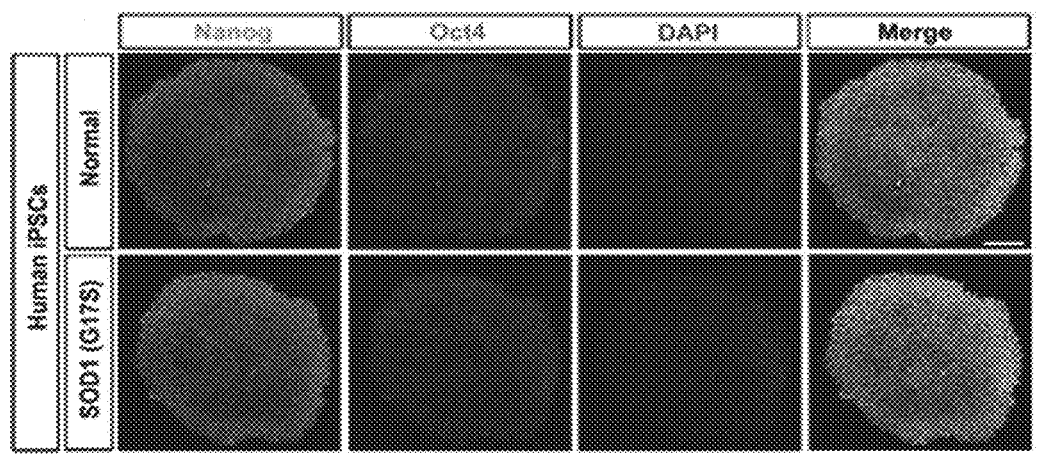
FIGS. 16A to 16D are diagrams confirming motor neurons (MN) derived from hNSCs obtained by differentiating neuron stem cells (hNSCs) from hiPSC derived from a blood sample of a SOD1 (G17S) fALS patient according to an example of the present invention.
Figure 16B:
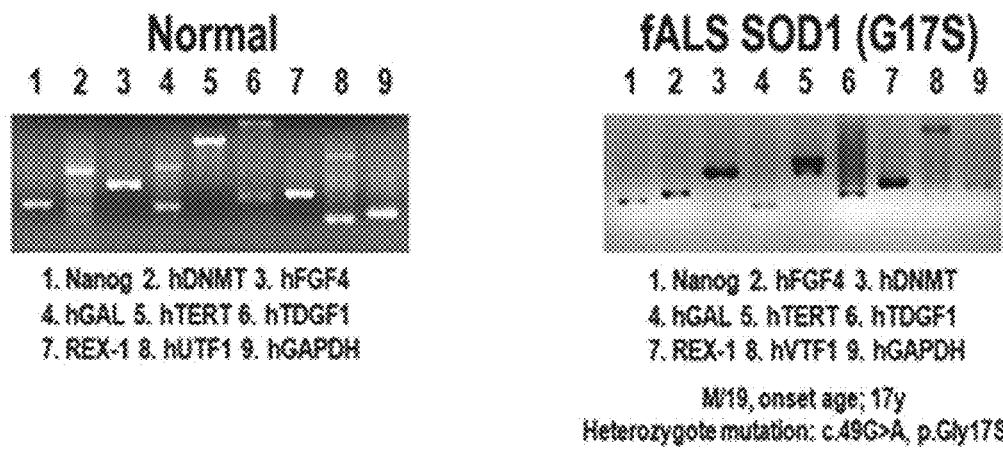

Specifically, in order to induce the hiPSC from the blood, each blood sample of a normal person and a fALS SOD1 (G17S) patient was donated from the neurology department of Seoul National University Hospital (IRB number 1009-059-332). Subsequently, Ficoll-Paque (GE Healthcare Life Sciences) was used to isolate peripheral blood mononuclear cells (PBMC) from the whole blood, and the PBMC were cultured and proliferated in a StemPro-34 medium including 1% of penicillin-streptomycin, 100 ng/mL of hSCF, 100 ng/mL of hFLT-3, 20 ng/mL of hIL-3, and 20 ng/mL of hIL-6. $1\times10^6$ PBMCs were transduced by using Sendai virus (multiplicity of infection (MOI)=5) containing Oct3/4, Sox2, Klf4, and cMyc (CytoTune®-iPS Sendai Reprogramming Kit, Life technologies). After three days, the transduced cells were treated in a cell start-coated 35-mm dish which included a cytokine-free StemPro-34 medium and in which 20 ug/ml mitomycin C-treated Human Scrotum foreskin fibrin (HFF) was seeded at the concentration of $1.5\times10^5$ cell/dish, and the medium was replaced daily before the hiPSCs began to be transferred. Subsequently, the medium was replaced with a DMEM F/12-based iPSC medium including 15% of knockout SR, 40 ng/ml of bFGF, 1% of non-essential amino acid, 50 U/ml of penicillin, 50 μg/ml of streptomycin, and 0.1 mM of 2-mercapto ethanol and a cytokine-free StemPro-34 medium in a ½ volume. In order to complete the transfer, the iPSC was replaced daily. After 30 days or longer, colonies were collected and subcultured in new mitotically inactivated HFFs to proliferate hiPSC. In addition, immunocytochemical staining and RT-PCR analysis were performed by using pluripotent markers to confirm that normal hiPSC and fALS SOD1 (G17S) hiPSC were induced (FIGS. 16A and 16B).

Figure 16C:
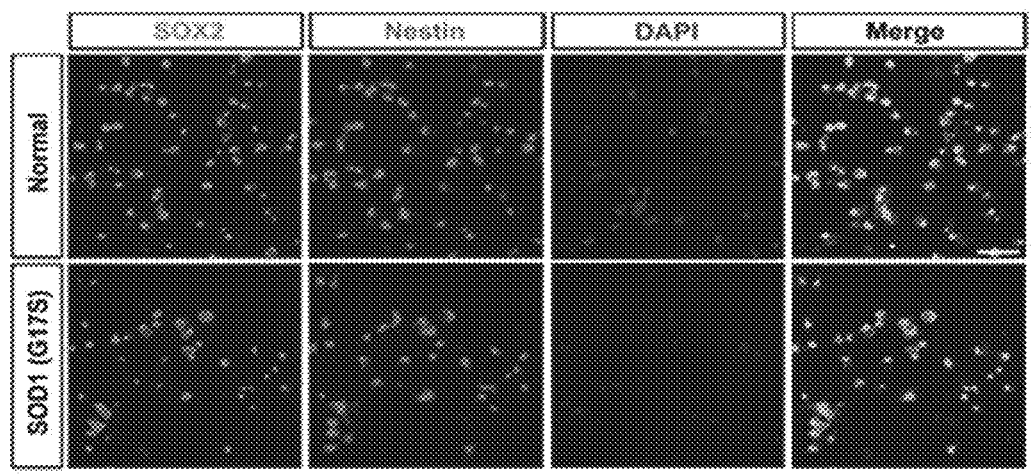

Then, in order to generate neuron stem cells (NSC), the colonies were isolated by using 2 mg/ml dispase (Gibco) and treated in 60-mm incoated bacterial plates, and the medium was replaced daily with an embryoid body (EB) medium containing an Essential 6 medium containing 15% of knockout SR (Gibco), 50 U/ml of penicillin, and 50 ug/ml of streptomycin for five to seven days at 37° C. Subsequently, the formed EB was moved to a cell start-coated 35-mm culture dish. After two or three days, when the EB was attached to the dish, until neuron structures appeared, the medium was replaced from a DMEM/F12 (1% of non-essential amino acid, 50 U/ml of penicillin, 50 ug/ml of streptomycin, and 0.1 mM of 2-mercapto ethanol) medium containing 0.5% of an N2 supplement to a DMEM/F12 (containing 1% of non-essential amino acid, 50 U/ml of penicillin, 50 ug/ml of streptomycin, and 0.1 mM of 2-mercapto ethanol) medium containing 1% of a N2 supplement and 40 bFGF twice a day. Subsequently, the neuron structure was isolated and cultured in a suspended state to obtain neurospheres. The obtained neurospheres were fragmented, cultured in a cell start-coated culture dish for one day, and treated with Accutase (Gibco) for one hour at 37° C. NSC was cultured in a DMEM/F12 medium containing 1% of non-essential amino acid, 50 U/ml of penicillin, 50 ug/ml of streptomycin, 0.1 mM of 2-mercapto ethanol, 0.5% of a N2 supplement, and 40 ng/ml of a b-fibroblast growth factor. Subsequently, immunocytochemical staining was performed by using NSC markers to confirm that normal NSC and fALS SOD1 (G17S) NSC were generated (FIG. 16C).

Figure 16D:
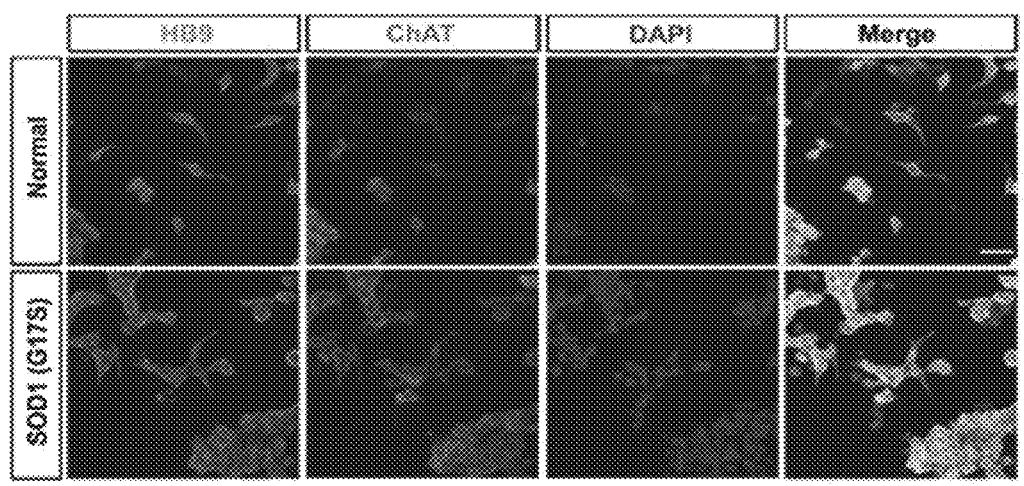

In order to differentiate NSC to motor neurons (MN), the NSC was cultured two days in Cell Start containing 1 μg/ml of laminin and 5 ug/ml of heparin coated plate and DMEM/F12 to which non-essential amino acid, penicillin/streptomycin, 2-mercapto ethanol, N2, and b-FGF were added, then cultured in a DMEM/F12 medium containing 0.1 mM of 2-mercapto ethanol, 0.5% of N2 supplement, and 40 ng/ml of bFGF, and a mixture of a DMEM/F12 medium and a neuron fiber medium (0.1 mM of 2-mercapto ethanol, 0.5% of a N2 supplement, 40 ng/ml of bFGF, 10 ng/ml of a neural growth factor, 10 ng/ml of sonic hedgehog (R&D Systems), 10 μM of forskolin (Sigma), 1 μM of retinoic acid (Sigma), 10 ng/ml of GDNF (glial cell-derived neurotrophic factor), 10 ng/ml of brain-derived neurotrophic factor (BDNF), 10 ng/ml of ciliary neurotrophic factor, 10 ng/ml of insulin-like growth factor 1, and 10 ng/ml of neurotrophin-3 (NT3)) was administered daily or for one week daily. In addition, immunocytochemical staining was performed using MN markers to confirm that the NSC was differentiated into normal MN and fALS SOD1 (G17S) MN (FIG. 16D).

The differentiated normal MN and fALS SOD1 (G17S) MN each were used to perform qRT-PCR (FIGS. 17A to 17F), intracellular $Ca^{2+}$ analysis (FIG. 17C), axon production analysis (FIG. 17D), and LDH release analysis (FIG. 17G) by the same method as the method described om Example <10-1>.

Figure 17A:
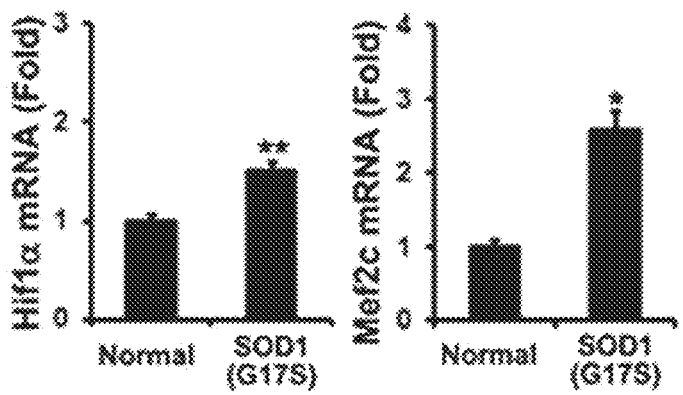
FIGS. 17A to 17G are diagrams confirming Hif1α, Mef2c, Mctp1, Rarb, miR-18b, and miR-206 expression changes, intracellular calcium signaling, cell differentiation, and apoptosis changes in hiPSC-derived MNs of a SOD1 (G17S) fALS patient according to an example of the present invention.
Figure 17B:
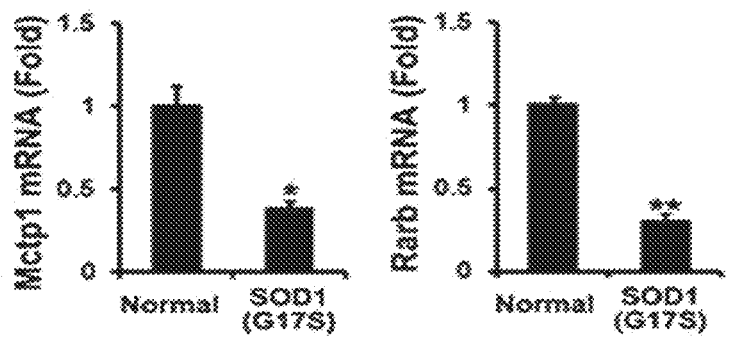
Figure 17C:
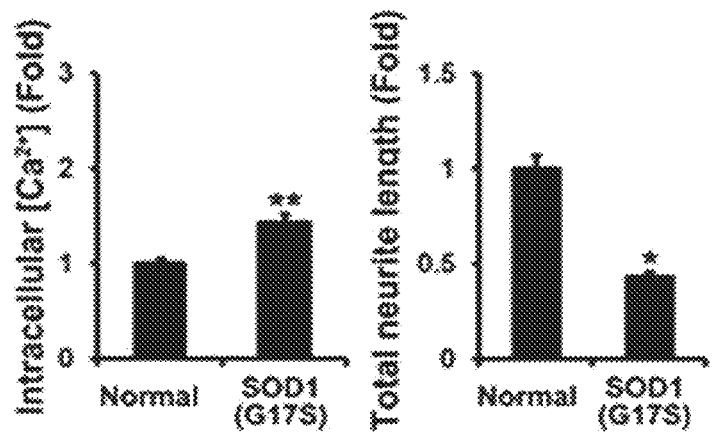
Figure 17D:
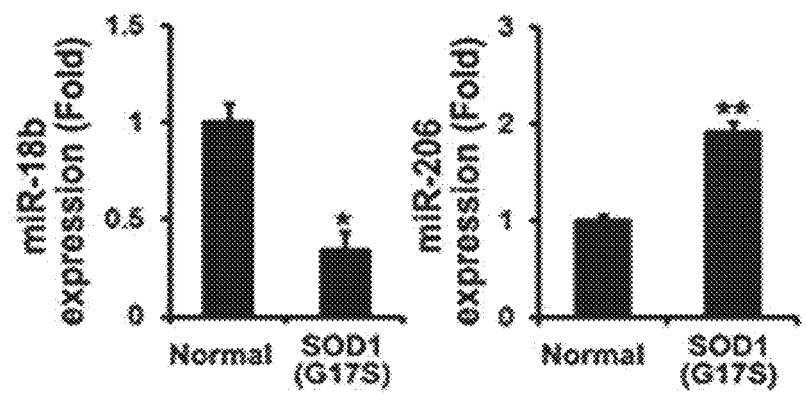
Figure 17E:
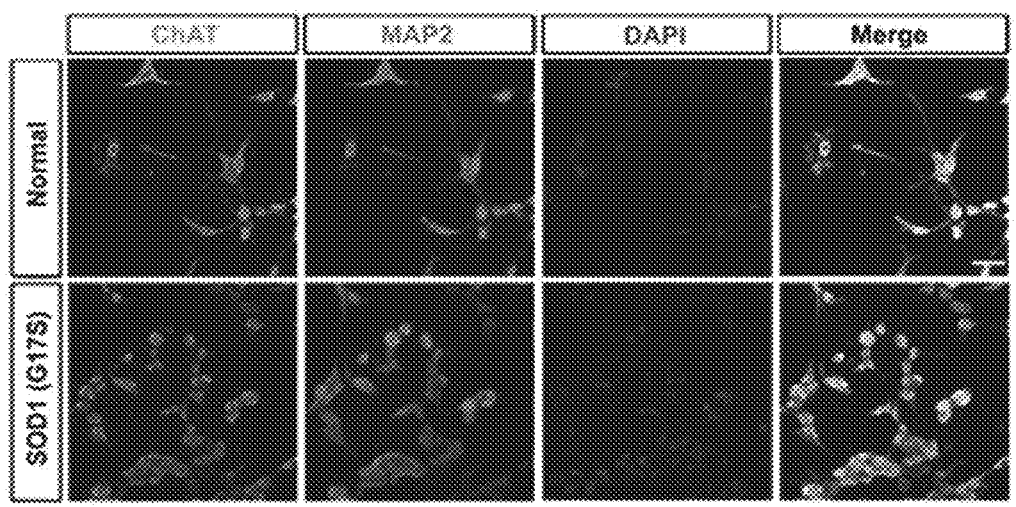
Figure 17F:
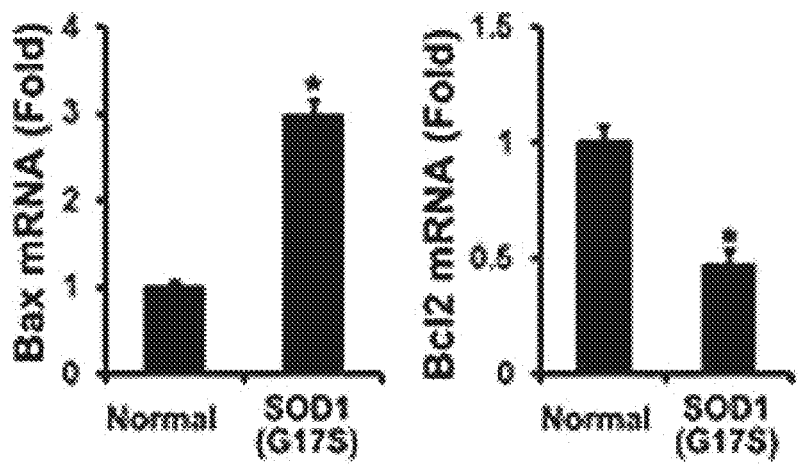
Figure 17G:
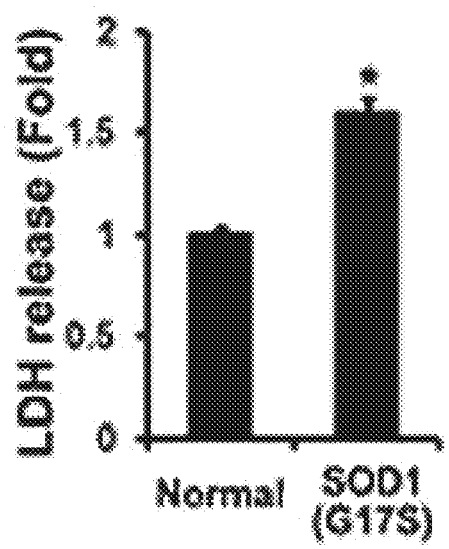

As a result, as illustrated in FIGS. 17A and 17B, it was confirmed that, in fALS SOD1 (G17S) MN, mRNA expression of Hif1α and Mef2c was significantly increased, but mRNA levels of Mctp1 and Rarb were prominently reduced (FIGS. 17A and 17B). In addition, when miR-18b and miR-206 levels were measured in fALS SOD1(G17S) MNs, it was confirmed that miR-18b was significantly reduced, and miR-206 was significantly increased (FIG. 17D). Also, it was confirmed that, in fALS SOD1 (G17S) MNs, $Ca^{2+}$ was accumulated, neuron differentiation was suppressed, and apoptosis was induced (FIGS. 17C and 17E to 17G).

From the above results, it was confirmed that the miR-18b signaling pathway was involved in SOD1 mutation-associated ALS, and apoptosis was induced by the regulation disorder of the miR-18b signaling pathway in SOD1 mutation-associated ALS.

<Example 11> Confirming miR-18 Regulation Disorder in Duchenn Muscular Dystrophy (DMD)

<11-1> Confirming miR-18 Regulation Disorder in Dystrophin Expression Suppression Myoblast In order to identify whether the miR-18b regulation disorder is developed by gene mutation in DMD as a muscle disease caused by another gene mutation, qRT-PCR was performed to confirm miR-18 expression in Dystrophin expression suppression myoblast.

Figure 18:
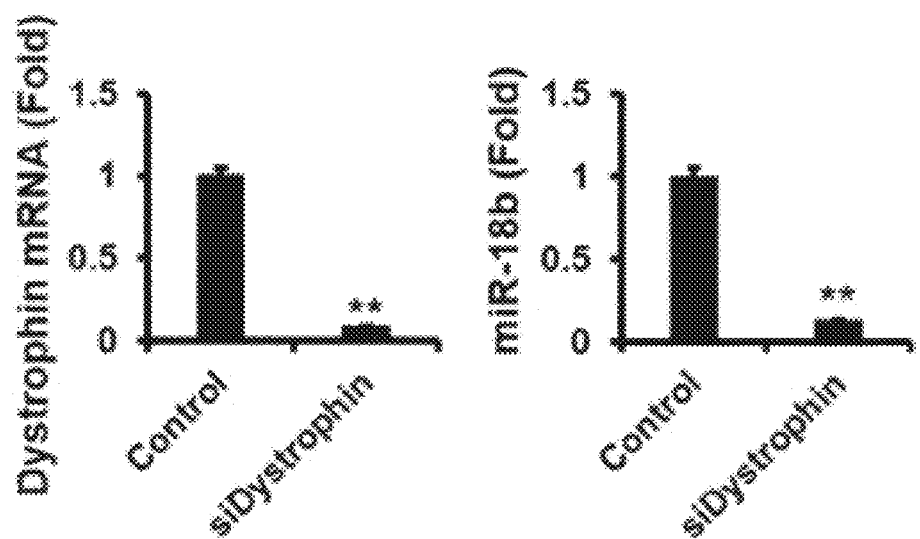
FIG. 18 is a diagram confirming expression changes in miR-18b in myoblast in which Dystrophin expression is reduced according to an example of the present invention.

Specifically, Dystrophin expression suppression C2C12 cells obtained in Example <1-3> were collected to perform qRT-PCR by the same method as the method described in <Example 2> (FIG. 18). C2C12 cells obtained by transducing siControl were used as a control.

As a result, as illustrated in FIG. 18, it was confirmed that miR-18 expression was reduced in Dystrophin expression suppression C2C12 cells (FIG. 18).

<11-2> Confirming miR-18 Regulation Disorder in DMD Animal Model

In order to identify whether miR-18b regulation disorder is caused by gene mutation in DMD, qRT-PCR was performed to confirm the miR-18 expression in a DMD animal model.

Specifically, mdx mice (two to four weeks after birth), which were DMD animal models, were provided from the Jackson laboratory. The muscle tissues were extracted from the mdx mice, and qRT-PCR was performed by the same method as the method described in <Example 2> (FIG. 19).

Figure 19:
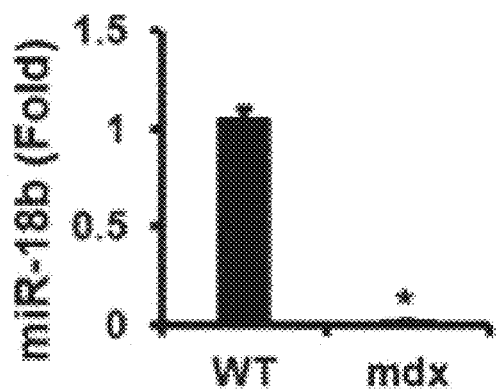
FIG. 19 is a diagram confirming miR-18b expression in a mouse model of Duchenne muscular dystrophy (DMD) according to an example of the present invention.

As a result, as illustrated in FIG. 19, it was confirmed that miR-18 expression was reduced in the DMD mice (FIG. 19).

From the above results, it was confirmed that regulation disorder of miR-18b signaling pathway causes from Dystrophin mutation-associated DMD, and thus it was confirmed that miR-18b can be used as target miRNA for DMD diagnosis and used for preventing and treating DMD.

<11-3> Confirming Treatment Effect by miR-18 in DMD Animal Model

It is known that, in the DMD mouse model, the expression of CTGF increases to induce fibrosis (Morales et al.). Accordingly, in order to identify the treatment effect by miR-18 in DMD, miR-18b was administered in the DMD animal to confirm CTGF expression.

Figure 20A:
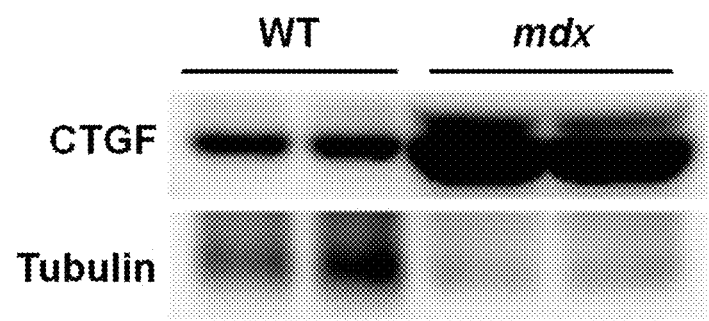
FIGS. 20A and 20B are diagrams confirming CTGF expression in a DMD mouse model according to an example of the present invention.
Figure 20B:
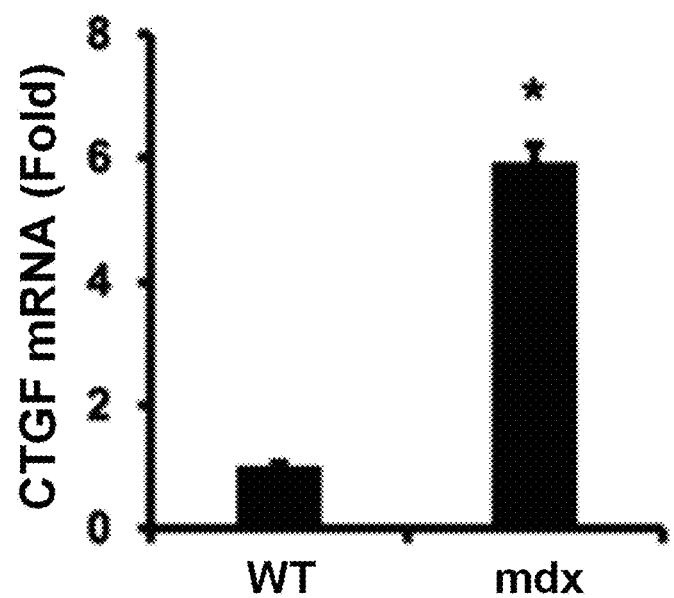

Specifically, mdx mice (two to four weeks after birth), which were DMD models, were provided from the Jackson laboratory. The skeletal muscle tissues were extracted from the mdx mice, and Western blotting (FIG. 20A) and qRT-PCR (FIG. 20B) were performed by the same method as the method described in <Example 2> to <Example 4> to confirm CTGF expression. Normal mice (two to four weeks after birth) were used as a control.

Subsequently, 100 ug/50 ul of miR-18b plasmid construct prepared in Example <5-2> was subcutaneously injected into the skeletal muscle of the mdx mice. After two weeks from subcutaneous injection, skeletal muscle tissues were extracted from mdx mice. 24 hours prior to the extraction, 100 ul of 1% Evans blue, which was a muscle damage marker, was intraperitoneal injected. Next, the changes of Evans blue in the extracted muscle tissue were confirmed by fluorescence microscopy (FIG. 21), mRNA was isolated, and qRT-PCR was performed by the same method as the method described in <Example 2> to confirm expression changes of miR-18b and CTGF were confirmed (FIG. 22). As a control, mdx mice to which an empty vector was subcutaneously injected were used instead of miR-18b.

Figure 21:
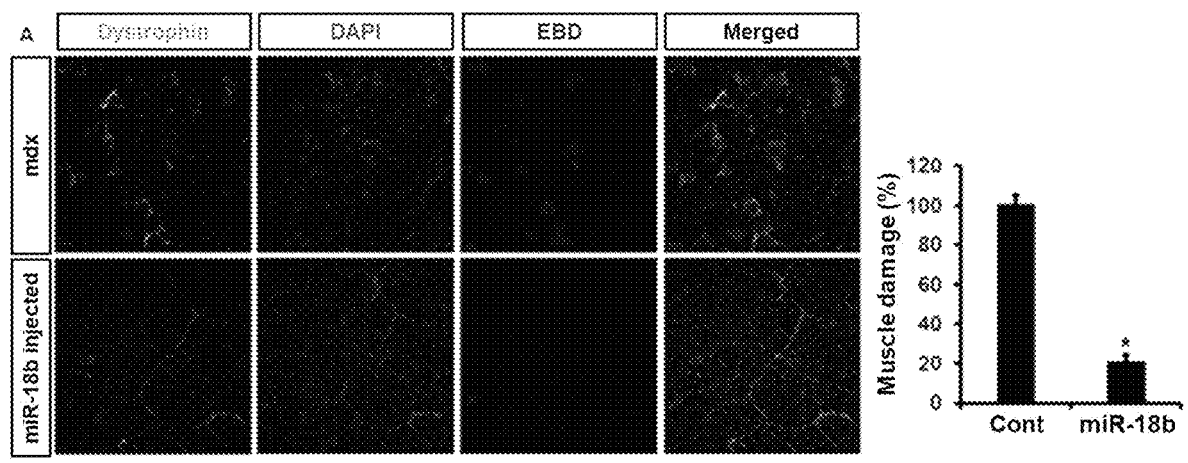
FIG. 21 is a diagram confirming muscle damage changes after subcutaneous injection of miR-18b in the DMD mouse model according to an example of the present invention.
Figure 22:
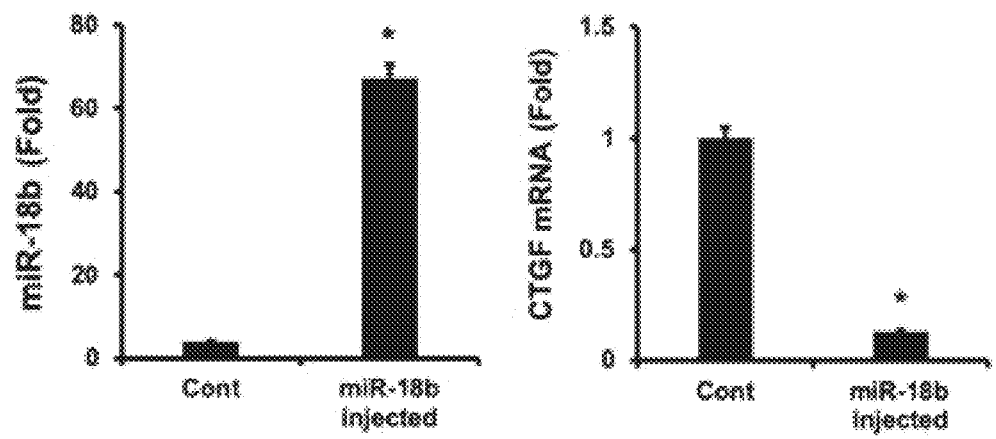
FIG. 22 is a diagram confirming CTGF expression changes after subcutaneous injection of miR-18b in the DMD mouse model according to an example of the present invention.

As a result, as illustrated in FIGS. 20 to 22, it was confirmed that CTGF expression was increased in the DMD mice than in the normal mice. In addition, in a case of the DMD mice, the expression of Evans blue (EBD) was increased to exhibit muscle damages. Meanwhile, it was confirmed that, in a case of the DMD mice to which miR-18b was injected, the expression of Evans blue was prominently reduced (reduced by 80% or more), and CTGF expression was also prominently reduced.

From the above results, it was understood that miR-18b can be used as a treatment for DMD diseases.

Figure 23:
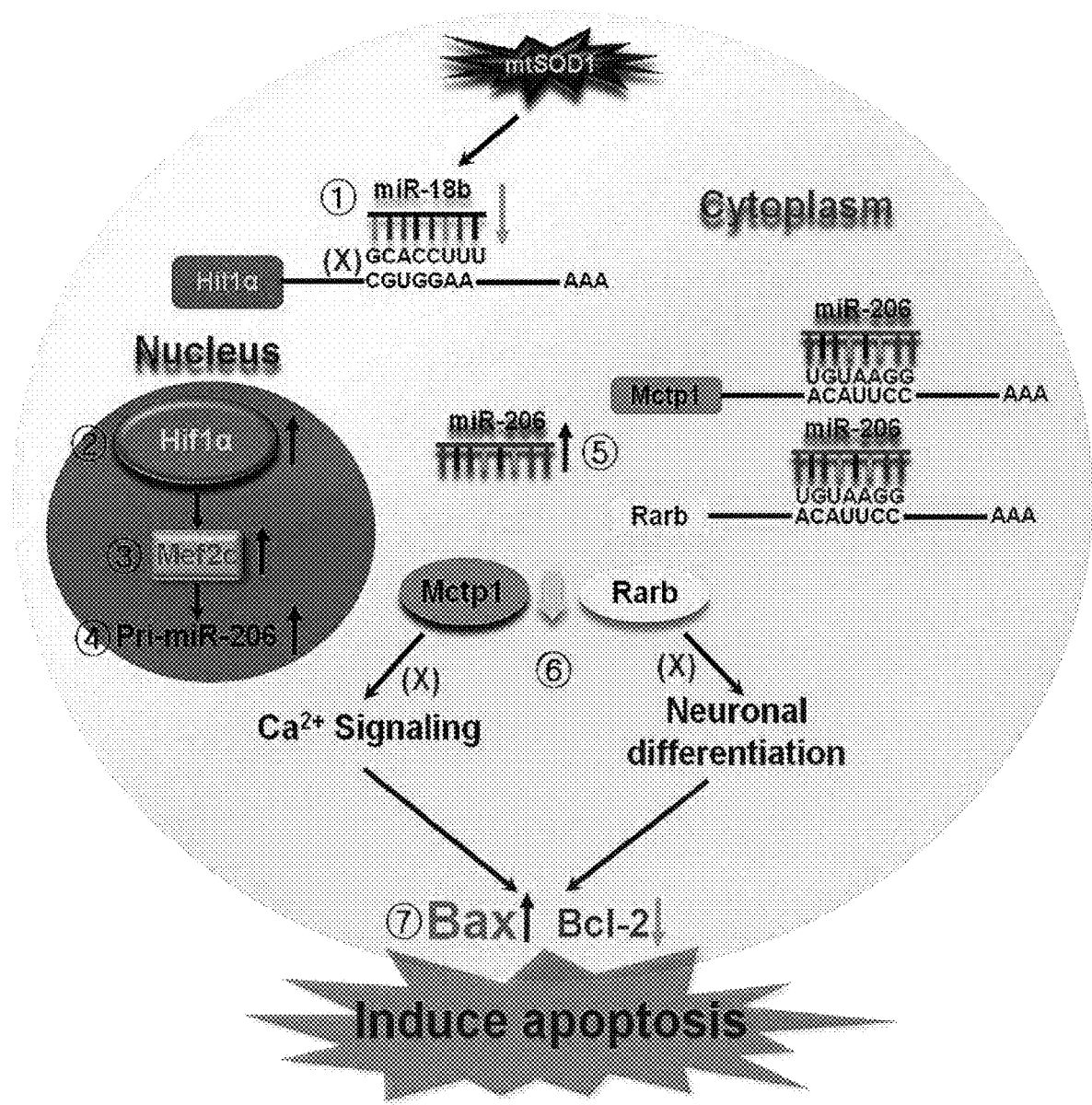
FIG. 23 is a diagram schematically confirming a regulation disorder of miR-18b signaling pathway by gene mutation.

From the results of <Example 1> to <Example 11>, it was confirmed that, as illustrated in the schematic diagram of FIG. 23, the gene mutation reduced miR-18b expression to cause the regulation disorder of the miR-18b signaling pathway, the miR-18b regulation disorder induces the upregulation of Hif1α, upregulated Hif1α upregulates Mef2c, Mef2c induces miR-206 expression, miR-206 directly involves in post-transcriptional regulation of Mctp1 and Rarb, and calcium signaling, neuron differentiation suppression, and apoptosis were induced. Therefore, miR-18b can be used as a target factor in the diagnosis and treatment of muscle diseases caused by the gene mutation such as ALS and DMD.

The invention claimed is:

1. A method of diagnosing a muscle disease caused by gene mutation in a subject, the method comprising:
   measuring an expression level of miR-18b in a sample isolated from the subject and comparing the sample with a normal control;
   identifying the subject as having the muscle disease caused by the gene mutation when expression level of said miR-18b is decreased in comparison with that of the normal control; and
   administering a therapeutically effective amount of a treatment for the muscle disease to the subject when the subject is identified as having the muscle disease,
   wherein the muscle disease caused by gene mutation is selected from the group consisting of Duchenne muscular dystrophy, Backer muscular dystrophy, muscular atrophy, and amyotrophic lateral sclerosis.

2. The method of diagnosing a muscle disease according to claim 1,
   wherein the sample is selected from the group consisting of a tissue, a cell, plasma, serum, blood, saliva, and urine.

3. The method of diagnosing a muscle disease according to claim 1,
   wherein the expression level is measured by one or more method selected from the group consisting of reverse transcription polymerase chain reaction (RT-PCR), quantitative RT-PCR, real-time RT-PCR, Northern blotting, and transcriptome analyses.

4. The method of diagnosing a muscle disease according to claim 1, further comprising:
   measuring an expression level of one or more selected from the group consisting of hypoxia inducible factor 1 alpha (Hif1α), myocyte specific enhancer factor 2c (Mef2c), multiple C2 domains transmembrane protein 1 (Mctp1), retinoic acid receptor beta (Rarb), and miR-206 in the sample and comparing the expression level with that of the normal control; and
   confirming the subject has the muscle disease caused by gene mutation when the expression level of said Hif1α, Mef2c or miR-206 is increased in comparison with that of the normal control or when the expression level of said Mctp1 or Rarb is decreased in comparison with that of the normal control.

5. The method of diagnosing a muscle disease according to claim 1, wherein administering a therapeutically effective amount of a treatment for the muscle disease to the subject comprises administering a therapeutically effective amount of miR-18b to the subject.

* * * * *

SEQUENCE LISTING

```
<160> NUMBER OF SEQ ID NOS: 66

<210> SEQ ID NO 1
<211> LENGTH: 23
<212> TYPE: RNA
<213> ORGANISM: Homo sapiens

<400> SEQUENCE: 1
uaaggugcau cuagugcagu uag                    23
```

```
<210> SEQ ID NO 2
<211> LENGTH: 22
<212> TYPE: RNA
<213> ORGANISM: Homo sapiens

<400> SEQUENCE: 2
ugcccuaaau gccccuucug gc                                                  22

<210> SEQ ID NO 3
<211> LENGTH: 71
<212> TYPE: RNA
<213> ORGANISM: Homo sapiens

<400> SEQUENCE: 3
uguguuaagg ugcaucuagu gcaguuagug aagcagcuua gaaucuacug cccuaaaugc         60
cccuucuggc a                                                              71

<210> SEQ ID NO 4
<211> LENGTH: 21
<212> TYPE: DNA
<213> ORGANISM: Mus musculus

<400> SEQUENCE: 4
ggccuuacag ggcaaaaact t                                                   21

<210> SEQ ID NO 5
<211> LENGTH: 22
<212> TYPE: DNA
<213> ORGANISM: Mus musculus

<400> SEQUENCE: 5
gactccaaca tacccatttc tg                                                  22

<210> SEQ ID NO 6
<211> LENGTH: 22
<212> TYPE: DNA
<213> ORGANISM: Mus musculus

<400> SEQUENCE: 6
taatatctct tcccgctcct tc                                                  22

<210> SEQ ID NO 7
<211> LENGTH: 21
<212> TYPE: DNA
<213> ORGANISM: Mus musculus

<400> SEQUENCE: 7
tcatccttac gcctaaggaa g                                                   21

<210> SEQ ID NO 8
<211> LENGTH: 21
<212> TYPE: DNA
<213> ORGANISM: Mus musculus

<400> SEQUENCE: 8
ccggaacttc acatatggat c                                                   21

<210> SEQ ID NO 9
<211> LENGTH: 20
<212> TYPE: DNA
<213> ORGANISM: Mus musculus

<400> SEQUENCE: 9
```
cacctgaagg tgaatgttgg 20

<210> SEQ ID NO 10
<211> LENGTH: 20
<212> TYPE: DNA
<213> ORGANISM: Mus musculus

<400> SEQUENCE: 10
cacttgaact tggggtcaag 20

<210> SEQ ID NO 11
<211> LENGTH: 21
<212> TYPE: DNA
<213> ORGANISM: Mus musculus

<400> SEQUENCE: 11
gatctacact tgccatcgag a 21

<210> SEQ ID NO 12
<211> LENGTH: 21
<212> TYPE: DNA
<213> ORGANISM: Mus musculus

<400> SEQUENCE: 12
ctttccggat cttctcagtg a 21

<210> SEQ ID NO 13
<211> LENGTH: 20
<212> TYPE: DNA
<213> ORGANISM: Mus musculus

<400> SEQUENCE: 13
tggtgcaaca gtattccact 20

<210> SEQ ID NO 14
<211> LENGTH: 22
<212> TYPE: DNA
<213> ORGANISM: Mus musculus

<400> SEQUENCE: 14
ctggaacatg tagaccatgt ag 22

<210> SEQ ID NO 15
<211> LENGTH: 20
<212> TYPE: DNA
<213> ORGANISM: Mus musculus

<400> SEQUENCE: 15
catgtttgtg atgggtgtga 20

<210> SEQ ID NO 16
<211> LENGTH: 20
<212> TYPE: DNA
<213> ORGANISM: Mus musculus

<400> SEQUENCE: 16
gatgcaggga tgatgttctg 20

<210> SEQ ID NO 17
<211> LENGTH: 23
<212> TYPE: DNA
<213> ORGANISM: Mus musculus

<400> SEQUENCE: 17
gttcaccaaa gttgaatcag agg 23

<210> SEQ ID NO 18
<211> LENGTH: 23
<212> TYPE: DNA
<213> ORGANISM: Mus musculus

<400> SEQUENCE: 18
cgatgaaggt aaaggagaca ttg 23

<210> SEQ ID NO 19
<211> LENGTH: 23
<212> TYPE: DNA
<213> ORGANISM: Mus musculus

<400> SEQUENCE: 19
aggataatgg atgagcgtaa cag 23

<210> SEQ ID NO 20
<211> LENGTH: 23
<212> TYPE: DNA
<213> ORGANISM: Mus musculus

<400> SEQUENCE: 20
agcaacacct tatccatgtc agt 23

<210> SEQ ID NO 21
<211> LENGTH: 23
<212> TYPE: DNA
<213> ORGANISM: Mus musculus

<400> SEQUENCE: 21
cgttgtgtca tagtgcttgt aaa 23

<210> SEQ ID NO 22
<211> LENGTH: 23
<212> TYPE: DNA
<213> ORGANISM: Mus musculus

<400> SEQUENCE: 22
atcatgtaga gctcaaagtt cca 23

<210> SEQ ID NO 23
<211> LENGTH: 23
<212> TYPE: DNA
<213> ORGANISM: Mus musculus

<400> SEQUENCE: 23
tttctctgat ggccttacac taa 23

<210> SEQ ID NO 24
<211> LENGTH: 23
<212> TYPE: DNA
<213> ORGANISM: Mus musculus

<400> SEQUENCE: 24
agattaaaca gatggcactg aga 23

<210> SEQ ID NO 25
<211> LENGTH: 20
<212> TYPE: DNA
<213> ORGANISM: Mus musculus

```
<400> SEQUENCE: 25
atagctgatg gctgcaggtt                                          20

<210> SEQ ID NO 26
<211> LENGTH: 20
<212> TYPE: DNA
<213> ORGANISM: Mus musculus

<400> SEQUENCE: 26
aatctccact ttgccactgc                                          20

<210> SEQ ID NO 27
<211> LENGTH: 20
<212> TYPE: DNA
<213> ORGANISM: Mus musculus

<400> SEQUENCE: 27
aagctgagcg agtgtctccg                                          20

<210> SEQ ID NO 28
<211> LENGTH: 20
<212> TYPE: DNA
<213> ORGANISM: Mus musculus

<400> SEQUENCE: 28
ggaggaagtc cagtgtccag                                          20

<210> SEQ ID NO 29
<211> LENGTH: 20
<212> TYPE: DNA
<213> ORGANISM: Mus musculus

<400> SEQUENCE: 29
aacccaatgc ccgctgtgca                                          20

<210> SEQ ID NO 30
<211> LENGTH: 23
<212> TYPE: DNA
<213> ORGANISM: Mus musculus

<400> SEQUENCE: 30
accgaactca agaaggcca caa                                       23

<210> SEQ ID NO 31
<211> LENGTH: 29
<212> TYPE: DNA
<213> ORGANISM: Mus musculus

<400> SEQUENCE: 31
cgcggatcca ccatggtgat ttaatcaga                                29

<210> SEQ ID NO 32
<211> LENGTH: 29
<212> TYPE: DNA
<213> ORGANISM: Mus musculus

<400> SEQUENCE: 32
ccgctcgagc cgttcaaatc atttctcaa                                29

<210> SEQ ID NO 33
<211> LENGTH: 25
<212> TYPE: RNA
```

```
<213> ORGANISM: Mus musculus

<400> SEQUENCE: 33
aagcauuucu cucauuuccu caugg                                          25

<210> SEQ ID NO 34
<211> LENGTH: 29
<212> TYPE: DNA
<213> ORGANISM: Mus musculus

<400> SEQUENCE: 34
cgcggatcca ttcttcacac ttctcactt                                      29

<210> SEQ ID NO 35
<211> LENGTH: 29
<212> TYPE: DNA
<213> ORGANISM: Mus musculus

<400> SEQUENCE: 35
ccgctcgaga cgaagaagtc aacagcata                                      29

<210> SEQ ID NO 36
<211> LENGTH: 29
<212> TYPE: DNA
<213> ORGANISM: Mus musculus

<400> SEQUENCE: 36
ccgctcgaga aagcttgaat aatagaaat                                      29

<210> SEQ ID NO 37
<211> LENGTH: 30
<212> TYPE: DNA
<213> ORGANISM: Mus musculus

<400> SEQUENCE: 37
ctagtctaga atacatgggt ttttgtttg                                      30

<210> SEQ ID NO 38
<211> LENGTH: 29
<212> TYPE: DNA
<213> ORGANISM: Mus musculus

<400> SEQUENCE: 38
ccgctcgaga acgtgtaatt accttgaaa                                      29

<210> SEQ ID NO 39
<211> LENGTH: 30
<212> TYPE: DNA
<213> ORGANISM: Mus musculus

<400> SEQUENCE: 39
ctagtctaga caaagtcttc agaaacttaa                                     30

<210> SEQ ID NO 40
<211> LENGTH: 21
<212> TYPE: DNA
<213> ORGANISM: Mus musculus

<400> SEQUENCE: 40
gccacuauau aucaagguau t                                              21

<210> SEQ ID NO 41
<211> LENGTH: 21
```

```
<212> TYPE: DNA
<213> ORGANISM: Mus musculus

<400> SEQUENCE: 41
ggagccuuca aagcaggaat t                                              21

<210> SEQ ID NO 42
<211> LENGTH: 33
<212> TYPE: DNA
<213> ORGANISM: Mus musculus

<400> SEQUENCE: 42
cccaagctta tgtaccagtt ggatatcaca cta                                 33

<210> SEQ ID NO 43
<211> LENGTH: 30
<212> TYPE: DNA
<213> ORGANISM: Mus musculus

<400> SEQUENCE: 43
cccaagcttg ccaaggttgt tttttcttcc                                     30

<210> SEQ ID NO 44
<211> LENGTH: 28
<212> TYPE: DNA
<213> ORGANISM: Mus musculus

<400> SEQUENCE: 44
ccgctagcat gagcaccagc agccacgc                                       28

<210> SEQ ID NO 45
<211> LENGTH: 28
<212> TYPE: DNA
<213> ORGANISM: Mus musculus

<400> SEQUENCE: 45
ccaccggtct gcagcagtgg tgactgac                                       28

<210> SEQ ID NO 46
<211> LENGTH: 23
<212> TYPE: DNA
<213> ORGANISM: Homo sapiens

<400> SEQUENCE: 46
agatagcaag actttcctca gtc                                            23

<210> SEQ ID NO 47
<211> LENGTH: 23
<212> TYPE: DNA
<213> ORGANISM: Homo sapiens

<400> SEQUENCE: 47
ctgtggtgac ttgtccttta gta                                            23

<210> SEQ ID NO 48
<211> LENGTH: 23
<212> TYPE: DNA
<213> ORGANISM: Homo sapiens

<400> SEQUENCE: 48
ctactttacc aggacaagga atg                                            23

<210> SEQ ID NO 49
```

```
<211> LENGTH: 23
<212> TYPE: DNA
<213> ORGANISM: Homo sapiens

<400> SEQUENCE: 49
ctgagataaa tgagtgctag tgc                                              23

<210> SEQ ID NO 50
<211> LENGTH: 23
<212> TYPE: DNA
<213> ORGANISM: Homo sapiens

<400> SEQUENCE: 50
aggaatagtc agcatcacct tga                                              23

<210> SEQ ID NO 51
<211> LENGTH: 23
<212> TYPE: DNA
<213> ORGANISM: Homo sapiens

<400> SEQUENCE: 51
caatgactcc tcctctttct tca                                              23

<210> SEQ ID NO 52
<211> LENGTH: 23
<212> TYPE: DNA
<213> ORGANISM: Homo sapiens

<400> SEQUENCE: 52
cttctcagtg ccatctgctt aat                                              23

<210> SEQ ID NO 53
<211> LENGTH: 23
<212> TYPE: DNA
<213> ORGANISM: Homo sapiens

<400> SEQUENCE: 53
aattacacgc tctgcacctt tag                                              23

<210> SEQ ID NO 54
<211> LENGTH: 20
<212> TYPE: DNA
<213> ORGANISM: Homo sapiens

<400> SEQUENCE: 54
aagctgagcg agtgtctcaa                                                  20

<210> SEQ ID NO 55
<211> LENGTH: 20
<212> TYPE: DNA
<213> ORGANISM: Homo sapiens

<400> SEQUENCE: 55
agtagaaaag ggcgacaacc                                                  20

<210> SEQ ID NO 56
<211> LENGTH: 20
<212> TYPE: DNA
<213> ORGANISM: Homo sapiens

<400> SEQUENCE: 56
acgccccatc cagccgcatc                                                  20
```

```
<210> SEQ ID NO 57
<211> LENGTH: 23
<212> TYPE: DNA
<213> ORGANISM: Homo sapiens

<400> SEQUENCE: 57
cacacatgac cccaccgaac tca                                              23

<210> SEQ ID NO 58
<211> LENGTH: 20
<212> TYPE: DNA
<213> ORGANISM: Homo sapiens

<400> SEQUENCE: 58
ctgcattcgc cctcttaatg                                                  20

<210> SEQ ID NO 59
<211> LENGTH: 20
<212> TYPE: DNA
<213> ORGANISM: Homo sapiens

<400> SEQUENCE: 59
tgaggtcaat gaagggggtca                                                 20

<210> SEQ ID NO 60
<211> LENGTH: 24
<212> TYPE: DNA
<213> ORGANISM: Homo sapiens

<400> SEQUENCE: 60
gtggggaagc attaaaggac tgac                                             24

<210> SEQ ID NO 61
<211> LENGTH: 24
<212> TYPE: DNA
<213> ORGANISM: Homo sapiens

<400> SEQUENCE: 61
caattacacc acaagccaaa cgac                                             24

<210> SEQ ID NO 62
<211> LENGTH: 23
<212> TYPE: RNA
<213> ORGANISM: Homo sapiens

<400> SEQUENCE: 62
agaauuucaa ucaaucauuc cau                                              23

<210> SEQ ID NO 63
<211> LENGTH: 22
<212> TYPE: RNA
<213> ORGANISM: Homo sapiens

<400> SEQUENCE: 63
uggaauguaa ggaagugugu gg                                               22

<210> SEQ ID NO 64
<211> LENGTH: 23
<212> TYPE: RNA
<213> ORGANISM: Homo sapiens

<400> SEQUENCE: 64
uucuagcuac uucaaacauu ccc                                              23
```

```
<210> SEQ ID NO 65
<211> LENGTH: 22
<212> TYPE: RNA
<213> ORGANISM: Homo sapiens

<400> SEQUENCE: 65
aucauuuuaa aaaugcacc uu                                              22

<210> SEQ ID NO 66
<211> LENGTH: 23
<212> TYPE: RNA
<213> ORGANISM: Homo sapiens

<400> SEQUENCE: 66
uaaggugcau cuagugcagu uag                                            23
```